(12) United States Patent
Reches et al.

(10) Patent No.: US 8,796,023 B2
(45) Date of Patent: Aug. 5, 2014

(54) PEPTIDE NANOSTRUCTURES CONTAINING END-CAPPING MODIFIED PEPTIDES AND METHODS OF GENERATING AND USING THE SAME

(75) Inventors: Meital Reches, RaAnana (IL); Ehud Gazit, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 326 days.

(21) Appl. No.: 12/843,097

(22) Filed: Jul. 26, 2010

(65) Prior Publication Data
US 2010/0291828 A1    Nov. 18, 2010

Related U.S. Application Data

(62) Division of application No. 11/662,136, filed as application No. PCT/IL2005/000954 on Sep. 8, 2005, now Pat. No. 7,786,086.

(60) Provisional application No. 60/607,588, filed on Sep. 8, 2004.

(51) Int. Cl.
C12M 3/00 (2006.01)
C12M 1/12 (2006.01)

(52) U.S. Cl.
CPC .............. *C12M 25/14* (2013.01); *C12M 21/08* (2013.01)
USPC ........................... 435/398; 435/395; 435/400

(58) Field of Classification Search
None
See application file for complete search history.

(56) References Cited

U.S. PATENT DOCUMENTS

| | | |
|---|---|---|
| 3,042,685 A | 7/1962 | Roussel |
| 2,920,080 A | 1/1965 | Bucourt et al. |
| 3,625,973 A | 12/1971 | Julia |
| 3,790,596 A | 2/1974 | Shkilkova et al. |
| 3,853,987 A | 12/1974 | Dreyer |
| 3,867,517 A | 2/1975 | Ling |
| 3,935,074 A | 1/1976 | Rubenstein et al. |
| 3,976,639 A | 8/1976 | Batcho et al. |
| 3,984,533 A | 10/1976 | Uzgiris |
| 4,036,945 A | 7/1977 | Haber |
| 4,299,917 A | 11/1981 | Berger et al. |
| 4,331,647 A | 5/1982 | Goldenberg |
| 4,626,540 A | 12/1986 | Capps et al. |
| 4,666,828 A | 5/1987 | Gusella |
| 4,801,531 A | 1/1989 | Frossard |
| 4,816,567 A | 3/1989 | Cabilly et al. |
| 4,873,316 A | 10/1989 | Meade et al. |
| 4,925,673 A | 5/1990 | Steiner et al. |
| 4,946,778 A | 8/1990 | Ladner et al. |
| 4,970,233 A | 11/1990 | McHugh |
| 5,013,556 A | 5/1991 | Woodle et al. |
| 5,116,824 A * | 5/1992 | Miyata et al. ............... 514/55 |
| 5,171,505 A | 12/1992 | Lock |
| 5,270,163 A | 12/1993 | Gold et al. |
| 5,272,057 A | 12/1993 | Smulson et al. |
| 5,304,470 A | 4/1994 | Fischer et al. |
| 5,332,648 A | 7/1994 | Kihara et al. |
| 5,475,096 A | 12/1995 | Gold et al. |
| 5,545,806 A | 8/1996 | Lonberg et al. |
| 5,545,807 A | 8/1996 | Surani et al. |
| 5,567,588 A | 10/1996 | Gold et al. |
| 5,569,825 A | 10/1996 | Lonberg et al. |
| 5,595,877 A | 1/1997 | Gold et al. |
| 5,625,126 A | 4/1997 | Lonberg et al. |
| 5,633,425 A | 5/1997 | Lonberg et al. |
| 5,637,459 A | 6/1997 | Burke et al. |
| 5,643,768 A | 7/1997 | Kawasaki |
| 5,658,754 A | 8/1997 | Kawasaki |
| 5,659,041 A | 8/1997 | Pollak et al. |
| 5,661,016 A | 8/1997 | Lonberg et al. |
| 5,683,867 A | 11/1997 | Biesecker et al. |
| 5,705,337 A | 1/1998 | Gold et al. |
| 5,856,928 A | 1/1999 | Yan |
| 5,916,642 A | 6/1999 | Chang |
| 5,977,302 A | 11/1999 | Palmer et al. |
| 6,110,590 A | 8/2000 | Zarkoob et al. |
| 6,162,828 A | 12/2000 | Fukuda et al. |
| 6,235,876 B1 | 5/2001 | Palmer et al. |

(Continued)

FOREIGN PATENT DOCUMENTS

| | | |
|---|---|---|
| DE | 3412445 | 10/1985 |
| EP | 0421946 | 4/1991 |
| EP | 0966975 | 9/2005 |
| EP | 1583713 | 10/2005 |
| JP | 59-044313 | 3/1984 |
| JP | 60-040061 | 3/1985 |
| JP | 63-044895 | 2/1988 |
| JP | 02-295923 | 12/1990 |
| JP | 10-245342 | 9/1998 |
| JP | 2000-193661 | 7/2000 |

(Continued)

OTHER PUBLICATIONS

Genbank entry AAB19038.1, collagen.*
Ghadiri, M. Reza et al; "Artificial transmembrane ion channels from self-assembling peptide nanotubes." Nature (1994) 369 pp. 301-304.*
Holmes, Todd C. et al; "Extensive neurite outgrowth and active synapse formation on self assembling peptide scaffolds." PNAS (2000) 97(12) pp. 6728-6733.*
Ludtke, Steve J. et al; "Membrane pores induced by magainin." Biochemistry (1996) 35 pp. 13723-13728.*

(Continued)

*Primary Examiner* — James H Alstrum Acevedo
*Assistant Examiner* — Fred Reynolds

(57) ABSTRACT

A nanostructure composed of a plurality of peptides, each peptide containing at least one aromatic amino acid, whereby one or more of these peptides is end-capping modified, is disclosed. The nanostructure can take a tubular, fibrillar, planar or spherical shape, and can encapsulate, entrap or be coated by other materials. Methods of preparing the nanostructure, and devices and methods utilizing same are also disclosed.

12 Claims, 27 Drawing Sheets

(56) References Cited

U.S. PATENT DOCUMENTS

| | | |
|---|---|---|
| 6,251,625 B1 | 6/2001 | Bommarius et al. |
| 6,255,286 B1 | 7/2001 | Yanai et al. |
| 6,300,141 B1 | 10/2001 | Segal et al. |
| 6,303,567 B1 | 10/2001 | Findeis et al. |
| 6,309,669 B1 | 10/2001 | Setterstrom et al. |
| 6,326,174 B1 | 12/2001 | Joyce et al. |
| 6,359,112 B2 | 3/2002 | Kapurniotu et al. |
| 6,361,861 B2 | 3/2002 | Gao et al. |
| 6,376,233 B1 | 4/2002 | Wolf et al. |
| 6,472,436 B1 | 10/2002 | Schubert et al. |
| 6,593,339 B1 | 7/2003 | Eek et al. |
| 6,610,478 B1 | 8/2003 | Takle et al. |
| 6,613,875 B1 | 9/2003 | Ghadiri |
| 6,617,114 B1 | 9/2003 | Fowlkes et al. |
| 6,677,153 B2 | 1/2004 | Iversen |
| 6,762,331 B2 | 7/2004 | Hong et al. |
| 6,858,318 B2 | 2/2005 | Kogiso et al. |
| 6,976,639 B2 | 12/2005 | Williams et al. |
| 7,045,537 B1 | 5/2006 | Woolfson et al. |
| 7,491,699 B2 | 2/2009 | Reches et al. |
| 7,504,383 B2 | 3/2009 | Gazit et al. |
| 7,786,086 B2 | 8/2010 | Reches et al. |
| 8,017,586 B2 | 9/2011 | Gazit et al. |
| 8,053,554 B2 | 11/2011 | Reches et al. |
| 8,420,605 B2 | 4/2013 | Ulijn et al. |
| 8,501,697 B2 | 8/2013 | Gazit et al. |
| 8,568,637 B2 | 10/2013 | Gazit et al. |
| 2001/0041732 A1 | 11/2001 | Gurley et al. |
| 2002/0006954 A1 | 1/2002 | Hensley et al. |
| 2002/0086067 A1 | 7/2002 | Choi et al. |
| 2002/0151506 A1 | 10/2002 | Castillo et al. |
| 2003/0144185 A1 | 7/2003 | McGimpsey |
| 2003/0158237 A1 | 8/2003 | Saragovi et al. |
| 2003/0211007 A1 | 11/2003 | Maus et al. |
| 2003/0225155 A1 | 12/2003 | Fernandez-Pol et al. |
| 2004/0001893 A1 | 1/2004 | Stupp et al. |
| 2004/0029830 A1 | 2/2004 | Hebert |
| 2004/0052928 A1 | 3/2004 | Gazit |
| 2004/0152672 A1 | 8/2004 | Carson et al. |
| 2004/0258726 A1 | 12/2004 | Stupp et al. |
| 2005/0069950 A1 | 3/2005 | Haynie |
| 2005/0124535 A1 | 6/2005 | McGimpsey |
| 2006/0079454 A1 | 4/2006 | Reches et al. |
| 2006/0079455 A1 | 4/2006 | Gazit et al. |
| 2006/0089380 A1 | 4/2006 | Barnham et al. |
| 2006/0089489 A1 | 4/2006 | Onizuka et al. |
| 2006/0194777 A1 | 8/2006 | Gazit et al. |
| 2006/0234947 A1 | 10/2006 | Gazit |
| 2007/0015813 A1 | 1/2007 | Carter et al. |
| 2007/0021345 A1 | 1/2007 | Gazit |
| 2007/0099840 A1 | 5/2007 | Ulijn et al. |
| 2007/0135334 A1 | 6/2007 | Gazit |
| 2007/0138007 A1 | 6/2007 | Yemini et al. |
| 2007/0298043 A1 | 12/2007 | Gazit et al. |
| 2008/0009434 A1 | 1/2008 | Reches et al. |
| 2009/0061190 A1 | 3/2009 | Gazit et al. |
| 2009/0121709 A1 | 5/2009 | Gazit et al. |
| 2009/0123553 A1 | 5/2009 | Reches et al. |
| 2009/0175785 A1 | 7/2009 | Gazit et al. |
| 2009/0263429 A1 | 10/2009 | Ulijn et al. |
| 2010/0291828 A1 | 11/2010 | Reches et al. |
| 2011/0266517 A1 | 11/2011 | Gazit et al. |
| 2012/0063276 A1 | 3/2012 | Reches et al. |
| 2013/0075703 A1 | 3/2013 | Gazit et al. |
| 2014/0027655 A1 | 1/2014 | Reches et al. |
| 2014/0044949 A1 | 2/2014 | Gazit et al. |

FOREIGN PATENT DOCUMENTS

| | | |
|---|---|---|
| WO | WO 80/00789 | 1/1980 |
| WO | WO 97/16191 | 5/1997 |
| WO | WO 98/20135 | 5/1998 |
| WO | WO 99/42102 | 8/1999 |
| WO | WO 99/58652 | 11/1999 |
| WO | WO 00/24390 | 5/2000 |
| WO | WO 01/05421 | 1/2001 |
| WO | WO 01/10457 | 2/2001 |
| WO | WO 01/45726 | 6/2001 |
| WO | WO 01/49307 | 7/2001 |
| WO | WO 02/072086 | 9/2002 |
| WO | WO 02/094857 | 11/2002 |
| WO | WO 03/013442 | 2/2003 |
| WO | WO 03/024443 | 3/2003 |
| WO | WO 03/039540 | 5/2003 |
| WO | WO 03/063760 | 8/2003 |
| WO | WO 03/069033 | 8/2003 |
| WO | WO 03/070269 | 8/2003 |
| WO | WO 03/077866 | 9/2003 |
| WO | WO 2004/050693 | 6/2004 |
| WO | WO 2004/052773 | 6/2004 |
| WO | WO 2004/060791 | 7/2004 |
| WO | WO 2005/016339 | 2/2005 |
| WO | WO 2005/020809 | 3/2005 |
| WO | WO 2005/027901 | 3/2005 |
| WO | WO 2005/031362 | 4/2005 |
| WO | WO 2005/085867 | 9/2005 |
| WO | WO 2006/006172 | 1/2006 |
| WO | WO 2006/013552 | 2/2006 |
| WO | WO 2006/018850 | 2/2006 |
| WO | WO 2006/020681 | 2/2006 |
| WO | WO 2006/027780 | 3/2006 |
| WO | WO 2007/029003 | 3/2007 |
| WO | WO 2007/043048 | 4/2007 |
| WO | WO 01/49281 | 7/2007 |

OTHER PUBLICATIONS

Maji, Samir Kumar et al; "Fibril forming model synthetic peptides containing 3-amino phenylacetic acid." Tetrahedron (2002) 58 pp. 8695-8702.*

Murphy, Gillian et al; "Matrix metalloproteinase degradation of elastin, type IV collagen and proteoglycan." Biochem J. (1991) 277 pp. 277-279.*

Hiemenz, Paul C; "Principles of colloid and surface chemistry." Marcel Dekker ISBN 0/8247-7476-0.*

Soppimath, Kumaresh S. et al; "Biodegradable polymeric nanoparticles as drug delivery devices." J. Cont. Rel. (2001) 70 pp. 1-20.*

Barrett, J. Carl et al; "Multiple mechanisms for the carcinogenic effects of asbestos and other mineral fibers." Environ. Health. Persp. (1989) 81 (81-89.*

Nishimura, Isao et al; "Par-1 kinase plays an initiator role in temprally orderd phosphorylation process that confers tau toxicity in drosophila." Cell (2004) 116 pp. 671-682.*

MacPhee, Cait E. and Woolfson, Derek N.; "Engineered and desgined peptide based fibrous biomaterials." Curr. Opin. Solid State Mat. Sci. (2004) 8 pp. 141-149.*

Lutolf, Matthias P. et al; "Cell responsive synthetic hydrogels." Adv. Mat. (2003) 15(11) pp. 888-892.*

Notice of Allowance Dated Mar. 7, 2011 From the US Patent and Trademark Office Re.: U.S. Appl. No. 12/318,653.

Official Action Dated Apr. 3, 2009 From the US Patent and Trademark Office Re.: U.S. Appl. No. 11/662,136.

Official Action Dated Jul. 14, 2008 From the US Patent and Trademark Office Re.: U.S. App. No. 11/662,136.

Official Action Dated Nov. 26, 2008 From the US Patent and Trademark Office Re.: U.S. Appl. No. 11/662,136.

Summons to Attend Oral Proceedings Pursuant to Rule 115(1) EPC Dated Nov. 30, 2011 From the European Patent Office Re. Application No. 09002048.8.

Communication Pursuant to Article 94(3) EPC Dated Nov. 23, 2010 From the European Patent Office Re.: Application No. 09002048.8.

Official Action Dated Dec. 10, 2010 From the US Patent and Trademark Office Re.: U.S. Appl. No. 12/318,619.

Response Dated Dec. 8, 2010 to Communication Pursuant to Article 94(3) EPC of Jun. 8, 2010 From the European Patent Office Re.: Application No. 06796163.1.

Response Dated Oct. 17, 2010 to Office Action of Jun. 17, 2010 From the Israel Patent Office Re.: Application No. 169120 and Its Translation Into English.

(56) References Cited

OTHER PUBLICATIONS

Response Dated Nov. 22, 2010 to Official Action of Jul. 22, 2010 From the US Patent and Trademark Office Re.: U.S. Appl. No. 12/318,653.
Response Dated Oct. 28, 2010 to Office Action of May 30, 2010 From the Israel Patent Office Re.: Application No. 169121.
Gazit "Diversity for Self-Assembly", Nature Chemistry, 2: 1010-1011, Dec. 2010.
Hirst et al. "Biocatalytic Induction of Supramolecular Order", Nature Chemistry, 2: 1089-1094, Dec. 2010.
Official Action Dated Mar. 16, 2011 From the US Patent and Trademark Office Re. U.S. Appl. No. 12/083,222.
Response Dated Feb. 22, 2011 to Examiner's Telephone Call of Feb. 22, 2011 From the US Patent and Trademark Office Re. U.S. Appl. No. 12/318,653.
Official Action Dated Apr. 17, 2012 From the US Patent and Trademark Office Re. U.S. Appl. No. 12/083,222.
Response Dated Mar. 10, 2011 to Official Action of Dec. 10, 2010 From the US Patent and Trademark Office Re.: U.S. Appl. No. 12/318,619.
Response Dated Apr. 13, 2011 to Official Action of Mar. 16, 2011 From the US Patent and Trademark Office Re. U.S. Appl. No. 12/083,222.
Official Action Dated Aug. 30, 2010 From the US Patent and Trademark Office Re.: U.S. Appl. No. 12/318,619.
Office Action Dated Jun. 21, 2011 From the Israel Patent Office Re.: Application No. 169120 and Its Translation Into English.
Notice of Allowance Dated Aug. 31, 2012 From the US Patent and Trademark Office Re. U.S. Appl. No. 13/290,147.
Summons to Attend Oral Proceedings Pursuant to Rule 115(1) EPC Dated Sep. 13, 2012 From the European Patent Office Re. Application No. 06796163.1.
Robinson et al. "The Design of a Biochip: A Self-Assembling Molecular-Scale Memory", Protein Engineering, 1(4): 295-300, 1987.
Yan et al. "Self-Assembling and Application of Diphenylalanine-Based Nanostructures", Chemical Society Reviews, 39: 1877-1890, 2010.
Notice of Allowability Dated May 21, 2010 From the US Patent and Trademark Office Re.: U.S. Appl. No. 11/662,136.
Notice of Allowance Dated Jun. 9, 2011 From the US Patent and Trademark Office Re.: U.S. Appl. No. 12/318,619.
Notice of Allowance Dated Sep. 23, 2010 From the US Patent and Trademark Office Re.: U.S. Appl. No. 11/591,613.
Notice of Allowance Dated Mar. 26, 2010 From the US Patent and Trademark Office Re.: U.S. Appl. No. 11/662,136.
Balaram "De Novo Design: Backbone Conformational Constraints in Nucleating Helices and β-Hairpins", Journal of Peptide Research, 54: 195-199, 1999.
Beugelmans Database Crossfire Beilstein [Online], Beilstein Institut zur Förderung der Chemischen Wissenschaften, Frankfurt am Main, DE, Database Accession No. 116671 (BRN) Compounds INDOL-2-YL-Methanol & Beugelmans R.: Bulletin de la Société Chimique Francaise, pp. 335-336, 1969.
Clark et al. "Self-Assembling Cyclic β3-Peptide Nanotubes as Artificial Transmembrane Ion Channels", Journal of the American Chemical Society, 120: 651-656, 1998.
Görbitz "Nanotube Formation by Hydrophobic Dipeptides", Chemical European Journal, Chemistry, XP001180634, 7(23): 5153-5159, Dec. 3, 2001.
Lashuel et al. "New Class of Inhibitors of Amyloid-β Fibril Formation. Implications for the Mechanism of Pathogenesis in Alzheimer's Disease", The Journal of Biological Chemistry, 277(45): 42881-42890, 2002.
Tsai et al. "Synthesis of AIB-Containing Peptidomimetics as Potential Inhibitors of Alzheimer's γ-Secretase", 218th ACS National Meeting, New Orleans, USA, Meeting Abstract, MEDI-018, 1999. Abstract.
Notice of Allowance Dated Jul. 12, 2012 From the US Patent and Trademark Office Re.: U.S. Appl. No. 13/179,638.

Official Action Dated Jul. 22, 2010 From the US Patent and Trademark Office Re.: U.S Appl. No. 12/318,653.
Examination Report Dated Sep. 23, 2011 From the Government of India, Patent Office, Intellectual Property Building Re. Application No. 915/CHENP/2007.
Office Action Dated Aug. 22, 2011 From the Israel Patent Office Re.: Application No. 169121 and Its Translation Into English.
International Search Report and the Written Opinion Dated Jul. 15, 2008 From the International Searching Authority Re.: Application No. PCT/IL05/00954.
Beugelmans Database Crossfire Beilstein [Online], Beilstein Institut zur Förderung der Chemischen Wissenschaften, Frankfurt am Main, DE, Database Accession No.116671 (BRN) Compounds INDOL-2-YL-Methanol & Beugelmans R.: Bulletin de la Société Chimique Francaise, pp. 335-336, 1969.
Gazit "Mechanistic Studies of Process of Amyolid Fibrils Formation by the Use of Peptide Fragments and Analogues: Implications for the Design of Fibrillization Inhibitors", Current Medicinal Chemistry, 9: 1725-1735, 2002.
Jin "Electrospinning Bombyx Mori Silk With Poly (Ethylene Oxide)" Biomacromolecules, 3: 1233-1239, 2002.
Reches et al. "Designed Aromatic Homo-Dipeptides: Formation of Ordered Nanostructures and Potential Nanotechnological Applications", Physical Biology, 3: S10-S19, 2006.
Official Action Dated Jan. 12, 2012 From the US Patent and Trademark Office Re. U.S. Appl. No. 13/179,638.
Perutz et al. "Amyloid Fibers Are Water-Filled Nanotubes", Proc. Natl. Acad. Sci USA, PNAS, 99(8): 5591-5595, Apr. 16, 2002.
Reches et al. "Formation of Closed-Cage Nanostructures by Self-Assembly of Aromatic Dipeptides", Nano Letters, 4(4): 581-585, 2004.
Communciation Pursuant to Article 96(2) EPC Dated Mar. 30, 2006 From the European Patent Office Re.: Application No. 04700494.0.
Communication Pursuant to Article 94(3) EPC Dated Sep. 4, 2008 From the European Patent Office Re.: Application No. 03777149.0.
Communication Pursuant to Article 94(3) EPC Dated Jun. 8, 2010 From the European Patent Office Re.: Application No. 06796163.1.
Communication Pursuant to Article 94(3) EPC Dated Aug. 11, 2009 From the European Patent Office Re.: Application No. 05747261.5.
Communication Pursuant to Article 94(3) EPC Dated Sep. 15, 2009 From the European Patent Office Re.: Application No. 09002048.8.
Communication Pursuant to Article 94(3) EPC Dated Dec. 29, 2009 From the European Patent Office Re.: Application No. 03777149.0.
Communication Pursuant to Article 96(2) EPC Dated May 14, 2007 From the European Patent Office Re.: Application No. 03777149.0.
Communication Pursuant to Article 96(2) EPC Dated Jul. 17, 2006 From the European Patent Office Re.: Application No. 03777149.0.
Communication Pursuant to Article 96(2) EPC Dated Jan. 18, 2007 From the European Patent Office Re.: Application No. 04700494.0.
Communication Pursuant to Rules 109 and 110 EPC Dated Aug. 18, 2005 From the European Patent Office Re.: Application No. 04700494.0.
Communication Under Rule 112 EPC Dated Mar. 31, 2006 From the European.Patent Office Re.: Application No. 03777149.0.
Communication Under Rule 71(3) EPC Dated Oct. 7, 2008 From the European Patent Office Re.: Application No. 04700494.0.
Examination Report Dated May 10, 2007 From the Government of India, Patent Office Re.: Application No. 1499/CHENP/2005.
Examination Report Dated Jun. 19, 2006 From the Intellectual Property Office of India Re.: Application No. 1510/CHENP/2005.
International Preliminary Report on Patentability Dated Feb. 15, 2007 From the International Bureau of WIPO Re.: Application No. PCT/IL2005/000589.
International Preliminary Report on Patentability Dated Jan. 22, 2009 From the International Bureau of WIPO Re.: Application No. PCT/IL2005/000954.
International Preliminary Report on Patentability Dated Apr. 24, 2008 From the International Bureau of WIPO Re.: Application No. PCT/IL2006/001174.
International Search Report and the Written Opinion Dated Nov. 3, 2006 From the International Searching Authority Re.: Application No. PCT/IL05/00589.

(56) References Cited

OTHER PUBLICATIONS

International Search Report and the Written Opinion Dated May 10, 2004 From the International Searching Authority Re.: Application No. PCT/IL2004/000012.

International Search Report and the Written Opinion Dated Aug. 22, 2007 From the International Searching Authority Re.: Applicaiton No. PCT/IL2006/001174.

International Search Report Dated Jul. 19, 2004 From the International Searching Authority Re.: Application No. PCT/IL03/01045.

Notice of Allowance Dated Sep. 17, 2008 From the US Patent and Trademark Office Re.: U.S. Appl. No. 11/148,266.

Notice of Allowance Dated Jun. 18, 2008 From the US Patent and Trademark Office Re.: U.S. Appl. No. 11/148,262.

Office Action Dated Aug. 4, 2009 From the Israel Patent Office Re.: Application No. 169120 and Its Translation Into English.

Office Action Dated Jul. 14, 2009 From the Israel Patent Office Re.: Application No. 169121 and Its Translation Into English.

Office Action Dated Sep. 15, 2008 From the Israel Patent Office Re.: Application No. 169120 and Its Translation Into English.

Office Action Dated Sep. 15, 2008 From the Israel Patent Office Re.: Application No. 169121 and Its Translation Into English.

Office Action Dated Jun. 17, 2010 From the Israel Patent Office Re.: Application.No. 169120 and Its Translation Into English.

Office Action Dated May 30, 2010 From the Israel Patent Office Re.: Application No. 169121 and Its Translation Into English.

Official Action Dated Apr. 1, 2010 From the US Patent and Trademark Office Re.: U.S. Appl. No. 11/591,613.

Official Action Dated Jun. 9, 2010 From the US Patent and Trademark Office.Re.: U.S. Appl. No. 11/662,136.

Official Action Dated Dec. 11, 2009 From the US Patent and Trademark Office Re.: U.S. Appl. No. 12/318,653.

Official Action Dated Feb 15, 2008 From the US Patent and Trademark Office Re.: U.S. Appl. No. 11/148,262.

Official Action Dated Sep. 19, 2007 From the US Patent and Trademark Office Re.: U.S. Appl. No. 11/148,262.

Official Action Dated Jun. 22, 2009 From the US Patent and Trademark Office Re.: U.S. Appl. No. 12/318,653.

Official Action Dated Sep. 27, 2007 From the US Patent and Trademark Office Re.: U.S. Appl. No. 11/148,266.

Official Action Dated Apr. 30, 2007 From the US Patent and Trademark Office Re.: U.S. Appl. No. 11/148,262.

Official Action Dated Jun. 30, 2010 From the US Patent and Trademark Office Re.: U.S. Appl. No. 11/662,136.

Partial European Search Report and the European Search Opinion Dated Apr. 16, 2009 From the European Patent Office Re.: Application No. 09002048.8.

Response Dated Dec. 9, 2009 to Communication Pursuant to Article 94(3) EPC of Aug. 11, 2009 From the European Patent Office Re.: Application No. 05747261.5.

Response Dated Jul. 9, 2008 to Notice of Allowance of Jun. 18, 2008 From the US Patent and Trademark Office Re.: U.S. Appl. No. 11/148,262.

Response Dated Mar. 9, 2009 to Communication Pursuant to Article 94(3) EPC of Sep. 4, 2008 From the European Patent Office Re.: Application No. 03777149.0.

Response Dated Apr. 12, 2010 to Official Action of Dec. 11, 2009 From the US Patent and Trademark Office Re.: U.S. Appl. No. 12/318,653.

Response Dated Jan. 12, 2010 to Communication Pursuant to Article 94(3) EPC of Sep. 15, 2009 From the European Patent Office Re.: Application No. 09002048.8.

Response Dated Dec. 13, 2007 to Communication Pursuant to Article 96(2) EPC of 17 Jul. 2006 From the European Patent Office Re.: Application No. 03777149.0.

Response Dated Nov. 15, 2009 to Office Action of Jul. 14, 2009 From the Israel Patent Office Re.: Application No. 169121.

Response Dated Apr. 22, 2010 to Communication Pursuant to Article 94(3) EPC of Dec. 29, 2009 From the European Patent Office Re.: Application No. 03777149.0.

Response Dated May 22, 2007 to Communication Pursuant to Article 96(2) EPC of Jan. 18, 2007 From the European Patent Office Re.: Application No. 04700494.0.

Response Dated May 25, 2007 to Communication Pursuant to Article 96(2) EPC of Jan. 18, 2007 From the European Patent Office Re.: Application No. 04700494.0.

Response Dated Jun. 30, 2010 to Official Action of Apr. 1, 2010 From the US Patent and Trademark Office Re.: U.S. Appl. No. 11/591,613.

Response With Updated Set of Claims Dated Feb. 16, 2010 to Communication Pursuant to Article 94(3) EPC of Sep. 15, 2009 From the European Patent Office Re.: Application No. 09002048.8.

Second Notice of Allowance Dated Sep. 16, 2008 From the US Patent and Trademark Office Re.: U.S. Appl. No. 11/148,262.

Supplementary European Search Report Dated Jun. 10, 2009 From the European Patent Office Re.: Application No. 05747261.5.

Ajayan et al. "Application of Carbon Nanotubes", Topics of Applied Physics, 80: 391-425, 2001.

Akazome et al. "Enantioselective Inclusion of Methyl Phenyl Sulfoxides and Benzyl Methyl Sulfoxides by (R)-Phenylglycyl-(R)-Phenylglycine and the Crystal Structures of the Inclusion Cavities", Journal of Organic Chemistry, 65(1): 68-76, 2000.

Altland et al. "Potential Treatment of Transthyretin-Type Amyloidoses by Sulfite", Neurogenetics, 2: 183-188, 1999.

Appukkuttan et al. "Microwave Enhanced Formation of Electron Rich Arylboronates", Synlett, 8: 1204-1206, 2003. Figs., Scheme 4, Compounds 5A, 5B, 5C, 5D.

Azriel et al. "Analysis of the Minimal Amyloid-Forming Fragment of the Islet Amyloid Polypeptide", The Journal of Biological Chemistry, 276(36): 34156-34161, 2001.

Berson et al. "Proprotein Convertase Cleavage Liberates Λ Fibrillogenic Fragment of A Resident Glycoprotein to Initiate Melanosome Biogenesis", Journal of Cell Biology, 161(3): 521-533, 2003.

Beugelmans Database Crossfire Beilstein [Online], Beilstein Institut zur Förderung der Chemischen Wissenschaften, Frankfurt am Main, DE, Database Accession No. 116671 (BRN) Compounds INDOL-2-YL-Methanol & Beugelmans R • Bulletin de la Société Chimique Française, pp. 335-336, 1969.

Bong et al. "Self-Assembling Organic Nanotubes", Angewandte Chemie, International Edition, 40:988-1011, 2001.

Changqing et al. "Amyloid-Like Formation by Self-Assembly of Peptidolipids in Two Dimensions", Langmuir, 20: 8641-8645, 2004.

Chapman et al. "Role of *Escherichia Coli* Curli Operons in Directing Amyloid Fiber Formation", Science, 295(5556): 851-855, 2002. Abstract.

Cherny et al. "The Formation of *Escherichia Coli* Curli Amyloid Fibrils is Mediated by Prion-Like Peptide Repeats", Journal of Molecular Biology, 352(2): 245-252, 2005.

Cherny et al. "The YcfM Antitoxin Defines A Family of Natively Unfolded Proteins", The Journal of Biological Chemistry, 279(9): 8252-8261, Feb. 27, 2004.

Chou et al. "Empirical Predictions of Protein Conformation", Annual Reviews in Biochemistry, 47: 251-276, 1978.

Claessen et al. "A Novel Class of Secreted Hydrophodic Proteins is Involved in Aerial Hyphae Formation in Streptomyces Coelicolor by Forming Amyloid-Like Fibrils", Genes & Development, 17: 1714-1726, 2003.

Cohen et al "Inhibition of Amyloid Fibril Formation and Cytotoxicity by Hydroxyindole Derivatives", Biochemistry, 45: 4727-4735, 2006. P.4728, col. 1, Last §, p. 4728, col. 2, § 2, p. 4729, col. 1, Last §, col. 2, § 2, Fig. 1, 4, p. 4732, col. 2, § 2, 3, p. 4733, col. 2, § 4.

Elliot et al. "The Chaplins: A Family of Hydrophobic Cell-Surface Proteins Involved in Aerial Mycelium Formation in Streptomyces Coelicolor", Genes & Development, 17: 1727-1740, 2003.

Engelberg-Kulka et al. "Bacterial Programmed Cell Death Systems as Targets for Antibiotics", Trends in Microbiology, XP002477942, 12(2): 66-71, Feb. 2004.

Forloni et al. "Anti-Amyloidogenic Activity of Tetracyclines: Studies in Vitro", FEBS Letters, 487(3): 404-407, 2001. Abstract, Results, Figs. 1, 3.

(56) References Cited

OTHER PUBLICATIONS

Ganesh et al. "Circular Dichroism and Fourier Transform Infrared Spectroscopic Studies on Self-Assembly of Tetrapeptide Derivative in Solution and Solvated Film", The Journal of Peptide Research: Official Journal of the American Peptide Society, XP002529296, 61(3): 122-128, Mar. 2003.
Gazit "A Possible Role for 'Phi'-Stacking in the Self-Assembly of Amyloid Fibrils", The FASEB Journal, 16: 77-83, 2002.
Gazit "Mechanisms of Amyloid Fibril Self-Assembly and inhibition Model Short Peptides as A Key Research Tool", The FEBS Journal, 272: 5971-5978, 2005.
Ghadiri et al. "Artificial Transmembrane Ion Channels From Self-Assembling Peptide Nanotubes", Nature, 369(6478): 301-304, 1994.
Ghadiri et al. "Self-Assembling Organic Nanotubes Based on a Cyclic Peptide Architecture", Nature, XP002936460, 366: 324-327, Dec. 25, 1993.
Gorman et al. "Alzheimer Beta-Amyloid Peptides, Structures of Amyloid Fibrils and Alternate Aggregation Products", Biopolymers, 60: 381-394, 2001.
Grady et al. "Axe—Txe, a Broad-Spectrum Proteic Toxin—Antitoxin System Specified by a Multidrug-Resistant, Clinical Isolate of Enterococcus Faecium", Molecular Microbiology, 47(5): 1419-1432, 2003. Abstract, p. 1424, col. 1—p. 1426, col. 2, Fig. 5.
Haldar et al. "First Crystallographic Signature of the Highly Ordered Supramolecular Helical Assemblage From A Tripeptide Containing A Non-Coded Amino Acid", Tetrahedron Letters, XP004343975, 43(14): 2653-2656, 2002. Abstract.
Hartgerink et al. "Peptide Nanotubes and Beyond", Chemistry European Journal, XP002276851, 4(8): 1367-1372, 1998. Abstract.
Hartgerink et al. "Self-Assembling Peptide Nanotubes", Journal of the American Chemical Society, 118: 43-50, 1996.
Hayden et al. "'A' Is for Amylin and Amyloid in Type 2 Diabetes Mellitus", JOP Journal of the Pancreas (Online), 2(4): 124-139, 2001.
Holmes et al. "Extensive Neurite Outgrowth and Active Synapse Formation on Self-Assembling Peptide Scaffolds", Proc. Natl. Acad. Sci. USA, XP002213924, 97(12): 6728-6733, Jun. 6, 2000.
Honma et al. "Use of a Thromboxane A2 Antagonist or Synthase Inhibitor for Treating Central Nervous System Diseases, c. g. Alzheimer Type Dementia," Database WPI, Section Ch. Week 200039, Derwent Publications, Class B05, AN 2000-451668, Jun. 2, 2000. Abstract. & WO 00/30683.
Horne et al. "A Heterocyclic Peptide Nanotube", Journal of the American Chemical Society, JACS, XP002276671, 125(31): 9372-9376, Aug. 6, 2003. Abstract.
Hoyle et al. "*Pseudomonas Aeruginosa* Biofilm as a Diffusion Barrier to Piperacillin", Antimicrobial Agents and Chemotherapy, 36(9): 2054-2056, 1992.
Huang et al. "A Review on Polymer Nanofibers by Electrospinning and Their Applications in Nanocomposites", Composites Science and Technology, 63: 2223-2253, 2003.
Inglot "Comparison of the Antiviral Activity in Vitro of Some Non-Steroidal Anti-Inflammatory Drugs", Journal of General Virology, 4(2): 203-214, 1969.
Jack et al. "The Organization of Aromatic Side Groups in an Amyloid Fibril Probed by Solid-State 2H and 19F NMR Spectroscopy", Journal of the American Chemical Society, JACS, 128: 8098-8099, 2006.
Jayawarna et al. "Nanostructured Hydrogels for Three-Dimensional Cell Culture Through Self-Assembly of Fluorenylmethoxycarbonyl-Dipeptides", Advanced Materials, XP002446151, 18: 611-614, 2006.
Kaplan "Fibrous Proteins-Silk as A Model System", Polymer Degradation and Stability, 59: 25-32, 1998.
Kerman et al. "Peptide Nucleic Acid-Modified Carbon Nanotube Field-Effect Transistor for Ultra-Sensitive Real-Time Detection of DNA Hybridization", NanoBiotechnology, 1(1): 65-70, Mar. 2005.
Kimura et al. "Analysis and Prediction of Absorption Profile Including Hepatic First-Pass Metabolism of N-Methyltyramine, A Potent Stimulant of Gastrin Release Present in Beer, After Oral Ingestion in Rats by Gastrointestinal-Transit-Absorption Model", Drug Metabolism and Disposition, 28(5): 577-581, 2000.
Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, Class B02, AN 2003-286683, Jan. 20, 2003. Abstract. & RU 2196568.
Kisilevsky et al. "Arresting Amyloidosis in Vivo Using Small-Molecule Anionic Sulphonates or Sulphates: Implications for Alzheimer's Disease", Nature Medicine, 1: 143-148, 1995. Abstract.
Kocisko et al. "New Inhibitors of Scrabie-Associated Prion Protein Formation in A Library of 2,000 Drugs and Natural Products", Journal of Virology, 77(19): 10288-10294, 2003.
Kon-Ya et al. "Indole Derivatives as Potent Inhibitors of Larval Settlement by the Barnacle, Balanus Amphitrite", Bioscience, Biotechnology and Biochemistry, 58(12): 2178-2181, 1994. Compound 102.
Kubik "High-Performance Fibers From Spider Silk", Angewandte Chemie, International Edition, 41(15): 2721-2723, 2002.
Lansbury Jr. "Following Nature's Anti-Amyloid Strategy", Nature Biotechnology, 19(2): 112-113, 2001.
Lazaris et al. "Spider Silk Fibers Spun From Soluble Recombinant Silk Produced in Mammalian Cells", Science, 295: 472-476, 2002. pp. 474-475.
Lee et al. "Anti-Diabetic Constituent From the Node of Lotus Rhizome (Nelumbo Nucifera Gaertn)", Natural Product Sciences, 7(4), 107-109, 2001.
Lee et al. "Virus-Based Fabrication of Micro- and Nanofibers Using Electrospinnig", Nano Letters, 4(3): 387-390, Mar. 2004.
Li et al. "Amyloid-Like Formation by Self-Assembly of Peptidolipids in Two Dimensions", Langmuir: The ACS Journal of Surfaces and Colloids, XP002529300, 20(20): 8641-8645, Aug. 24-Sep. 28, 2004.
Liao et al. "Triphenylmethane Dyes as Inhibitors of Reverse Transcriptase RNA Polymerase and Protein Synthesis: Structure Activity Relationships", Journal of Medicinal Chemistry, 18(1): 117-120, 1975. Abstract.
MacPhee et al. "Engineered and Designed Peptide-Based Fibrous Biomaterials", Current Opinion in Solid State and Materials Science, XP002529298, 8(2): 141-149, Mar. 2004.
Mah et al. "A Genetic Basis for Pseudomonas Aeruginosa Biofilm Antibiotic Resistance", Nature, 426: 306-310, 2003.
Mahler et al. "Rigid, Self-Assembled Hydrogel Composed of A Modified Aromatic Dipeptide", Advanced Materials, XP002446150, 18(11): 1365-1370, 2006.
Maji et al. "Fibril-Forming Model Synthetic Peptides Containing 3-Aminophenylacetic Acid", Tetrahedron, XP004390176, 58(43): 8695-8702, 2002.
Martin et al. "The Emerging Field of Nanotube Biotechnology", Nature Reviews: Drug Discovery, 2(1): 29-37, Jan. 2003. Abstract.
Matsui et al. "Crystalline Glyclylglycine Bolaamphiphile Tubules and Their pH-Sensitive Structural Transformation" The Journal of Physical Chemistry B, 104(15): 3384-3386, 2000.
Meluleni et al. "Mucoid Pseudomonas Aeruginosa Growing in A Biofilm in Vitro Are Killed by Opsonic Antibodies to the Mucoid Exopolysaccharide Capsule But Not by Antibodies Produced During Chronic Lung Infection in Cystic Fibrosis Patients,", Journal of Immunology, 155: 2029-2038, 1995.
Murphy et al. "Biofilm Formation by Nontypeable Haemophilus Influenzae: Strain Variability, Outer Membrane Antigen Expression and Role of Pili", BMC Microbiology, 2(7): 1471-2180, 2002.
Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.
Oza et al. "Synthesis and Evaluation of Anthranilic Acid-Based Transthyretin Amyloid Fibril Inhibitors", Bioorganic & Medicinal Chemistry Letters 9(1): 1-6, 1999.
Pavia et al. "Antimicrobial Activity of Nicotine Against a Spectrum of Bacterial and Fungal Pathogens", Journal of Medical Microbiology, 49(7): 675-676, 2000.
Peterson et al "Inhibiting Transthyretin Conformational Chamges That Lead to Amyloid Fibril Formation", Proc. Natl. Acad. Sci. USA, 95: 12956-12960, 1998.

(56) References Cited

OTHER PUBLICATIONS

Pispisa et al. "A Spectroscopic and Molecular Mechanics Investigation on A Series of AIB-Based Linear Peptides and A Peptide Template, Both Containing Tryptophan and A Nitroxide Derivative as Probes", Biopolymers, 53: 169-181, 2000.
Rajagopal et al. "Self-Assembling Peptides and Proteins for Nanotechnological Applications", Current Opinion in Structural Biology, XP002529297, 14(4): 480-486, Aug. 2004.
Reches et al. "Amyloid Fibril Formation by Pentapeptide and Tetrapeptide Fragments of Human Calcitonin", The Journal of Biological Chemistry, XP002276670, 277(38): 35475-35480, 2002.
Reches et al. "Casting Metal Nanowires Within Discrete Self-Assembled Peptide Nanotubes", Science, XP002276672, 300(5619): 625-627, Apr. 25, 2003. "Supporting Online Materials", Science [Online], 300(5619): 1-9, Apr. 25, 2003. Retrieved From the Internet on Aug. 7, 2007.
Reches et al. "Self-Assembly of Peptide Nanotubes and Amyloid-Like Structures by Charged-Termini-Capped Diphenylalanine Peptide Analogues", Israel Journal of Chemistry, XP009087914, 45(3): 363-371, Jun. 30, 2005.
Reches et al. "Supporting Online Material", Science, 300(5619): 1-9, 2003. Retrieved From the Internet: URL:http://www.sciencemag.org/cgi/data/300/5619/625/DC1.
Ryadnov et al. "Engineering the Morphology of A Self-Assembling Protein Fibre", Nature Materials, XP002529299, 2(5): 329-332, May 2003.
Sacchettini et al. "Therapeutic Strategies for Human Amyloid Diseases", Nature Reviews: Drug Discovery, 1: 267-275, 2002.
Soto et al. "Beta-Sheet Breaker Peptides Inhibit Fibrillogenesis in a Rat Brain Model of Amyloidosis: Implications for Alzheimer's Therapy", Nature Medicine 4(7): 822-826, 1998.
Stephenson et al. "The 'Promiscuous Drug Concept' With Applications to Alzheimer's Disease", FEBS Letters, 579: 1338-1342, 2005.
Stewart "Theoretical Aspects of Antibiotic Diffusion Into Microbial Biofilms", Antimicrobial Agents and Chemotherapy, 40(11): 2517-2522, 1996.
Toledano et al. "Enzyme-Triggered Self-Assembly of Peptide Hydrogels Via Reversed Hydrolysis", Journal of the American Chemical Society, JACS, XP002421984, 128(4): 1070-1071, Feb. 1, 2006.
True et al. "Epigenetic Regulation of Trenslation Reveals Hidden Genetic Variation To Produce Complex Traits", Nature, 431: 184-187, 2004.
Tsang et al. "A Simple Chemical Method of Opening and Filling Carbon Nanotubes", Nature, 372: 159-162, 1994.
Tuite et al. "Propagation of Yeast Prions", Nature Reviews, 4: 878-889, 2003.

Vauthey et al. "Molecular Self-Assembly of Surfactant-Like Peptides to Form Nanotubes and Nanovesicles", Proc. Natl. Acad. Sci. USA, 99(8): 5355-5360, 2002.
Westwater et al. "Use of Genetically Engineered Phage to Deliver Antimicrobial Agents to Bacteria: an Alternative Therapy for Treatment of Bacterial Infections", Antimicrobial Agents and Chemotherapy, 47 (4): 1301-1307, 2003.
Yokoi et al. "Dynamic Reassembly of Peptide RADA16 Nanofiber Scaffold", Proc. Natl. Acad. Sci. USA, XP002446152, 102(24): 8414-8419, Jun. 2005.
Zhang "Fabrication of Novel Biomaterials Through Molecular Self-Assembly",.Nature Biotechnology, XP002305982, 21(10): 1171-1178, Oct. 1, 2003. pp. 1172-1173, p. 1173, Right col., p. 1174.
Zhang et al. "Design of Nanostructured Biological Materials Through Self-Assembly of Peptides and Proteins", Current Opinion in Chemical Biology, 6: 865-871, 2002.
Zhang et al. "Supramolecular Hydrogels Respond to Ligand-Receptor Interaction", Journal of the American Chemical Society, XP002421981, 125(45): 13680-13681, Nov. 12, 2003.
Zhao et al. "Fabrication of Molecular Materials Using Peptide Construction Motifs", Trends in Biotechnology, XP004552612, 22(9): 470-476, Sep. 1, 2004.
Communication Pursuant to Article 94(3) EPC Dated Jul. 13, 2011 From the European Patent Office Re.: Application No. 05747261.5.
Official Action Dated Jul. 15, 2011 From the US Patent and Trademark Office Re. U.S. Appl. No. 12/083,222.
Examination Report Dated Aug. 29, 2012 From the Government of India, Patent Office, Intellectual Property Building Re. Application No. 915/CHENP/2007.
Restriction Official Action Dated Jan. 25, 2012 From the US Patent and Trademark Office Re. U.S. Appl. No. 11/659,150.
Official Action Dated Jun. 11, 2012 From the US Patent and Trademark Office Re. U.S. Appl. No. 11/659,150.
Official Action Dated Mar. 29, 2013 From the US Patent and Trademark Office Re. U.S. Appl. No. 12/083,222.
Official Action Dated Feb. 8, 2013 From the US Patent and Trademark Office Re. U.S. Appl.No. 11/659,150.
Ex Parte Quayle Official Action Dated May 17, 2013 From the US Patent and Trademark Office Re. U.S. Appl. No. 11/659,150.
Official Action Dated Feb. 19, 2014 From the US Patent and Trademark Office Re. U.S. Appl. No. 13/671,667.
Communication Pursuant to Article 94(3) EPC Dated Dec. 16, 2013 From the European Patent Office Re. Application No. 05747261.5.
Official Action Dated Jan. 13, 2014 From the US Patent and Trademark Office Re. U.S. Appl. No. 12/083,222.
Official Action Dated May 30, 2014 From the US Patent and Trademark Office Re. U.S. Appl. No. 13/671,667.

* cited by examiner

SEQUENCE LISTING

```
<160> NUMBER OF SEQ ID NOS: 13

<210> SEQ ID NO 1
<211> LENGTH: 2
<212> TYPE: PRT
<213> ORGANISM: Artificial sequence
<220> FEATURE:
<223> OTHER INFORMATION: Synthetic peptide

<400> SEQUENCE: 1

Phe Phe
1

<210> SEQ ID NO 2
<211> LENGTH: 2
<212> TYPE: PRT
<213> ORGANISM: Artificial sequence
<220> FEATURE:
<223> OTHER INFORMATION: Synthetic peptide

<400> SEQUENCE: 2

Trp Trp
1

<210> SEQ ID NO 3
<211> LENGTH: 2
<212> TYPE: PRT
<213> ORGANISM: Artificial sequence
```

```
<220> FEATURE:
<223> OTHER INFORMATION: Synthetic peptide

<400> SEQUENCE: 3

Trp Tyr
1

<210> SEQ ID NO 4
<211> LENGTH: 2
<212> TYPE: PRT
<213> ORGANISM: Artificial sequence
<220> FEATURE:
<223> OTHER INFORMATION: Synthetic peptide

<400> SEQUENCE: 4

Trp Phe
1

<210> SEQ ID NO 5
<211> LENGTH: 2
<212> TYPE: PRT
<213> ORGANISM: Artificial sequence
<220> FEATURE:
<223> OTHER INFORMATION: Synthetic peptide

<400> SEQUENCE: 5

Phe Trp
1

<210> SEQ ID NO 6
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Phenylglycine

<400> SEQUENCE: 6

Xaa Xaa
1

<210> SEQ ID NO 7
<211> LENGTH: 3
<212> TYPE: PRT
<213> ORGANISM: Artificial sequence
<220> FEATURE:
<223> OTHER INFORMATION: Synthetic peptide

<400> SEQUENCE: 7

Cys Phe Phe
1

<210> SEQ ID NO 8
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D stereoisomer
```

```
<400> SEQUENCE: 8

Phe Phe
1

<210> SEQ ID NO 9
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: naphthylalanine

<400> SEQUENCE: 9

Xaa Xaa
1

<210> SEQ ID NO 10
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: pentafluro-phenylalanine

<400> SEQUENCE: 10

Xaa Xaa
1

<210> SEQ ID NO 11
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: iodo-phenylalanine

<400> SEQUENCE: 11

Xaa Xaa
1

<210> SEQ ID NO 12
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: 4-phenyl phenylalanine

<400> SEQUENCE: 12

Xaa Xaa
1

<210> SEQ ID NO 13
<211> LENGTH: 2
<212> TYPE: PRT
<213> ORGANISM: Artificial sequence
```

-continued

```
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: p-nitro-phenylalanine

<400> SEQUENCE: 13

Xaa Xaa
```

PEPTIDE NANOSTRUCTURES CONTAINING END-CAPPING MODIFIED PEPTIDES AND METHODS OF GENERATING AND USING THE SAME

RELATED APPLICATIONS

This Application is a divisional of U.S. patent application Ser. No. 11/662,136, filed on Mar. 8, 2007 which is a National Phase of PCT Patent Application No. PCT/IL2005/000954, having International Filing Date of Sep. 8, 2005, which claims the benefit of U.S. Provisional Patent Application No. 60/607,588 filed on Sep. 8, 2004. The contents of the above Applications are all incorporated herein by reference.

FIELD AND BACKGROUND OF THE INVENTION

The present invention relates to peptide nanostructures, articles, devices and methods of generating and using same.

Nanoscience is the science of small particles of materials and is one of the most important research frontiers in modern technology. These small particles are of interest from a fundamental point of view since they enable construction of materials and structures of well-defined properties. With the ability to precisely control material properties come new opportunities for technological and commercial development, and applications of nanoparticles have been shown or proposed in areas as diverse as micro- and nanoelectronics, nanofluidics, coatings and paints and biotechnology.

It is well established that future development of microelectronics, magnetic recording devices and chemical sensors will be achieved by increasing the packing density of device components. Traditionally, microscopic devices have been formed from larger objects, but as these products get smaller, below the micron level, this process becomes increasingly difficult. It is therefore appreciated that the opposite approach is to be employed, essentially, the building of microscopic devices from a molecular level up, primarily via objects of nanometric dimensions. Self-assembled nanoparticles, such as nanotubes and nanospheres, allow controlled fabrication of novel nanoscopic materials and devices. Such nanostrcutures have found use in areas as diverse as micro- and nanoelectronics, nanofluidics, coatings and paints and biotechnology.

In particular, wire-like semiconducting nanostructures. Most have attracted extensive interest over the past decade due to their great potential for addressing some basic issues about dimensionality and space confined transport phenomena as well as related applications. Wire-like semiconducting nanostructures often have distinctive properties and can be used as transparent conducting materials and gas sensors. For example, fluorine-doped tin oxide films are used in architectural glass applications because of their low emissivity for thermal infrared heat. Tin-doped indium oxide films can be used for flat panel displays due to their high electrical conductivity and high optical transparency.

In the field of magnetic recording, wire-like nanostructures can be used as magnetoresistive read transducers. It has been well known that the magnetoresistive sensors are capable of reading information from the surface of magnetic recording media at high linear densities. The magnetoresistive sensors sense magnetic signals by way of the electrical resistance change of magnetoresistive elements that varies as a function of the strength and orientation of the magnetic flux sensed by read or magnetoresistive elements. The use of nanoscale elements in such sensors significantly increases the capability of retrieving accurate information from highly dense magnetic media.

In the field of displays, much effort has been devoted to developed electrophoretic displays. Such displays use a display medium comprising a plurality of electrically charged particles suspended in a fluid. Electrodes are provided adjacent the display medium so that the charged particles can be moved through the fluid by applying an electric field to the medium. In one type of such electrophoretic display, the medium comprises a single type of particle having one optical characteristic in a fluid which has a different optical characteristic. In a second type of such electrophoretic display, the medium contains two different types of particles differing in at least one optical characteristic and in electrophoretic mobility.

Numerous configurations have been proposed and applied for the construction of nanostructures. The most widely used building blocks of nano-materials and nano-devices are the fullerene carbon nanotubes. Two major forms of carbon nanotubes exist, single-walled nanotubes (SWNT), which can be considered as long wrapped graphene sheets and multi walled nanotubes (MWNT) which can be considered as a collection of concentric SWNTs with different diameters.

SWNTs have a typical length to diameter ratio of about 1000 and as such are typically considered nearly one-dimensional. These nanotubes consist of two separate regions with different physical and chemical properties. A first such region is the side wall of the tube and a second region is the end cap of the tube. The end cap structure is similar to a derived from smaller fullerene, such as $C_{60}$.

Carbon nanotubes produced to date suffer from major structural limitations. Structural deviations including Y branches, T branches or SWNT junctions, are frequent results of currently used synthesis processes. Though such deviations in structure can be introduced in a "controlled" manner under specific conditions, frequent uncontrollable insertion of such defects result in spatial structures with unpredictable electronic, molecular and structural properties.

Other well-studied nanostructures are lipid surfactant nanomaterials (e.g., diacetylene lipids) which self-assemble into well-ordered nanotubes and other bilayer assemblies in water and aqueous solution [Yager (1984) Mol. Cryst. Liq. Cryst. 106:371-381; Schnur (1993) Science 262:1669-1676; Selinger (2001) J. Phys. Chem. B 105:7157-7169]. One proposed application of lipid tubules is as vehicles for controlled drug release. Accordingly, such tubes coated with metallic copper and loaded with antibiotics were used to prevent marine fouling.

Although lipid-based nanotubules are simple in form, lipid structures are mechanically weak and difficult to modify and functionalize, thus restricting their range of applications.

Material sciences involve the understanding of material characteristics as well as the development of new materials. Industrial and academic needs encourage material scientists to develop new materials having superior mechanical, electrical, optical and/or magnetic properties for many applications. Modern material sciences focus on the investigation of polymers, ceramics and semiconductors in many fluidic as well as solid forms including fibers, thin films, material bulks and the like.

Various manufacturing processes are known in the art for making synthetic fibers. Many synthetic fibers are produced by extrusion processes, in which a thick viscous liquid polymer precursor or composition is forced through one or more tiny holes of a spinneret to form continuous filaments of semi-solid polymer. As the filaments emerge from the holes of a spinneret, the liquid polymer converts first to a rubbery state which then is solidified. The process of extruding and solidifying filaments is generally known as spinning.

Wet spinning processes are typically employed with fiber-forming substances that have been dissolved in a solvent. Wet spinning techniques are preferred for spinning of high molecular weight polyamides. The spinnerets forming the filaments are submerged in a wet chemical bath, and as the filaments of the fiber-forming substances emerge from the spinnerets, they are induced to precipitate out of the solution and solidify.

In gel spinning, the polymer is not in a true liquid state during extrusion. The polymer chains are bound together at various points in liquid crystal form. This produces strong inter-chain forces in the resulting filaments that can significantly increase the tensile strength of the fibers. In addition, the liquid crystals are aligned along the fiber axis by the shear forces during extrusion. The filaments emerge with high degree of orientation relative to each other, further enhancing the strength. Typically, in gel spinning, the filaments first pass through air and then cooled in a liquid bath.

In dry spinning, the polymer is dissolved in a volatile solvent and the solution is pumped through the spinneret. As the fibers exit the spinneret, air is used to evaporate the solvent such that the fibers solidify and can be collected on a take-up wheel.

In melt spinning the polymer is melted and pumped through the spinneret. The molten fibers are cooled, solidified, and collected on a take-up wheel. Stretching of the fibers in both the molten and solid states provides for orientation of the polymer chains along the fiber axis.

Dispersion spinning is typically employed when the polymer having and infusible, insoluble and generally intractable characteristics. In this technique, the polymer is dispersed as fine particles in a chemical carrier that permit extrusion into fiber. The dispersed polymer is then caused to coalesce by a heating process and the carrier is removed by a thermal or chemical procedure.

Reaction spinning processes involve the formation of filaments from pre-polymers and monomers. The pre-polymers and monomers are further polymerized and cross-linked after the filament is formed. The reaction spinning process begins with the preparation of a viscous spinning solution, which is prepared by dissolving a low molecular weight polymer in a suitable solvent and a reactant. The spinning solution is then forced through the spinneret into a solution or being combined with a third reactant. The primary distinguishable characteristic of reaction spinning processes is that the final cross-linking between the polymer molecule chains in the filament occurs after the fibers have been spun. Post-spinning steps typically include drying and lubrication.

In tack spinning, a polymeric material in a tacky state is interposed between a foundation layer and a temporary anchorage surface. Being in a tacky state, the polymeric material adheres to the foundation layer and the temporary anchorage surface. The foundation layer is then separated from the temporary anchorage surface to produce fibers of the polymeric material. The fibers are hardened by thermal or chemical treatment, and separated from the temporary anchorage surface.

In electrospinning, a fine stream or jet of liquid is produced by pulling a small amount of charged liquefied polymer through space using electrical forces. The produced fibers are hardened and collected on a suitably located precipitation device to form a nonwoven article. In the case of a liquefied polymer which is normally solid at room temperature, the hardening procedure may be mere cooling; however other procedures such as chemical hardening or evaporation of solvent may also be employed.

Other processes for manufacturing polymeric articles include film blowing and injection molding.

In film blowing, an extruder is used to melt the polymer and pump it into a tubular die. Air blown into the center of the tube causes the melt to expand in the radial direction. The melt in thus extended in both radial and down-stream direction. The formed film is then collected by an arrangement of rollers.

In injection molding, a reciprocating or rotating screw both melts polymer pellets and provides the pressure required to inject the melt into a cold mold. The cold mold provides the article the desired shape.

In the area of thin film production, a well-known method for producing and depositing monolayers is the Langmuir-Blodgett method. In this method a monolayer of amphiphilic molecules is formed at the surface of a tank filled with a liquid sub-phase such as water. Amphiphilic molecules are those having a hydrophobic first end and a hydrophilic second end lined up side by side in a particular direction. In the Langmuir-Blodgett method, a solution of amphiphilic molecules dissolved in a solvent which is not miscible with the sub-phase liquid in the tank is spread onto the liquid surface. When the solvent evaporates, a loosely packed monolayer is formed on the surface of the sub-phase. A transition of the monolayer thus formed from a state of gas or liquid to a solid state is then achieved by compressing surface area of the layer to a predetermined surface pressure. The resulting monolayer is deposited onto the surface of a substrate by passing the substrate through the compressed layer while maintaining the layer at a predetermined surface pressure during the period of deposition.

Another method for producing a monolayer is known as self-assembling of molecules. In this method, a monolayer film is generated as a result of adsorption and bonding of suitable molecules (e.g., fatty acids, organic silicon molecules or organic phosphoric molecules) on a suitable substrate surface. The method typically involves solution deposition chemistry in the presence of water.

Over the years, extensive efforts were made to develop row materials which can be used for manufacturing fiber and films by the above techniques to provide articles having enhanced and/or application-specific characteristics. For example, one of the most studied natural fibrillar system is silk [Kaplan D L, "Fibrous proteins—silk as a model system," Polymer degradation and stability, 59:25-32, 1998]. There are many forms of silk, of which spider silk of *Nephila clavipas* (the golden orb weaver) is regarded as nature's high performance fiber, with a remarkable combination of strength, flexibility, and toughness. Although assembled by non-covalent interactions, silk is stronger than steel per given fibrillar diameter but, at the same time, is much more flexible. Due to its superior mechanical properties, the spider silk can be used in many areas requiring the combination of high mechanical strength with biodegradability, e.g., in tissue engineering applications [Kubik S., "High-Performance Fibers from Spider Silk," Angewandte Chemie International Edition, 41:2721-2723, 2002].

A known method of synthesizing spider silk material includes the introduction of a spider silk gene into a heterologous gene expression system and the secretion of spider silk protein therefrom. The protein is then processed, typically by electrospinning, to produce a fiber of enhanced mechanical properties [Jin H J, Fridrikh S V, Rutledge G C and Kaplan D L, "Electrospinning *Bombyx mori* silk with poly(ethylene oxide)," Biomacromolecules, 3:1233-1239, 2002].

Recently, electrospinning has been employed to fabricate virus-based composite fibers hence to mimic the spinning process of silk spiders [Lee S and Belcher A M, "Virus-Based Fabrication of Micro- and Nanofibers Using Electrospinning," Nano letters, 4:388-390, 2004]. In this study, M13 virus was genetically modified to bind conductive and semiconductor materials, and was thereafter subjected to an electrospinning process to provide conductive and semiconductor fibers.

Other than synthesized spider silk, the electrospinning process can be applied on a diversity of polymers including polyamides, polyactides and water soluble polymer such as polyethyleneoxide [Huang Z M, Zhang Y Z, Kotaki M and Ramakrishna S., "A review on polymer nanofibers by electrospinning and their applications in nanocomposites," Composites Science and technology, 63:2223-2253, 2003]. Heretofore, about 50 types of polymers have been successfully electrospun.

Electrospinning has also been used with carbon nanotubes to obtain super-tough carbon-nanotube fibers [Dalton A B et al., "Super-tough carbon-nanotube fibers—These extraordinary composite fibers can be woven into electronic textiles," Nature, 423:703, 2003]. By modifying a familiar method for carbon nanotubes fibers [Vigolo et al., "Macroscopic Fibers and Ribbons of Oriented Carbon Nanotubes," Science, 17:1331-1334, 2000] the researchers were able to spin a reel of nanotube gel fiber and then convert it into 100 m length of solid nanotube composite fiber. The resulting fibers were tougher than any other known natural or synthetic organic fiber. However, carbon nanotubes in general and carbon-nanotube fibers in particular suffer from structural deviations. Although deviations in structure can be introduced in a "controlled" manner under specific conditions, frequent uncontrollable insertion of such defects result in spatial structures with unpredictable electronic, molecular and structural properties. In addition, the production process of carbon nanotubes is very expensive and presently stands hundreds of U.S. dollars per gram.

Recently, peptide building blocks have been shown to form nanotubes. Peptide-based nanotubular structures have been made through stacking of cyclic D-, L-peptide subunits. These peptides self-assemble through hydrogen-bonding interactions into nanotubules, which in-turn self-assemble into ordered parallel arrays of nanotubes. The number of amino acids in the ring determines the inside diameter of the nanotubes obtained. Such nanotubes have been shown to form transmembrane channels capable of transporting ions and small molecules [Ghadiri, M. R. et al., Nature 366, 324-327 (1993); Ghadiri, M. R. et al., Nature 369, 301-304 (1994); Bong, D. T. et al., Angew. Chem. Int. Ed. 40, 988-1011 (2001)].

More recently, the discovery of surfactant-like peptides that undergo spontaneous assembly to form nanotubes with a helical twist has been made. The monomers of these surfactant peptides, like lipids, have distinctive polar and non-polar portions. They are composed of 7-8 residues, approximately 2 nm in length when fully extended, and dimensionally similar to phospholipids found in cell membranes. Although the sequences of these peptides are diverse, they share a common chemical property, i.e., a hydrophobic tail and a hydrophilic head. These peptide nanotubes, like carbon and lipid nanotubes, also have a very high surface area to weight ratio. Molecular modeling of the peptide nanotubes suggests a possible structural organization [Vauthey (2002) Proc. Natl. Acad. Sci. USA 99:5355; Zhang (2002) Curr. Opin. Chem. Biol. 6:865]. Based on observation and calculation, it is proposed that the cylindrical subunits are formed from surfactant peptides that self-assemble into bilayers, where hydrophilic head groups remain exposed to the aqueous medium. Finally, the tubular arrays undergo self-assembly through non-covalent interactions that are widely found in surfactant and micelle structures and formation processes.

Peptide based bis(N-α-amido-glycyglycine)-1,7-heptane dicarboxylate molecules were also shown to be assembled into tubular structures [Matsui (2000) J. Phys. Chem. B 104: 3383].

When the crystal structure of di-phenylalanine peptides was determined, it was noted that hollow nanometric channels are formed within the framework of the macroscopic crystal [Gorbitz (2001) Chemistry 7(23):5153-9]. However, no individual nanotubes could be formed by crystallization, as the crystallization conditions used in this study included evaporation of an aqueous solution at 80° C. No formation of discrete nano-structures was reported under these conditions.

As mentioned hereinabove, peptide nanotubes contributed to a significant progress in the field of nanotechnology since such building blocks can be easily modified and used in numerous mechanical, electrical, chemical, optical and biotechnological systems.

The development of systems which include nanoscale components has been slowed by the unavailability of devices for sensing, measuring and analyzing with nanometer resolution. One class of devices that have found some use in nanotechnology applications are proximity probes of various types including those used in scanning tunneling microscopes, atomic force microscopes and magnetic force microscopes. While good progress has been made in controlling the position of the macroscopic probe to sub-angstrom accuracy and in designing sensitive detection schemes, the tip designs to date have a number of problems.

One such problem arises from changes in the properties of the tip as atoms move about on the tip, or as the tip acquires an atom or molecule from the object being imaged. Another difficulty with existing probe microscope tips is that they typically are pyramidal in shape, and that they are not able to penetrate small openings on the object being imaged. Moreover, existing probe microscopes often give false image information around sharp vertical discontinuities (e.g., steps) in the object being imaged, because the active portion of the tip may shift from the bottom atom to an atom on the tip's side.

An additional area in which nanoscience can play a role is related to heat transfer. Despite considerable previous research and development focusing on industrial heat transfer requirements, major improvements in cooling capabilities have been held back because of a fundamental limit in the heat transfer properties of conventional fluids. It is well known that materials in solid form have orders-of-magnitude larger thermal conductivities than those of fluids. Therefore, fluids containing suspended solid particles are expected to display significantly enhanced thermal conductivities relative to conventional heat transfer fluids.

Low thermal conductivity is a primary limitation in the development of energy-efficient heat transfer fluids required in many industrial applications. To overcome this limitation, a new class of heat transfer fluids called nanofluids has been developed by suspending nanocrystalline particles in liquids such as water, oil, or ethylene glycol. The resulting nanofluids possess extremely high thermal conductivities compared to the liquids without dispersed nanocrystalline particles. Excellent suspension properties are also observed, with no significant settling of nanocrystalline oxide particles occurring in stationary fluids over time periods longer than several days. Direct evaporation of copper nanoparticles into pump oil results in similar improvements in thermal conductivity compared to oxide-in-water systems, but importantly, requires far smaller concentrations of dispersed nanocrystalline powder.

Numerous theoretical and experimental studies of the effective thermal conductivity of dispersions containing particles have been conducted since Maxwell's theoretical work was published more than 100 years ago. However, all previous studies of the thermal conductivity of suspensions have been confined to those containing millimeter- or micron-sized particles. Maxwell's model shows that the effective thermal conductivity of suspensions containing spherical particles increases with the volume fraction of the solid particles. It is also known that the thermal conductivity of suspensions increases with the ratio of the surface area to volume of the particle. Since the surface area to volume ratio is 1000 times larger for particles with a 10 nm diameter than for particles with a 10 mm diameter, a much more dramatic improvement in effective thermal conductivity is expected as a result of decreasing the particle size in a solution than can obtained by altering the particle shapes of large particles.

Since nanotubes have relatively straight and narrow channels in their cores, it was initially suggested that these cavities may be filled with foreign materials to fabricate one dimensional nanowires. Early calculations suggested that strong capillary forces exist in nanotubes, which are sufficient to hold gases and fluids inside them [Pederson (1992) Phys. Rev. Lett. 69:2689]. The first experimental proof was provided by Pederson and co-workers, who showed filling and solidification of molten leaf inside nanotubes [Pederson (1992) Phys. Rev. Lett. 69:415]. Various other examples, concerning the filling of nanotubes with metallic and ceramic materials exist in the literature [Ajayan (1993) Nature 361:392; Tsang (1994) Nature 372:416; Dujardin (1994) 265:1850].

Despite high applicability, the process of filling carbon nanotubes is difficult and inefficient. Most commonly produced carbon nanotubes, are capped at least at one end of the tube and no method for efficiently opening and filling the carbon nanotubes with foreign material is known to date. For example, nanotube ends can be opened by post oxidation treatment in an oxygen atmosphere at high temperature. The major drawback of such a procedure is that the tube ends become filled with carbonaceous debris. As a consequent, filling the open-ended tubes after post oxidation with other material has proven difficult. Another problem with carbon nanotubes synthesized in inert gas arcs is the formation of highly defective tubes containing amorphous carbon deposits on both the inside surface and outside surface of the tubes and the presence of discontinuous graphite sheets. Furthermore, since carbon nanotubes are curved, wetting may prove difficult. Finally, since the internal cavity of SWNTs is very small, filling can be done only for a very limited number of materials.

Some of the limitations plaguing the carbon based nanostructures and those made from other inorganic composites do not exhibit themselves in the nanostructure made from peptides described above. Nevertheless, although at least some of the above-described peptides were shown to form open-ended nanotubes [Hartgerink (1996) J. Am. Cham. Soc. 118:43-50], these are composed of peptide building blocks, which are relatively long and as such are expensive and difficult to produce, or limited by heterogeneity of structures that are formed as bundles or networks rather than discrete nanoscale structures.

The self-assembled peptide nanostructures are well ordered assemblies of various shapes with persistence length on the order of micrometers. The formation of the peptide nanostructures is very efficient and the nanostructures solution is very homogeneous. Similar to carbon nanotubes, the peptide nanostructures are formed as individual entities. For industrial applications, the self-assembled peptide nanostructures are favored over carbon nanotubes and spider silk from standpoint of cost, production means and availability.

It is recognized that improved peptide nanotubes are natural candidates for performing the above and many other tasks in the field of nanotechnology.

There is thus a widely recognized need for, and it would be highly advantageous to have, hollow and fibrillar peptide nanostructure and macroscopic and microscopic articles thereof, which are devoid of the above limitations.

SUMMARY OF THE INVENTION

According to one aspect of the present invention there is provided a nanostructure composed of a plurality of peptides, wherein each peptide includes one or more aromatic amino acids and further wherein one or more of these peptides is an end-capping modified peptide.

According to further features in preferred embodiments of the invention described below, the end capping modified peptide comprises one or more end capping moieties selected from the group consisting of an aromatic end capping moiety and a non-aromatic end-capping moiety.

According to still further features in the described preferred embodiments the end-capping moiety comprises a labeling moiety.

According to still further features in the described preferred embodiments the labeling moiety is selected from the group consisting of a fluorescent moiety, a phosphorescent moiety, a radioactive moiety, a heavy metal cluster and a chromophore.

According to still further features in the described preferred embodiments the end capping moiety is an aromatic moiety and the nanostructure is a fibrillar nanostructure.

According to still further features in the described preferred embodiments the aromatic end capping moiety is selected from the group consisting of 9-fluorenylmethyloxycarbonyl (Fmoc) and benzyloxycarbonyl (Cbz).

According to still further features in the described preferred embodiments the end-capping moiety is a non-aromatic moiety and the nanostructure is a tubular or spherical nanostructure.

According to still further features in the described preferred embodiments the non-aromatic end capping moiety is selected from the group consisting of acetyl and tert-butoxycarbonyl (Boc).

According to still further features in the described preferred embodiments each peptide includes no more than four amino acid residues.

According to still further features in the described preferred embodiments the peptide is a polyaromatic peptide.

According to still further features in the described preferred embodiments the polyaromatic peptide is selected from the group consisting of a polyphenylalanine peptide, a polytryptophane peptide, a polytyrosine peptide, a non-natural derivative thereof and combinations thereof.

According to still further features in the described preferred embodiments the polyaromatic peptides are at least 30 amino acids in length.

According to still further features in the described preferred embodiments the polyaromatic peptide is a dipeptide.

According to still further features in the described preferred embodiments the dipeptide is a homodipeptide.

According to still further features in the described preferred embodiments the polyaromatic peptide includes one or more aromatic amino acid residues having an aromatic moiety selected from the group consisting of a substituted or unsubstituted naphthalenyl and a substituted or unsubstituted phenyl.

According to still further features in the described preferred embodiments the substituted phenyl is selected from the group consisting of pentafluoro phenyl, iodophenyl, biphenyl and nitrophenyl According to still further features in the described preferred embodiments the homodipeptide is selected from the group consisting of naphthylalanine-naphthylalanine dipeptide, (pentafluro-phenylalanine)-(pentafluro-phenylalanine) dipeptide, (iodo-phenylalanine)-(iodo-phenylalanine)dipeptide, (4-phenyl phenylalanine)-(4-phenyl phenylalanine) dipeptide and (p-nitro-phenylalanine)-(p-nitro-phenylalanine)dipeptide.

According to still further features in the described preferred embodiments the end-capping modified peptide has the general Formula I:

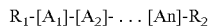 Formula I wherein:

n is an integer from 2 to 100;

$A_1, A_2, \ldots, A_n$ are each independently an amino acid residue, providing that one or more of $A_1, A_2, \ldots, A_n$ is an aromatic amino acid residue;

$R_1$ is selected from the group consisting of N-terminus amine and an N-terminus end-capping moiety; and $R_2$ is elected from the group consisting of C-terminus carboxylic acid and a C-terminus end-capping moiety, provided that one or more of $R_1$ and $R_2$ is an end capping moiety.

According to still further features in the described preferred embodiments the nanostructure does not exceed 500 nm in diameter.

According to still further features in the described preferred embodiments the nanostructure is being at least 1 nm in length.

According to still further features in preferred embodiments of this aspect, the nanostructure is stable at a temperature range of 4-200° C.

According to still further features in the described preferred embodiments the nanostructure is stable in an acidic environment.

According to still further features in the described preferred embodiments the nanostructure is stable in a basic environment.

According to another aspect of the present invention there is provided a method of generating the nanostructure described hereinabove, the method comprising incubating a plurality of peptides under conditions which favor formation of the nanostructure, wherein each of the peptides includes one or more aromatic amino acid and further wherein one or more of the peptides is an end capping modified peptide.

According to further features in preferred embodiments of the invention described below, the conditions which favor formation the nanostructure are selected from the group consisting of a solution type, concentration of the plurality of peptides, aggregation time, non-evaporating conditions and temperature.

According to yet another aspect of the present invention there is provided a composition comprising a material at least partially enclosed by the nanostructure described hereinabove.

According to still another aspect of the present invention there is provided a method of encapsulating a material in a nanostructure, the method comprising: (a) providing a nanostructure as described hereinabove, which has an internal cavity; and (b) introducing the material into the internal cavity of the nanostructure, thereby encapsulating the material in the nanostructure.

According to an additional aspect of the present invention there is provided a method of encapsulating a material in a nanostructure, the method comprising assembling the nanostructure described hereinabove in the presence of the material, thereby encapsulating the material in the nanostructure.

According to further features in preferred embodiments of the invention described below, the material is in a gaseous state.

According to still further features in the described preferred embodiments the material is in a condensed state.

According to still further features in the described preferred embodiments the material is selected from the group consisting of a conducting material, a semiconducting material, a thermoelectric material, a magnetic material, a light-emitting material, a biomolecule, a biomineral, a polymer and an organic material.

According to still further features in the described preferred embodiments the conducting material is selected from the group consisting of silver, gold, copper, platinum, nickel and palladium.

According to still further features in the described preferred embodiments the semiconducting material is selected from the group consisting of CdS, CdSe, ZnS and $SiO_2$.

According to still further features in the described preferred embodiments the magnetic material is a paramagnetic material.

According to still further features in the described preferred embodiments the paramagnetic material is selected from the group consisting of cobalt, copper, nickel and platinum.

According to still further features in the described preferred embodiments the magnetic material is a ferromagnetic material.

According to still further features in the described preferred embodiments the ferromagnetic material is selected from the group consisting of magnetite and NdFeB.

According to still further features in the described preferred embodiments the light-emitting material is selected from the group consisting of dysprosium, europium, terbium, ruthenium, thulium, neodymium, erbium, ytterbium and any organic complex thereof.

According to still further features in the described preferred embodiments the biomineral comprises calcium carbonate.

According to still further features in the described preferred embodiments the polymer is selected from the group consisting of polyethylene, polystyrene and polyvinyl chloride.

According to still further features in the described preferred embodiments the thermoelectric material is selected from the group consisting of bismuth telluride, bismuth selenide, bismuth antimony telluride and bismuth selenium telluride.

According to still further features in the described preferred embodiments the biomolecule is selected from the group consisting of a polynucleotide and a polypeptide.

According to yet an additional aspect of the present invention there is provided a composition comprising: (i) a nanostructure as described hereinabove; and (ii) an agent being attached to the nanostructure.

According to further features in preferred embodiments of the invention described below, the agent is entrapped within the nanostructure.

According to still further features in the described preferred embodiments the nanostructure is biodegradable.

According to still further features in the described preferred embodiments the agent is a drug, a nucleic acid molecule and/or a polypeptide.

According to still further features in the described preferred embodiments the agent is capable of being slowly released from the nanostructure.

According to still an additional aspect of the present invention there is provided a heat transfer device, comprising a nanofluid and a channel for holding the nanofluid, the nanofluid comprising nanostructures suspended in a fluid, wherein at least a portion of the nanostructures are the nanostructures resented hereinabove, the nanofluid and the channel being designed and constructed such that heat is carried by the nanostructures from a first end of the channel to a second end thereof.

According to still an additional aspect of the present invention there is provided a method of transferring heat, the method comprising: (a) providing a channel filled with a nanofluid comprising nanostructures suspended in a fluid, wherein at least a portion of the nanostructures are the nanostructures presented hereinabove; and (b) placing the channel in proximity to a heat source such that the nanofluid transfers heat from a first end of the channel to a second end thereof.

According to further features in preferred embodiments of the invention described below, the method and device further comprises a locomotion system for generating locomotion of the nanofluid within the channel.

According to still further features in the described preferred embodiments the channel is selected from the group consisting of a microchannel and a nanochannel.

According to still further features in the described preferred embodiments the method further comprises generating locomotion of the nanofluid within the channel.

According to still further features in the described preferred embodiments the nanostructure is coated by a conductive material.

According to a further aspect of the present invention there is provided a method of forming a fiber made of nanostructures, wherein each nanostructure is as described herein, the method comprising providing the nanostructures in solution, and fiberizing the solution thereby forming one or more fiber made of the nanostructures of the present invention.

According to further features in preferred embodiments of the invention described below, the fiberizing is effected by a process selected from a group consisting of an electrospinning process, a wet spinning process, a dry spinning process, a gel spinning process, a dispersion spinning process, a reaction spinning process and a tack spinning process.

According to yet a further aspect of the present invention there is provided a method of forming a film made of the nanostructures of the present embodiments, the method comprising: dissolving peptides in an organic solvent; adding a hydrophilic solvent to the organic solvent such that an interface is formed between the organic solvent and the hydrophilic solvent; and incubating the organic solvent and the hydrophilic solvent under conditions which allow the peptides to form a film of nanostructures in the interface. The peptides include one or more aromatic amino acids and at least one peptide is an end-capping modified peptide, as described herein.

According to further features in preferred embodiments of the invention described below, the organic solvent is an aromatic solvent.

According to still further features in the described preferred embodiments the aromatic solvent comprises benzene.

According to still further features in the described preferred embodiments the hydrophilic solvent is water.

According to still a further aspect of the present invention there is provided a fiber comprising the nanostructures presented herein, the fiber being at least 100 nm in length.

According to still a further aspect of the present invention there is provided a nonwoven article comprising electrospun fibers, wherein one or more of the electrospun fibers is the fiber of the previous aspect.

According to another aspect of the present invention there is provided a film comprising one or more layer of nanostructures, wherein each nanostructure is the nanostructure of the present invention, the thin film being at least 100 $nm^2$ in area size.

According to yet another aspect of the present invention there is provided a method of forming one or more layers of the nanostructures presented herein, the method comprising: placing the nanostructures in an organic solvent; applying one or more droplet of the organic solvent onto a surface of an hydrophilic solvent; and applying pressure, so as to form one or more layer of nanostructures on the surface of the hydrophilic solvent.

According to further features in preferred embodiments of the invention described below the method of forming one or more layer of nanostructures further comprises transferring the layer of the nanostructures to a substrate.

According to still further features in the described preferred embodiments transferring the layer of nanostructures to the substrate is effected by a technique selected from the group consisting of a Langmuir-Blodgett technique and a Langmuir-Schaeffer technique.

According to still another aspect of the present invention there is provided a method of forming an aligned array or film of the nanostructures presented herein, the method comprising: dissolving peptides in an organic solvent; applying the organic solvent on a substrate; and incubating the substrate and the organic solvent under conditions which allow the peptides to form an aligned array or a film of nanostructures on the substrate. Each of the peptides include at least one aromatic amino acid residue and at least one of the peptides is an end-capping modified peptide as described herein.

According to further features in preferred embodiments of the invention described below, the nanostructures are responsive to a magnetic field.

According to still further features in the described preferred embodiments the method further comprises subjecting the substrate to a magnetic field.

According to still further features in the described preferred embodiments the nanostructures are responsive to an electric field.

According to still further features in the described preferred embodiments the method further comprises subjecting the substrate to an electric field.

According to an additional aspect of the present invention there is provided a method of forming a fiber made of the nanostructures presented herein, the method comprising subjecting the nanostructures, in solution, to an electric field so as to form one or more fiber of the nanostructures.

According to further features in preferred embodiments of the invention described below, the method further comprises collecting the fiber on a precipitation electrode.

According to still further features in the described preferred embodiments collecting the fiber comprises rotating the precipitation electrode so as to wind the fiber around the precipitation electrode.

According to still further features in the described preferred embodiments collecting the fiber comprises moving the fiber relative to the precipitation electrode so as to provide a nonwoven mat of peptide nanostructures.

According to still further features in the described preferred embodiments the method further comprises unwinding the fiber of the peptide nanostructure off the precipitation electrode.

According to yet an additional aspect of the present invention there is provided a composition, comprising a polymer and a nanostructure according to the present embodiments.

According to further features in preferred embodiments of the invention described below, the nanostructure is coated by a conductive material.

According to still an additional aspect of the present invention there is provided a composition comprising a matrix and two or more of the nanostructures of the present embodiments dispersed throughout the matrix.

According to further features in preferred embodiments of this aspect, the matrix is selected from the group consisting of a metal matrix, a ceramic matrix and a polymeric matrix.

According to further features in preferred embodiments of the invention described below, the nanostructure is coated by a conductive material.

According to still further features in the described preferred embodiments the matrix is a two-dimensional matrix; preferably the matrix is a three-dimensional matrix.

According to a further aspect of the present invention there is provided a nanofluid comprising nanostructures suspended in a fluid, wherein at least a portion of the nanostructures comprises the nanostructures presented herein.

According to further features in preferred embodiments of the invention described below, the nanostructure is coated by a conductive material.

According to yet a further aspect of the present invention there is provided a composition for modulated delivery of a chemical to a predetermined location, the composition comprises: two or more nanoshells, the nanoshells having a nanostructure core surrounded by a conductive shell being capable of converting incident radiation into heat energy, the nanostructure core being the nanostructure presented herein; and a medium comprising the chemical and a thermally responsive material in thermal contact with the nanoshells.

According to further features in preferred embodiments of the invention described below, the incident radiation is selected from the group consisting of electromagnetic wave, an electric field, a magnetic field and an ultrasound wave.

According to still a further aspect of the present invention there is provided a method for inducing localized hyperthermia in a cell or tissue of an individual, the method comprises: delivering two or more nanoshells, each having a nanostructure core and a conductive shell and being capable of converting incident radiation into heat energy, the nanostructure core being the nanostructure presented herein; and exposing the nanoshells to the incident radiation to thereby convert the incident radiation into the heat energy.

According to further features in preferred embodiments of the invention described below, the conductive shell is a metal shell.

According to still further features in the described preferred embodiments the incident radiation is selected from the group consisting of electromagnetic wave, an electric field, a magnetic field and an ultrasound wave.

According to still further features in the described preferred embodiments the nanoshells comprise an affinity component having affinity to the cell or the tissue.

According to still further features in the described preferred embodiments the affinity component comprises a moiety selected from the group consisting of an antibody, an antigen, a ligand and a substrate.

According to another aspect of the present invention there is provided a field emitter device, comprising an electrode and the nanostructure of the present embodiments, the electrode and the nanostructure being designed and constructed such that when an electrical field is formed therebetween, electrons are emitted from the nanostructure.

According to another aspect of the present invention there is provided a method of emitting electrons, the method forming an electric field near the nanostructure of the present embodiments, such that electrons are emitted therefrom.

According to further features in preferred embodiments of the invention described below, the field emitter device further comprises a substrate having a fluorescent powder coating, the fluorescent powder coating being capable of emitting light upon activation by the electrons.

According to still further features in the described preferred embodiments the nanostructure is coated by a conductive material.

According to yet another aspect of the present invention there is provided a device for obtaining information from a nanoscale environment, the device comprises: (a) a nanostructure according to the present embodiments, which is capable of collecting signals from the nanoscale environment; and (b) a detection system capable of interfacing with the nanostructure and receiving the signals thus obtaining information from the nanoscale environment.

According to yet another aspect of the present invention there is provided a method of obtaining information from a nanoscale environment, the method comprises: (a) collecting signals from the nanoscale environment using the nanostructure of the present embodiments; and (b) receiving the signals from the nanostructure, thus obtaining information from the nanoscale environment.

According to further features in preferred embodiments of the invention described below, the device further comprises a supporting element onto which the nanostructure being mounted, wherein the supporting element is operable to physically scan the nanoscale environment.

According to still further features in the described preferred embodiments the nanostructure is adapted to collect near field light from the nanoscale environment.

According to still further features in the described preferred embodiments the detection system is capable of converting physical motion of the nanostructure to electric signals.

According to still further features in the described preferred embodiments the method further comprises physically scanning the nanoscale environment using the nanostructure.

According to still further features in the described preferred embodiments the information signals are selected from the group consisting of mechanical signals, optical signals, electrical signals, magnetic signals, and chemical signals.

According to still further features in the described preferred embodiments the information signals comprise near field light from the nanoscale environment.

According to still further features in the described preferred embodiments the method further comprises converting physical motion of the nanostructure to electric signals.

According to still further features in the described preferred embodiments the nanostructure is coated by a conductive material.

According to still another aspect of the present invention there is provided an apparatus for electron emission lithography, comprising: (a) an electron emission source being at a first electrical potential, the electron emission source including one or more nanostructure of the present invention; and (b) an electrically conducting mounting device being in a second electrical potential, the second electrical potential being different than the first electrical potential; wherein the difference between the second electrical potential and the first electrical potential is selected such that electrons are emitted from the electron emission source, and impinge on the mounting device to thereby perform a lithography process on a sample mounted on the mounting device.

According to still another aspect of the present invention there is provided a method of electron emission lithography, the method comprises: (a) using an electron emission source for emitting electrons, the electron emission source including one or more nanostructure of the present embodiments; and (b) collecting the electrons on an electrically conducting mounting device, thereby performing a lithography process on a sample mounted on the mounting device.

According to further features in preferred embodiments of the invention described below, the apparatus further comprises a magnetic field generator for generating a magnetic field, thereby to direct the electrons to a predetermined location on the sample.

According to still further features in the described preferred embodiments the method further comprises generating a magnetic field to thereby direct the electrons to a predetermined location on the sample.

According to still further features in the described preferred embodiments the nanostructure is coated by a conductive material.

According to an additional aspect of the present invention there is provided a memory cell, comprising: (a) an electrode; and (b) a nanostructure according to the present embodiments, which is capable of assuming one of at least two states; the nanostructure and the electrode being designed and constructed such that when electrical current flows through the electrode, the nanostructure transforms from a first state of the at least to states to a second state of the at least to states.

According to an additional aspect of the present invention there is provided a method of recording binary information, the binary information being composed of a first type of datum and a second type of datum, the method comprising using a plurality of nanostructures as described herein, each capable of assuming one of two states, wherein a first state of the two states correspond to the first type of datum and the second state of the two states correspond to the second type of datum.

According to further features in preferred embodiments of the invention described below, the transformation from the first state to the second state comprises a geometrical deflection of the nanostructure.

According to still further features in the described preferred embodiments the nanostructures are coated by a conductive material.

According to yet an additional aspect of the present invention there is provided a mechanical transmission device, comprising a first nanostructure and a second nanostructure, the first and the second nanostructure being operatively associated thereamongst such that a motion of the first nanostructure generates a motion of the second nanostructure, wherein one or more of the first and the second nanostructures is the nanostructure of the present embodiments.

According to yet an additional aspect of the present invention there is provided a method of transmitting mechanical motion, the method comprises: (a) providing a first nanostructure and a second nanostructure, one or more of the first and the second nanostructures is the nanostructure of the present embodiments; and (b) generating a motion of the first nanostructure such that the motion of the first nanostructure generates a motion of the second nanostructure.

According to further features in preferred embodiments of the invention described below, the first nanostructure and the second nanostructure are each independently coated by a conductive material.

According to still an additional aspect of the present invention there is provided a nanoscale mechanical device, comprising one or more nanostructures as presented herein, designed and configured for grabbing and/or manipulating nanoscale objects.

According to still an additional aspect of the present invention there is provided a method of grabbing and/or manipulating nanoscale objects, the method comprises: (a) providing one or more nanostructures according to the present embodiments; and (b) using the nanostructure for grabbing and/or manipulating the nanoscale objects.

According to further features in preferred embodiments of the invention described below, the first and second nanostructures are tubular nanostructures being capable of at least a constrained motion.

According to still further features in the described preferred embodiments the device further comprises a voltage source for generating electrostatic force between the first and the second tubular nanostructures, thereby to close or open the first and the second tubular nanostructures on the nanoscale object.

According to still further features in the described preferred embodiments the method further comprises generating electrostatic force between the first and the second tubular nanostructures, thereby closing or opening the first and the second tubular nanostructures on the nanoscale object.

According to still further features in the described preferred embodiments the nanostructure is coated by a conductive material.

According to a further aspect of the present invention there is provided an electronic switching or amplifying device comprising a source electrode, a drain electrode, a gate electrode and a channel, wherein one or more of the gate electrode and the channel comprises the nanostructure of the present invention.

According to a further aspect of the present invention there is provided an electronic inverter having a first switching device and a second switching device, each of the first switching device and the first switching device comprising a source electrode, a drain electrode, a gate electrode and a channel, such that the drain electrode of the first switching device is electrically communicating with the source electrode of the second switching device, wherein one or more of the gate electrode and the channel comprises the nanostructure of the present embodiments.

According to further features in preferred embodiments of the invention described below, the source electrode and the drain electrode are formed on a substrate.

According to still further features in the described preferred embodiments the substrate comprises a thermal oxide deposited over a silicon substrate.

According to still further features in the described preferred embodiments the nanostructure is coated by a conductive material.

According to yet a further aspect of the present invention there is provided an optical device comprising a waveguide core and the nanostructure of the present embodiments, wherein the nanostructure is being characterized by nonlinear optical properties and capable of manipulating light.

According to yet a further aspect of the present invention there is provided an optical filter comprising a thin film composed of one or more layers of the nanostructure presented herein.

According to further features in preferred embodiments of the invention described below, the nanostructures are responsive to electrical voltage in a manner such that when the electrical voltage is applied to the thin film, optical properties of the thin film are altered.

According to still a further aspect of the present invention there is provided an artificial tissue, comprising viable cells incorporated throughout a porous biocompatible matrix composed of one or more nanostructure, the one or more nanostructure is the nano structure of the present invention.

According to further features in preferred embodiments of the invention described below, the artificial tissue is used for surgery training and/or for implantation in a subject.

According to further features in preferred embodiments of the invention described below, the matrix is selected from the group consisting of a two-dimensional matrix and a three-dimensional matrix.

The present invention successfully addresses the shortcomings of the presently known configurations by providing nanostructures made of end-capping modified peptides, in which various morphological, electrical, physical and chemical properties can be finely controlled.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a", "an" and "the" include plural references unless the context clearly dictates otherwise. For example, the term "a nanostructure" or "at least one nanostructure" may include a plurality of nanostructures, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the term "comprising" means that other steps and ingredients that do not affect the final result can be added. This term encompasses the terms "consisting of" and "consisting essentially of".

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
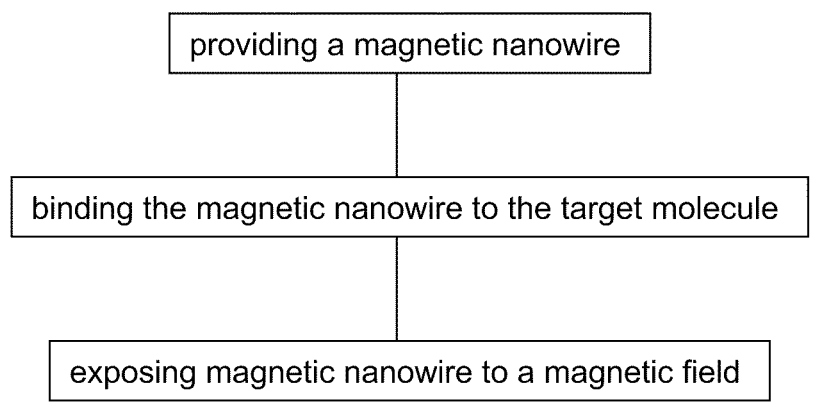
FIG. 1 is a flowchart diagram presenting a method of positioning a target molecule at a predetermined location, according to a preferred embodiment of the present invention, by means of a magnetic nanowire, according to a preferred embodiment of the present invention, bound to the target molecule and of a magnetic field.

The present invention is of nanostructures made of peptides having an aromatic amino acid residue, whereby one or more peptides in the nanostructure is end-capping modified. The present invention is further of methods of generating such nanostructures and of uses thereof in various applications, such as, but not limited to, encapsulation of foreign materials such as pharmaceutically active agents; formation of articles and devices such as nanowires, field effect transistors, field emitters, bipolar transistors, complementary inverters, tunnel diodes, light emitting diodes, optical filters and waveguides, sensors, display systems and devices, memory chips, cooling systems, nano-mechanical devices; and fabrication of thin films and fibers. The present invention is further of uses of these peptide nanostructures in medical and biological applications, such as, but not limited to, drug delivery, tissue engineering, biosensors, molecule monitoring and locomotion, nucleic acid sequencing and the like.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Self-assembled nanostructures allow controlled fabrication of novel nanoscopic materials and devices. Nanotubular structures are particularly important structural elements as they may serve in numerous applications, for example, as nanowires and nanoscaffolds. Most widely used nanotubes are made of carbon or peptide assemblers (i.e., building blocks). While carbon nanotubes suffer from major structural defects including branching and bending resulting in spatial structures with unpredictable electronic, molecular and structural properties, peptide nanotubes such as those composed of surfactant like peptides and cyclic D-, L-peptide subunits form crystals, networks, or bundles of nanostructures and thus can not be used in the above-described applications.

The present inventors have previously uncovered that aromatic peptides (e.g., diphenylalanine) are capable of forming planar, tubular and spherical nanostructures, which can be used in numerous mechanical, electrical, chemical, optical and biotechnological systems (see, for example, WO 2004/052773, WO 2004/060791, PCT/IL2005/000589 and U.S. patent application Ser. Nos. 11/148,262 and 11/148,266, which are all incorporated by reference as if fully set forth herein).

The present inventors have further uncovered that the tubular and spherical nanostructures can encapsulate, or be formed so as to encapsulate, various materials such as gaseous or condense materials. Furthermore, the present inventors have uncovered that once encapsulated a solid material can be exposed by removal of the peptide nanostructure sheath by, for example, enzymatic digestion, thereby obtaining a nano-object such as, for example, a nanowire. Further still, the present inventors have uncovered that macroscopic fibers, layers and arrays can be produced from peptide nanostructure in a variety of methods and techniques.

While trying to modulate the electrostatic interactions between the peptides composing such nanostructures, the present inventors have utilized end-capping modified peptides for forming the nanostructures. The present inventors have uncovered that (i) such a modification does not affect the formation of the nanostructure; (ii) the overall charge of the peptide, and therefore of the resulting nanostructure, can be turned positive, negative of nullified; and (iii) by modulating the chemical structure of the end-capping moiety of the modified peptides, features such as the shape and chemical or physical properties of the nanostructure can be controlled.

While further reducing the present invention to practice, the present inventors have produced a variety of nanostructures from a variety of end-capping modified peptides, and have shown that the morphology of the nanostructure, e.g. tubular, spherical or fibrillar, was induced by the choice of the end-capping modifications.

Thus, according to one aspect of the present invention, there is provided a nanostructure composed of a plurality of peptides, whereby each peptide includes at least one aromatic amino acid, and further whereby one or more peptides are end-capping modified peptides.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

The phrase "end-capping modified peptide", as used herein, refers to a peptide which has been modified at the N-(amine) terminus and/or the C-(carboxyl) terminus thereof. The end-capping modification refers to the attachment of a chemical moiety to the terminus, so as to form a cap. Such a chemical moiety is referred to herein as an end capping moiety and is typically also referred to herein and in the art, interchangeably, as a peptide protecting moiety or group.

According to the present invention, at least one of the peptides which are used to form the nanostructures of the present invention, is modified by an end capping modification, as described hereinabove.

The phrase "end-capping moiety", as used herein, refers to a moiety that when attached to the terminus of the peptide, modifies the end-capping. The end-capping modification typically results in masking the charge of the peptide terminus, and/or altering chemical features thereof, such as, hydrophobicity, hydrophilicty, reactivity, solubility and the like. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

Representative examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denote d herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

Representative examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

Other end-capping modifications of peptides include replacement of the amine and/or carboxyl with a different moiety, such as hydroxyl, thiol, halide, alkyl, aryl, alkoxy, aryloxy and the like, as these terms are defined hereinbelow.

In a preferred embodiment of the present invention, all of the peptides composing the nanostructure are end-capping modified. In one embodiment, the peptides are modified only at the N-termini or the C-termini thereof, resulting in a nanostructure that has a negative net charge or a positive net charge, respectively. In another embodiment, the peptides are modified at both the N-termini and the C-termini, resulting in an uncharged nanostructure.

Other combination of N-terminus end capping and C-terminus end capping of the various peptides composing the nanostructure are also included in the scope of the present invention. These include, for example, the presence of certain percents of end-capping modified peptides, whereby the peptides are modified at the N-termini and/or the C-termini.

As mentioned above, the end-capping modification changes the structure of the end-capping of the peptide, changing its chemical and physical properties and therefore changing the chemical and physical properties of the peptide and the chemical and physical properties of the resulting nanostructure. Using such end-capping modification, nanostructures in which these properties are finely controlled can be formed and hence, controlled fabrication of e.g., films, monolayer, or other macroscopic structures with nano-scale order is allowed.

One such physical property of an end-capping of a peptide is the charge of the end-capping, which when unmodified, is positive at the N-terminus end-capping at neutral pH and lower, and negative at the C-terminus at neutral pH and higher. Changing the charge of one or both of the end-capping of one or more of the peptides may result in altering the morphology of the resulting nanostructure and/or the way the resulting nanostructure responds to, for example, an electric and/or magnetic fields.

Having the overall charge of the nanostructure altered and therefore rendering the nanostructure polar or non-polar, and hence susceptible or unsusceptible to electric and magnetic fields, opens a wide range of possibilities for applications requiring a polar or a non-polar nanostructure or object, such as discussed hereinbelow. Hence, end capping modification of the peptides the net charge of the nanostructure can be finely controlled.

Another chemical property of an end-capping of a peptide is its hydrophobic/hydrophilic nature, which when unmodified, is hydrophilic in peptides. Altering the hydrophobic/hydrophilic property of one or both of the end-capping of the peptide may result, for example, in altering the morphology of the resulting nanostructure and/or the aqueous solubility thereof. By selecting the percentage of the end-capping modified peptides and the nature of the end capping modification, the hydrophobicity/hydrophilicity, as well as the solubility of the nanostructure can be finely controlled. Such finely controlled nanostructures can be beneficially used in is various applications such as functional surfaces, nano-catalysis, formation of macroscopic objects with nano-scale order, biosensors, Composite materials, and tissue engineering. Another chemical property of an end-capping of a peptide is its aromatic nature, which when unmodified is null.

While reducing the present invention to practice, the present inventors have uncovered that modifying the end-capping of a peptide does not abolish its capacity to self-assemble into nanostructures, similar to the nanostructures formed by unmodified peptides, as demonstrated in the Examples section that follows. The persistence of the end-capping modified peptides to form nanostructures supports the hypothesis of the present inventors according to which the dominating characteristic required to form peptides nanostructures is the aromaticity of its side-chains, and the it-stacking interactions induced thereby, as previously described in, for example WO 2004/052773 and WO 2004/060791.

While further reducing the present invention to practice, the present inventors surprisingly found that altering the aromatic nature of at least one of the end-capping of the peptide affects the morphology of the resulting nanostructure. As demonstrated in the Examples section that follows, it was found that under the same conditions where an unmodified peptide or a peptide modified with a non-aromatic end-capping moiety self-assembles to a tubular or spherical nanostructure, peptides modified with an aromatic end-capping moiety self-assembles to a fibrillar nanostructure. The formation of fibrillar nanostructures was particularly observed while utilizing peptides modified by an aromatic moiety at the N-terminus thereof. It was further surprisingly found that such fibrillar nanostructures are formed even when peptides as short as dipeptides where used to form the nanostructure. The formation of a fibrillar peptide nanostructure, and particularly the formation of such nanostructures from short peptides, has never been described hitherto. Without being bound by any particular theory it is suggested that fibrillar structures are formed by aromatic moieties capping the N-terminus of the peptides.

As is further demonstrated and discussed in the Examples section that follows, it was further found that the nature of the end-capping moiety affects the molecular conformation of the peptide nanostructure.

Thus, according to an embodiment of the present invention, one or more of the peptides is modified by one or more non-aromatic end capping moiety.

According to another embodiment, all of the peptides are modified by one or more non-aromatic end-capping moiety. The nanostructure composed of such peptides typically adopts a tubular or spherical shape.

Representative examples of non-aromatic end capping moieties suitable for N-terminus modification include, without limitation, formyl, acetyl trifluoroacetyl, tert-butoxycarbonyl, trimethylsilyl, and 2-trimethylsilyl-ethanesulfonyl. Representative examples of non-aromatic end capping moieties suitable for C-terminus modification include, without limitation, amides, allyloxycarbonyl, trialkylsilyl ethers and allyl ethers.

According to another embodiment of the present invention, one or more of the peptides is modified by an aromatic end capping moiety.

According to another embodiment, all of the peptides are modified by one or more aromatic end-capping moiety. The nanostructure composed of such peptides typically adopts a fibrillar shape.

Representative examples of aromatic end capping moieties suitable for N-terminus modification include, without limitation, fluorenylmethyloxycarbonyl (Fmoc). Representative examples of non-aromatic end capping moieties suitable for C-terminus modification include, without limitation, benzyl, benzyloxycarbonyl (Cbz), trityl and substituted trityl groups.

Thus, in one embodiment of the present invention, the end-capping modified peptides are modified by an aromatic and not by a non-aromatic (e.g., Boc) end-capping moiety.

As used herein the phrase "tubular or spherical nanostructure" refers to a spherical or elongated tubular or conical structure having a diameter or a cross-section of less than 1 μm (preferably less than 500 nm, and more preferably less than about 100 nm,). The length of the tubular nanostructure of the present invention is preferably at least 1 μm, more preferably at least 10 nm, even more preferably at least 100 nm and even more preferably at least 500 nm. Further preferably, the tubular nanostructure described herein is hollowed. It will be appreciated, though, that the tubular structure of the present invention can be of infinite length (i.e., macroscopic fibrous structures) and as such can be used in the fabrication of hyper-strong materials.

As used herein the phrase "fibrillar nanostructure" refers to a filament or fiber having a diameter or a cross-section of less than 1 μm (preferably less than about 100 nm, more preferably less than about 50 nm, and even more preferably less than about 10 nm). The length of the fibrillar nanostructure of the present invention is preferably at least 1 μm, more preferably at least 10 nm, even more preferably at least 100 nm and even more preferably at least 500 nm. It will be appreciated, though, that the fibrillar structure of the present invention can be of infinite length (i.e., macroscopic fibrous structures) and as such can be used in the fabrication of hyper-strong materials. Preferably, the fibrillar nanostructures described herein are characterized as non-hollowed or at least as having a very fine hollow.

The end-capping modified peptides utilized according the present embodiments can be collectively represented by the following general Formula I:

$$R_1-[A_1]-[A_2]-\ldots[A_n]-R_2 \qquad \text{Formula I}$$

wherein:

n is an integer from 2 to 100;

$A_1, A_2, \ldots, A_n$ are each independently an amino acid residue as this term is defined hereinbelow, providing that at least one of said $A_1, A_2, \ldots, A_n$ is an aromatic amino acid residue as this term is defined hereinbelow;

$R_1$ is an N-terminus end-capping moiety or absent; and $R_2$ is a C-terminus end-capping moiety or absent, providing that at least one of $R_1$ and $R_2$ is present.

As used herein throughout, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| isoleucine | Iie | I |
| Leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |

TABLE 2-continued

| Non-conventional amino acid | Code | Non-conventional amino acid | Code |
|---|---|---|---|
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhphe |
|  | Nnbhm | N-(N-(3,3-diphenylpropyl) | Nnbhe |
| N-(N-(2,2-diphenylethyl) carbamylmethyl-glycine | Nnbhm | carbamylmethyl(1)glycine |  |
| 1-carboxy-1-(2,2-diphenyl ethylamino)cyclopropane | Nmbc |  |  |

Natural aromatic amino acids, Trp, Tyr and Phe, may be substituted for synthetic unnatural acid such as phenylglycine, TIC, naphthylalanine (Nal), ring-methylated derivatives of Phe, halogenated derivatives of Phe or O-methyl-Tyr, and β amino-acids.

In addition to the above, the peptides of the present invention may also include one or more modified amino acids (e.g., biotinylated amino acids) or one or more non-amino acid monomers (e.g. fatty acids, complex carbohydrates etc).

The peptides used for forming the nanostructures described herein preferably has at least two amino acid residues and can include up to 100 amino acid residues, provided that at least one amino acid residue in each of the peptides is of an aromatic amino acid.

In one preferred embodiment, each of the peptides includes no more than 4 amino acid residues.

In another preferred embodiment, each of the peptides is a polyaromatic peptide.

In yet another preferred embodiment, each polyaromatic peptide comprises 30 amino acid residues and more.

In still another preferred embodiment, each peptide comprises two amino acid residues and therefore the nanostructure is formed from a plurality of dipeptides.

According to a preferred embodiment of this aspect of the present invention the peptide is a dipeptide or a tripeptide such as set forth in SEQ ID NO: 1, 5, 6, 7 or 8.

Preferably, each of the dipeptides is a homodipeptide and more preferably, it is a homodipeptide that comprises two aromatic amino acid residues.

As used herein the phrase "polyaromatic peptides" refers to end-capping modified peptides which include at least 80%, at least 85% at least 90%, at least 95% or more, say 100% aromatic amino acid residues. These end-capping modified peptides can be homogenic, for example, end-capping modified polyphenylalanine, end-capping modified polyphenylalanine peptides, end-capping modified polytriptophane peptides, end-capping modified polytyrosine peptides, non-natural derivatives thereof and combinations thereof. These end-capping modified peptides may be heterogenic of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100 amino acids.

The phrase "aromatic amino acid residue", as used herein, refers to an amino acid residue having an aromatic moiety for a side-chain, such as, for example, a substituted or unsubstituted naphthalenyl and substituted or unsubstituted phenyl. The substituted phenyl may be, for example, pentafluoro phenyl, iodophenyl, biphenyl and nitrophenyl.

According to a preferred embodiment of the present invention, the end-capping modified polyaromatic peptides are dipeptides, i.e., having two amino acid residues, and according to another preferred embodiment, the end-capping modified dipeptides is a homodipeptides, having two amino acid residues which are identical with respect to their side-chains residue.

Representative examples of such end-capping modified homodipeptides include, without limitation, an end-capping modified naphthylalanine-naphthylalanine (Nal-Nal) dipeptides (SEQ ID NO: 9), end-capping modified (pentafluro-phenylalanine)-(pentafluro-phenylalanine)dipeptides (SEQ ID NO: 10), end-capping modified (iodo-phenylalanine)-(iodo-phenylalanine) (SEQ ID NO: 11), end-capping modified (4-phenyl phenylalanine)-(4-phenyl phenylalanine) (SEQ ID NO: 12) and end-capping modified (p-nitro-phenylalanine)-(p-nitro-phenylalanine) (SEQ ID NO: 13).

Thus, also contemplated are homodipeptides, and more preferably aromatic homodipeptides in which each of the amino acids comprises an aromatic moiety, such as, but not limited to, substituted or unsubstituted naphthalenyl and substituted or unsubstituted phenyl. The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine When substituted, the phenyl, naphthalenyl or any other aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

As used herein, the term "alkyl" refers to a saturated aliphatic hydrocarbon including straight chain and branched chain groups. Preferably, the alkyl group has 1 to 20 carbon atoms. The alkyl group may be substituted or unsubstituted. When substituted, the substituent group can be, for example, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Representative examples are piperidine, piperazine, tetrahydro furane, tetrahydropyrane, morpholino and the like.

A "hydroxy" group refers to an —OH group.

A "thio", "thiol" or "thiohydroxy" group refers to and —SH group.

An "azide" group refers to a —N═N≡N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to and —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "halo" or "halide" group refers to fluorine, chlorine, bromine or iodine.

A "trihaloalkyl" group refers to an alkyl substituted by three halo groups, as defined herein. A representative example is trihalomethyl.

An "amino" group refers to an —NR'R" group where R' and R" are hydrogen, alkyl, cycloalkyl or aryl.

A "nitro" group refers to an —NO$_2$ group.

A "cyano" group refers to a —C≡N group.

The nanostructures of the present invention can be generated from linear or cyclic peptides (e.g., cyclic di-peptides of phenylalanine, see Example 1 in the Examples section that follows).

Cyclic peptides constitute a unique end-capping modified peptide as the modification may be the cyclizing bond (between the amine of the N-terminus and the carboxyl of the C-terminus), and can either be synthesized in a cyclic form or configured so as to assume a cyclic form under desired conditions (e.g., physiological conditions).

For example, a peptide according to the teachings of the present invention can include at least two cysteine residues flanking the core peptide sequence. In this case, cyclization can be generated via formation of S—S bonds between the two Cys residues. Side-chain to side chain cyclization can also be generated via formation of an interaction bond of the formula —(—CH$_2$-)n-S—CH$_2$—C—, wherein n=1 or 2, which is possible, for example, through incorporation of Cys or homoCys and reaction of its free SH group with, e.g., bromoacetylated Lys, Orn, Dab or Dap. Furthermore, cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)n-COOH)—C(R)H—COOH or H—N((CH$_2$)n-COOH)—C(R)H—NH$_2$, wherein n=1-4, and further wherein R is any natural or unnatural side chain of an amino acid.

The end-capping modification of the peptides forming the nanostructures described herein can be further utilized for incorporating into the nanostructure a labeling moiety. Nanostructures composed of such labeled peptides can be utilized in a variety of applications, including, for example, tracing and tracking location of nanoelements composed of the nanostructures of the present invention in mechanical devices and electronic circuitry; and tracing, tracking and diagnosing concentrations of the nanostructures of the present invention in a living tissue, cell or host.

Thus, according to an embodiment of the present invention, the one or more end-capping modified peptide comprises a labeling moiety. The labeling moiety can form a part of the end-capping moiety or can be the end-capping moiety itself.

As used herein, the phrase "labeling moiety" describes a detectable moiety or a probe which can be identified and traced by a detector using known techniques such as IR, NMR, X-ray diffraction and imaging, HPLC, PET, SPECT, MRI, CT and the like.

Representative examples of labeling moieties include, without limitation, fluorescent moieties, chromophores, phosphorescent moieties, radioactive labeling moieties, heavy metal clusters, as well as any other known detectable moieties.

As used herein, the term "chromophore" refers to a chemical moiety that, when attached to an end-capping moiety or is an end-capping moiety, renders the latter colored and thus visible when various spectrophotometric measurements are applied.

The phrase "fluorescent moiety" refers to a chemical moiety that emits light at a specific wavelength during exposure to radiation from an external source.

The phrase "phosphorescent moiety" refers to a chemical moiety emitting light without appreciable heat or external excitation as by slow oxidation of phosphorous.

A heavy metal cluster can be for example a cluster of gold atoms used, for example, for labeling in electron microscopy or X-ray imaging techniques.

Radiolabeled compounds can be almost any chemical moiety into which a radioactive isotope is incorporated. A radioactive isotope is an element which emits radiation and includes, for example, an α-radiation emitters, a β-radiation emitters or a γ-radiation emitters.

In one example, wherein the Fmoc described hereinabove is used as the end-capping moiety, the end-capping moiety itself is a fluorescent labeling moiety.

In another example, wherein the Fmoc described hereinabove further includes a radioactive fluoro atom ($^{18}$F) is used as the end-capping moiety, the end-capping moiety itself is a radioactive labeling moiety.

The resulting nanostructures of the present invention are preferably stable under acidic and/or basic pH conditions, a wide range of temperatures (i.e., 4-200° C.) and/or proteolytic conditions (i.e., proteinase K).

The nanostructures of the present invention are preferably generated by allowing a highly concentrated aqueous solution of the end-capping modified peptides of the present invention to self-assemble under mild conditions as detailed in Examples 1, in other examples in the Examples section which follows and in other disclosures of non-end-capping modified peptides by the present inventors.

A detailed description of the nanostructure generated according to the teachings of the present invention follows below, starting first with a description of the applications of such nanostructures and the advantages offered thereby.

Generally, the nanostructures of the present invention can be used in various applications which involve the use of nanoscopic elements. Such applications are known in the art and disclosed in U.S. Pat. Nos. 5,581,091, 6,383,923, 6,426,134, 6,428,811, 6,428,811, 6,504,292, 6,530,944, 6,559,468, 6,579,742, 6,586,095, 6,628,053 and in U.S. Patent Application Nos. 20020053257, 20020054461, 20020175618, 20020180077, 20020187504, 20030089899, 20030096113, 20030121764, 20030141189, 20030165074, 20030180491-50030197120, which are incorporated herein by reference.

The nanostructure of the present invention has numerous potential applications. Having a substantially high aspect ratio, the nanostructure of the present invention is an ideal candidate for use in probing application. For example, a nanostructure having a tip diameter of about 10 nm and a length of several micrometers can be used as the tip of an atomic force microscope to probe deep crevices found on integrated circuits, biological molecules or any other nanoscale environment.

Additionally, the nanostructure of the present invention has exceptional material properties. More specifically, due to multiple cooperative forces (hydrogen bonding and hydrophobic packing), the nanostructure is highly robust under extreme pH and temperatures. When another material (e.g., a polymer or a ceramic material) is reinforced with the nanostructure of the present invention, the resulting composition is characterized by a mechanical strength of one or more order of magnitude above the strength of the host material. Such a strong composite material is well suited for many applications such as, but not limited to, in the defense, aerospace and automobile industries.

Moreover, the nanostructure of the present invention can be used in the field of micro- and sub-microelectronic circuitry and devices. More particularly, nanostructure of the present invention can be feature nanoscale wires, referred to herein as nanowires, which can be selectively doped at various locations. The nanowires can be doped, for example, differentially along their length, or radially, and either in terms of identity of dopant, concentration of dopant, or both. This may be used to provide both n-type and p-type conductivity in a single item, or in different items in close proximity to each other, such as in a crossbar array.

Fibril nanostructures of the present invention have technological value, such as in the generation of conductive nanowires which can be formed by metal deposition on the fibrils of the present invention [Scheibel (2003) Proc. Natl. Acad. Sci. USA 100:4527].

The nanostructure of the present invention can be combined with silicon chips so as to restrict motion of electrons or holes within a nanoscale region thereby to provide the system with special electric, optical and/or chemical characteristics. For example, the use of nanostructure as gates in an electronic device allows operation at low gate voltage and enables the switching of several individual devices on the same substrate.

As mentioned hereinabove, the nanostructures of the present invention can be hollow. Being both of nanometer scale and hollow, the nanostructures can serve for heat conduction, e.g., by mixing the nanostructures with a fluid (e.g., a cooling liquid).

Devices and systems incorporating the nanostructures of the present invention may be controlled, for example, using any input signal, such as an electrical, optical or a magnetic signal. The control may involve switching between two or more discrete states or may involve continuous control of a nanowire current, i.e., analog control. In addition to electrical signals, optical signals and magnetic signals, the devices may also be controlled in certain embodiments in response to biological and chemical species, for example, DNA, protein, metal ions. In a more general sense, the nanostructures of the present invention may be charged or have a dipole moment. In other embodiments, the device may be switchable in response to mechanical stimuli, for example, mechanical stretching, vibration and bending. In yet other embodiments, the device may be switchable in response to temperature, pressure or fluid movement, for example, the movement of an environmental gas or liquid.

Still other potential applications of the nanostructure of the present invention are related to enhancement of electromagnetic fields near ultra small metal objects. The physical process of strong field enhancement very close to metal nanoparticles is a well known phenomenon and has been described in detail in the literature. To this end, see, for example, R. H. Doremus and P. Rao, *J. Mater. Res.*, 11, 2834 (1996); M. Quinten, *Appl. Phys.* B 73, 245 (2001) and R. D. Averitt, S. L. Westcott and N. J. Halas, *J. Opt. Soc. Am.* B 16, 1824 (1999), the contents of which are hereby incorporated by reference. In metal nanoparticles, resonant collective oscillations of conduction electrons, also known as particle plasmons, are excited by an optical field. The resonance frequency of a particle plasmons is determined mainly by the dielectric function of the metal, the surrounding medium and by the shape of the particle. Resonance leads to a narrow spectrally selective absorption and an enhancement of the local field confined on and close to the surface of the metal particle. The spectral width of absorption and near-field enhancement depends on the decay time of the particle plasmons. A significant enhancement of the effect of optical field increment may be achieved, by coating the nanostructures of the present invention by a conducting shall layer. Nanoparticles having such structure are called nanoshells.

The process of coating nanostructures having a dielectric core and to form a conducting shell, is known in the art and is described in, for example, WO 01/06257 and WO 02/28552, the contents of which are hereby incorporated by reference.

Following are representative examples of applications in which the nanostructure of the present invention is preferably incorporated.

According to preferred embodiments of the present invention, the nanostructures, and preferably those having a tubular or spherical shape, are filled or partially filled with at least one material (i.e., the nanostructure enclose or partially enclose the material).

The material can be composed of a conducting material, a semiconducting material, a thermoelectric material, a magnetic material (paramagnetic, ferromagnetic or diamagnetic), a light-emitting material, a gaseous material, a biomineral, a polymer and/or an organic material.

For example, the nanostructures may enclose conducting or semiconducting materials, including, without limitation, inorganic structures such as Group IV, Group III/Group V, Group II/Group VI elements, transition group elements, or the like.

As used herein, the term "Group" is given its usual definition as understood by one of ordinary skill in the art. For instance, Group II elements include Zn, Cd and Hg; Group III elements include B, Al, Ga, In and Tl; Group IV elements include C, Si, Ge, Sn and Pb; Group V elements include N, P, As, Sb and Bi; and Group VI elements include O, S, Se, Te and Po.

Thus, for conducting materials, the nanostructures may enclose, for example, silver, gold, copper, platinum, nickel, or palladium. For semiconducting materials the nanostructures may enclose, for example, silicon, indium phosphide, gallium nitride and others.

The nanostructures may also encapsulate, for example, any organic or inorganic molecules that are polarizable or have multiple charge states. For example, the nanostructures may include main group and metal atom-based wire-like silicon, transition metal-containing wires, gallium arsenide, gallium nitride, indium phosphide, germanium, or cadmium selenide structures.

Additionally, the nanostructure presented herein may enclose various combinations of materials, including semiconductors and dopants. Representative examples include, without limitations, silicon, germanium, tin, selenium, tellurium, boron, diamond, or phosphorous. The dopant may also be a solid solution of various elemental semiconductors, for example, a mixture of boron and carbon, a mixture of boron and P, a mixture of boron and silicon, a mixture of silicon and carbon, a mixture of silicon and germanium, a mixture of silicon and tin, or a mixture of germanium and tin. In some embodiments, the dopant or the semiconductor may include mixtures of different groups, such as, but not limited to, a mixture of a Group III and a Group V element, a mixture of Group III and Group V elements, a mixture of Group II and Group VI semiconductors. Additionally, alloys of different groups of semiconductors may also be possible, for example, a combination of a Group II-Group VI and a Group III-Group V semiconductor and a Group I and a Group VII semiconductor.

Specific and representative examples of semiconducting materials which can be encapsulated by the nanostructure presented herein include, without limitation, CdS, CdSe, ZnS and $SiO_2$.

The nanostructure presented herein may also enclose a thermoelectric material that exhibits a predetermined thermoelectric power. Preferably, such a material is selected so that the resulting nanostructure composition is characterized by a sufficient figure of merit. Such composition, as further detailed hereinunder, may be used in thermoelectric systems and devices as heat transfer media or thermoelectric power sources. According to a preferred embodiment of the present invention the thermoelectric material which can be encapsulated in the nanostructure of the present invention may be a bismuth-based material, such as, but not limited to, elemental bismuth, a bismuth alloy or a bismuth intermetallic compound. The thermoelectric material may also be a mixture of any of the above materials or other materials known to have thermoelectric properties. In addition the thermoelectric material may also include a dopant. Representative examples include, without limitation, bismuth telluride, bismuth selenide, bismuth antimony telluride, bismuth selenium telluride and the like. Other materials are disclosed, for example, in U.S. Patent Application No. 20020170590.

As stated, the nanostructure presented herein may also enclose magnetic materials. Generally, all materials in nature possess some kind of magnetic properties which are manifested by a force acting on a specific material when present in a magnetic field. These magnetic properties, which originate from the sub-atomic structure of the material, are different from one substrate to another. The direction as well as the magnitude of the magnetic force is different for different materials.

Whereas the direction of the force depends only on the internal structure of the material, the magnitude depends both on the internal structure as well as on the size (mass) of the material. The internal structure of the materials in nature, to which the magnetic characteristics of matter are related, is classified according to one of three major groups: diamagnetic, paramagnetic and ferromagnetic materials, where the strongest magnetic force acts on ferromagnetic materials.

In terms of direction, the magnetic force acting on a diamagnetic material is in opposite direction than that of the magnetic force acting on a paramagnetic or a ferromagnetic material. When placed in external magnetic field, a specific material acquires a non-zero magnetic moment per unit volume, also known as a magnetization, which is proportional to the magnetic field vector. For a sufficiently strong external magnetic field, a ferromagnetic material, due to intrinsic non-local ordering of the spins in the material, may retain its magnetization, hence to become a permanent magnet. As opposed to ferromagnetic materials, both diamagnetic and paramagnetic materials loose the magnetization once the external magnetic field is switched off.

Representative examples of paramagnetic materials which can be enclosed by the nanostructure of the present embodiments include, without limitation, cobalt, copper, nickel, and platinum. Representative examples of ferromagnetic materials include, without limitation, magnetite and NdFeB.

Other materials which may be encapsulated by the nanostructure of the present embodiments include, without limitation, light-emitting materials (e.g., dysprosium, europium, terbium, ruthenium, thulium, neodymium, erbium, ytterbium or any organic complex thereof), biominerals (e.g., calcium carbonate) and polymers (e.g., polyethylene, polystyrene, polyvinyl chloride, polynucleotides and polypeptides).

In order to generate the filled nanostructure described herein, the foreign material is introduced into the internal cavity of the nanostructure, to encapsulate the material in nano structure.

A representative method of filling is described, for example, in WO 2004/060791. Other methods of filling nanotubes are described in "Capillarity-induced filling of carbon nanotubes", P M Ajayan et al., Nature, vol. 361, 1993, pp. 333-334; "A simple chemical method of opening and filling carbon nanotubes", S C Tsang et al., Nature, vol. 372, 1994, pp. 159-162; U.S. Pat. Nos. 5,916,642 and 6,361,861.

Filled nanostructures can be used as such, as further described hereinbelow. Alternatively, the peptide mold (i.e., nanotube or nanosphere of the present embodiments), can be removed, for example, by using a protease, to increase properties of the casted material, such as conductivity.

Hence, depending on the foreign material present in (encapsulated in) and/or around (coated on, as further described hereinbelow) the nanostructure of the present embodiments, the peptide nanostructure can be an insulator, a conductor, a semiconductor, thermoelectric, magnetic and the like. The nanostructure of the present embodiments can also be utilized as vehicles in which atoms of different materials (e.g., conducting, semiconducting, magnetic, thermoelectric, chemical or biological agents) may be enclosed, either in a condensed or in a gaseous state.

Hence, depending on the number and type of amino acids used, and on the foreign material present in (encapsulated in) and/or around (coated on, as further described hereinbelow) the nanostructure presented herein, the nanostructure can be an insulator, a conductor, a semiconductor, thermoelectric, magnetic and the like. The nanostructure presented herein can also be utilized as carriers and vehicles onto and/or into which atoms of different materials (e.g., conducting, semiconducting, magnetic, thermoelectric, chemical or biological agents) may be enclosed, either in a condensed or in a gaseous state, or otherwise incorporated thereto.

Referring now to the drawings, FIG. 1 is a flowchart diagram of a method of positioning a target molecule at a predetermined location. The method comprises the following method steps in which in a first step, a magnetic nanowire is provided. The magnetic nanowire is preferably formed of a magnetic material at least partially enclosed by the peptide nanostructure of the present invention. According to a preferred embodiment of the present invention, the nanostructure has at least one segment associated with a functional group or ligand, which are capable of binding to the target molecule.

Representative examples of functional groups which are contemplated include, without limitation, thiols, disulfides, cyanides, amines, carboxylic acids, phosphonates, siloxanes or hydroxamic acids. Representative examples of ligands which are contemplated include, without limitation, proteins, fibronectin, DNA, RNA, enzymes, ribozymes, hydrophobic materials, hydrophillic materials, cells, tissue, microorganisms, bacteria, viruses and chemoattractant.

In a second step of the method, the magnetic nanowire is bound to the target molecule, and in the third step, the magnetic nanowire (and the target molecule to which it bounds) is exposed to a magnetic field. As stated, when a magnetic material is placed in a magnetic field, its magnetic properties are manifested by forces acting thereon. Thus, by a judicious selection of the magnetic field (magnitude and direction) the nanowire, under the influence of the magnetic force, may be moved, together with the target molecule, to the desired location.

According to another aspect of the present invention, there is provided a method of delivering an agent to a subject. The method comprises the following method steps which are illustrated in the flowchart diagram of FIG. 2.

Figure 2:
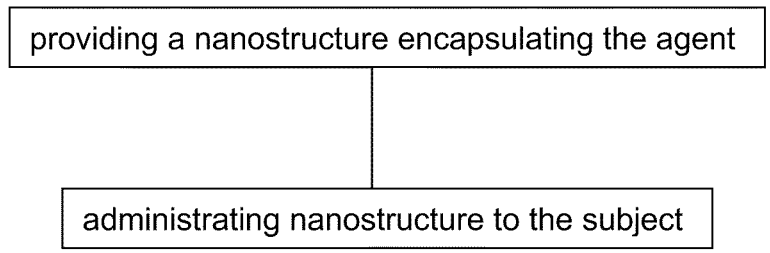
FIG. 2 is a flowchart diagram presenting a method of delivering an agent to a subject according to a preferred embodiment of the present invention.

Referring to FIG. 2, in a first step of the method, a composition having the agent enclosed by the peptide nanostructure of the present invention is provided, and in a second step, the nanostructure is administrated to the subject. The present aspect of the invention has numerous of potential application in the field of drug delivery, DNA transfection, tissue engineering, biosensors, composite materials for implants and other medical and biological applications. The nanostructure of the present invention has a particular advantage for these applications because of its low toxicity, and biodegradability and possible control of its hydrophobicity. In this respect, according to a preferred embodiment of the present invention the composition may further comprise one or more functional groups. In one embodiment, the functional group is an antigen-binding moiety, by which is meant a moiety comprising the antigen-recognition site of an antibody. Examples of a moiety comprising the antigen-recognition site of an antibody include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies. Single chain or multiple chain antigen-recognition sites can be used. Multiple chain antigen-recognition sites can be fused or unfused.

The antigen-binding moiety can be selected from any known class of antibodies. Known classes of antibodies include, but are not necessarily limited to, IgG, IgM, IgA, IgD, and IgE. The various classes also can have subclasses. For example, known subclasses of the IgG class include, but are not necessarily limited to, IgG1, IgG2, IgG3, and IgG4. Other classes have subclasses that are routinely known by one of ordinary skill in the art.

The antigen-binding moiety can be selected from an antibody derived from any species. "Derived from," in this context, can mean either prepared and extracted in vivo from an individual member of a species, or prepared by known biotechnological techniques from a nucleic acid molecule encoding, in whole or part, an antibody peptide comprising invariant regions which are substantially identical to antibodies prepared in vivo from an individual member of the species or an antibody peptide recognized by antisera specifically raised against antibodies from the species. Exemplary species include, but are not limited to, human, chimpanzee, baboon, other primate, mouse, rat, goat, sheep, and rabbit, among others known in the art. In one embodiment, the antibody is chimeric, i.e., comprises a plurality of portions, wherein each portion is derived from a different species. A chimeric antibody, wherein one of the portions is derived from human, can be considered a humanized antibody.

Antigen-recognition moieties are available that recognize antigens associated with a wide variety of cell types, tissues, and organs, and a wide variety of medical conditions, in a wide variety of mammalian species. Exemplary medical conditions include, but are not limited to, cancers, such as lung cancer, oral cancer, skin cancer, stomach cancer, colon cancer, nervous system cancer, leukemia, breast cancer, cervical cancer, prostate cancer, and testicular cancer; arthritis; infections, such as bacterial, viral, fungal, or other microbial infections; and disorders of the skin, the eye, the vascular system, or other cell types, tissues, or organs.

When the nanostructure of the present invention encapsulates a conducting material, a nanowire is formed. Such a nanowire can be used as an interface between macroscopic systems and individual objects having nanometer dimensions.

Hence, further in accordance with the present invention there is provided a device for obtaining information from a nanoscale environment. Broadly speaking, this device is capable of serving as an interface between macroscopic systems and individual objects having nanometer dimensions. The device according to this aspect of the present invention may comprise one or more nanostructures, including such that encapsulate a conducting material, which facilitate information exchange between the macroscopic system and the nanoscale environment. Individual nanostructures, nanowires or bundles of nanostructures can be recovered from peptides, as further detailed hereinabove, in accordance with the present invention. Assemblies of nanostructures can be fabricated, for example, by self-assembly of groups of nanostructures, as further detailed and exemplified in the Examples section that follows.

Figure 3:
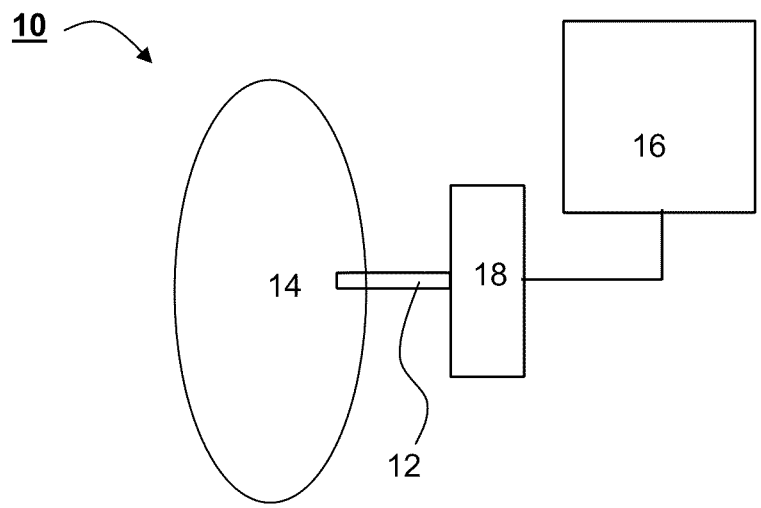
FIG. 3 is a schematic illustration of a device for obtaining information from a nanoscale environment, according to a preferred embodiment of the present invention.

Referring now to the drawings, FIG. 3 is a schematic illustration of the device described above, which is referred to herein as device 10. In its most basic form, device 10 comprises a nanostructure 12, which can be a conductive or a semi-conductive nanowire or a nanostructure encapsulating a conducting or a semi-conducting material, and a detection system 16. As stated, nanostructure 12 preferably comprises a plurality of peptides, each having no more than 4 amino acids.

Nanostructure 12 serves for collecting signals from a nanoscale environment 14. Any type of signals can be collected by nanostructure 12 including, without limitation, mechanical, optical, electrical, magnetic and chemical signals. Detection system 16 serves for interfacing with nanostructure 12 and receiving the signals collected thereby. Hence, by collecting signals using nanostructure 12 and detecting the signals using system 16, device 10 is capable of sensing, measuring and analyzing nanoscale environment 14.

According to a preferred embodiment of the present invention device 10 may further comprise a supporting element 18 onto which nanostructure 12 is mounted. Nanostructure 12 is connected to supporting element 18 at one end, with the other end being free and, due to its nanometric dimension, capable of coming into direct contact or near proximity to nanoscale environment 14. Preferably, supporting element 18 can physically scan nanoscale environment 14 to thereby allow nanostructure 12 to collect signals from, or deliver signals to a plurality of locations of nanoscale environment 14. The "sensing end" of nanostructure 12 interacts with objects being sensed, measured or analyzed by means which are (either individually or in combination) physical, electrical, chemical, electromagnetic or biological. This interaction produces forces, electrical currents or chemical compounds which reveal information about the object.

Nanostructure 12 and supporting element 18 in combination can essentially be considered as a transducer for interacting with nanoscale environment 14. Conventional probe microscopy techniques are enabled and improved by the use of device 10, according to a preferred embodiment of the present invention.

Examples of conventional systems of this type include scanning tunneling microscopes, atomic force microscopes, scanning force microscopes, magnetic force microscopes and magnetic resonance force microscopes.

Device 10 is fundamentally different from conventional probe microscopy tips in its shape and its mechanical, electronic, chemical and/or electromagnetic properties. This difference permits new modes of operation of many probe microscopes, and new forms of probe microscopy. Device 10 is capable of imaging, at nanoscale resolution or greater, surfaces and other substrates including individual atoms or molecules such as biolmolecules. Device 10 can replace relevant parts (e.g., tips) of any of the above systems.

In a preferred embodiment, supporting element 18 and/or nanostructure 12 may be pre-coated with a layer of conductive material in order to produce a good electrical contact therebetween.

Device 10 is particularly useful when used in tapping mode atomic force microscopy. In this mode, a change in amplitude of an oscillating cantilever driven near its resonant frequency is monitored as nanostructure 12 taps the surface of nanoscale environment 14. The sharp frequency response of high-quality cantilevers makes this technique exquisitely sensitive. Nanostructure 14 has the advantage that it is both stiff below a certain threshold force, but is compliant above that threshold force. More specifically, below the Euler buckling force, there is no bending of nanostructure 12. The Euler buckling force of nanostructure 12 is preferably in the one nano-Newton range. Once the Euler bucking force is exceeded, nanostructure 12 bends easily through large amplitudes with little additional force. In addition, nanostructure 12 is extremely gentle when laterally touching an object.

The result is that gentle, reliable atomic force microscopy imaging may be accomplished in the tapping mode with even extremely stiff, high-resonant frequency cantilevers. In contrast to the hard silicon pyramidal tip of existing systems, which can easily generate impact forces being larger than 100 nano-Newtons per tap, and therefore may substantially modify the geometry of soft samples such as large bio-molecules, nanostructure 12 serves as a compliant probe which moderates the impact of each tap on the surface.

An additional advantage of device 10 is its capability to explore regions of nanoscale environment 14 previously inaccessible to high resolution scanning probes. In this embodiment, nanostructure 12 is preferably of tubular shape so as to allow nanostructure 12 to penetrate into deep trenches of environment 14. Due to the above mention special mechanical characteristics of nanostructure 12 scanning force microscopy imaging of tortuous structures can be achieved without damaging nanostructure 12 or the imaged object.

Device 10 of the present invention can also be utilized to retrieve other types of information from nanoscale environment 14, such as, but not limited to, information typically obtained via conventional friction force microscopy. Friction force microscopy measures the atomic scale friction of a surface by observing the transverse deflection of a cantilever mounted probe tip. The compliance of nanostructure 12 above the Euler threshold as described above, provides for a totally new method of elastic force microscopy. By calibration of the Euler buckling force for nanostructure 12, and making appropriate atomic force microscopy measurements using nanostructure 12, one can obtain direct information about the elastic properties of the object being imaged.

Device 10 may also be used to perform nanoscale surface topography measurement. Motions of supporting element 18 can be calibrated by measurement of surfaces having known geometries (e.g., pyrolytic graphite with surface steps). Once properly calibrated, supporting element 18 and nanostructure 12 can provide precise measurement of the topography of surfaces and fabricated elements such as vias and trenches on integrated-circuit elements.

An additional use of device 10 is in mechanical resonance microscopy, which can be facilitated by mechanical resonances in nanostructure 12. These resonances may be utilized as a means of transduction of information about the object being sensed or modified. Such resonances, as will be known by one skilled in the art, can be sensed by optical, piezoelectric, magnetic and/or electronic means.

Nanostructure 12 can also act as a sensitive antenna for electromagnetic radiation. The response of nanostructure 12 to electromagnetic radiation may be recorded by detecting and measuring frequency currents passing therethrough as it and the object being sensed interact together in a nonlinear way with electromagnetic radiation of two or more frequencies. Via its interaction with electromagnetic fields of specified frequencies, nanostructure 12 may excite electronic, atomic, molecular or condensed-matter states in the object being examined, and the transduction of information about that object may occur by observation of the manifestations of these states.

Also of interest is the use of device 10 for probing biological systems. For example, device 10 can perform DNA sequencing by atomic force microscopy imaging of DNA molecules whereby nanostructure 12, due to its physical and chemical properties, permits the recognition of individual bases in the molecule.

An additional apparatus for polynucleotide sequencing is further described in more details hereinafter.

In another biological application, device 10 can also be used for electrical or electrochemical studies of living cells. Knowledge of cell activity can be achieved, e.g., by measuring and recording electrical potential changes occurring within a cell. For example, device 10 of the present invention can accurately monitor specific cytoplasmic ions and cytosolic calcium concentrations with a spatial resolution far superior to those presently available. Living cells which can be studied using device 10 include, without limitations, nerve cell bodies and tissue culture cells such as smooth muscle, cardiac, and skeletal muscle cells.

Additionally, device 10 can be used, for example, to obtain and measure near field light from nanoscale environment 14. For the purpose of providing a self contained document a description of the near field phenomenon precedes the description of the presently preferred embodiment of the invention.

When light impinges on a boundary surface (such as the surface of nanoscale environment 14) having a varying refractive index at an angle which causes total reflection, the incident light is totally reflected on the boundary surface (reflection plane), in which case the light exudes to the opposite side of the reflection plane. This exuding light is called "near-field light." Other than the foregoing, the near-field light also includes light which exudes from a miniature aperture smaller than the wavelength of the light, through which the light is passed.

The near-field light can be utilized to analyze a surface state (shape, characteristics or the like) of a sample such as semiconductor materials, organic or inorganic materials, vital samples (cells) and the like. An ordinary optical microscope cannot measure a sample at a resolution higher than the wavelength of light due to diffraction of the light. This is called "diffraction limit of light." An analysis utilizing near-field light permits measurements at a resolution exceeding the diffraction limit of light.

According to a preferred embodiment of the present invention nanostructure 12 is adapted to collect near-field light of nanoscale environment 14. As the near-field light incidents on nanostructure 12, electronic excitation are induced therein. These electronic excitations cause a current to flow through nanostructure 12, toward detection system 16 which detects, records and/or analyzes the current.

It is appreciated that the above embodiments merely exemplify the potential use of device 10 for obtaining vital information from a nanoscale environment, previously unattained by conventional systems and apparati. The geometrical shape, nanometric size and physical properties of nanostructure 12 may also be used also for performing tasks, other than, obtaining information.

When two nanostructures encapsulating a conducting material are positioned in closed proximity one to another, a nanometer-scale gap can be formed. Such nanometer-scale gap, also referred to herein as a nanogate, is used in the present invention as a polynucleotide detection gate.

Thus, according to another aspect of the present invention, there is provided an apparatus 11 for characterizing a nucleic acid sequence of a polynucleotide.

Figure 4A:
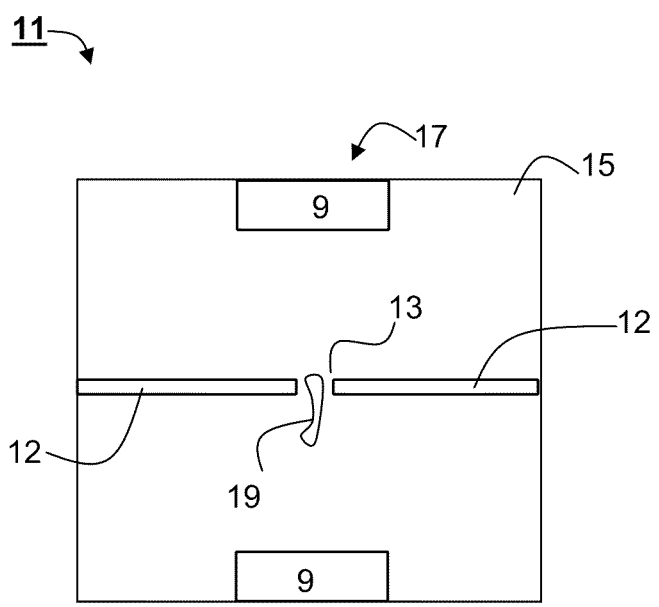
FIGS. 4a-b are schematic illustrations of a top view (FIG. 4a) and a side view (FIG. 4b) of an apparatus for characterizing a nucleic acid sequence of a polynucleotide, according to a preferred embodiment of the present invention.
Figure 4B:
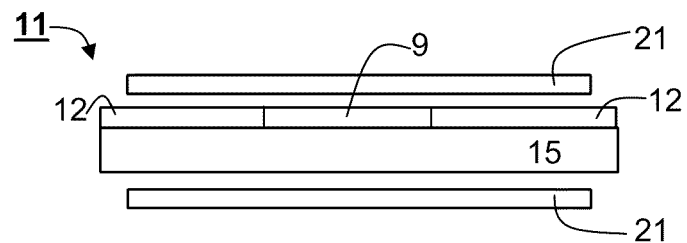

Reference is now made to FIGS. 4*a*-*b*, which schematically illustrate a top view (FIG. 4*a*) and a side view (FIG. 4*b*) of apparatus 11. Apparatus 11 comprises a nanogate 13 defined by two conducting nanowires 12, which, as stated, are formed of a conducting material enclosed by the peptide nanostructures of the present invention. A typical distance between nanowires 12, i.e., a typical width of nanogate 13 is between about 1 nm and 10 nm, inclusive more preferably between about 2 nm and 6 nm, inclusive. Nanowires 12 are preferably formed on a hydrophilic and nonconductive (e.g., silicon oxide) surface 15.

Apparatus 11 further comprises a positioning device 17, for positioning the polynucleotide 19 within nanogate 13. As further detailed hereinunder, in one embodiment, positioning device 17 comprises an arrangement of electrodes 9 designed and constructed to generate an electric field capable of inducing electrophoresis forces on polynucleotide 19.

A controlled thin layer of water or other liquid on surface 15 facilitates the loading and delivery of polynucleotide 19 through the nanogate 13. The width of nanogate 13 (1-10 nm) is sufficient for passage of a single polynucleotide. One ordinarily skilled in the art would appreciate that the specific requirement for nanogate width is also dependent on the temperature and solvent conditions such as the pH and ionic strength of the water or the liquid layer.

When the distance between nanowires 12 is within the above range, significant electron tunneling across the nanogate 13 is generated with application of a tunneling biased voltage thereon. In an aqueous solution (e.g., water), the width of a single-stranded DNA molecule is about 2-3 nm (including some bound water molecules), while that of a double-stranded DNA is about 3-4 nm. Thus, the above preferred ranges for the width of nanogate are sufficient for the passage of either type of DNA chain, and for detection by tunneling current measurement.

The thickness of the adsorbed water or liquid layer increases with increasing humidity. By controlling the relative humidity, the thickness of the water layer can be manipulated. In addition, by using specific types of surfaces or chemically modified ones, the water adsorption, and thus the thickness of the water layer, can be enhanced. It is possible to maintain a water layer with a thickness that is comparable to that of a single- or double-stranded DNA molecule.

When a nucleic acid sample is loaded into apparatus 11 (e.g., using a micro- or nano-fluidic injection device, not shown), positioning device 17 delivers polynucleotide 19 to nanogate 13, for example, by a pair of electrodes 9.

A precise control of the locomotion of polynucleotide 19 is achieved through the use of electric fields in conjunction with the water or liquid layer. According to a preferred embodiment of the present invention, two electric fields are generated by positioning device 17. The first such field is preferably parallel to surface 15. This field, preferably controlled by electrodes 9, is selected so as to induce electrophoresis forces on polynucleotide 19 in a direction which is parallel to surface 15.

The second electric field is preferably perpendicular to surface 15. This field serves for holding polynucleotide 19 in place and is preferably applied using two planar electrodes 21, located above and beneath surface 15 (sees FIG. 4*b*).

Thus, the step size of polynucleotide 19 in movement on surface 15 and through nanogate 13 is controlled by the direction, magnitude and duration of the parallel electric field in conjunction with the perpendicular electric field. According to a preferred embodiment of the present invention these two electric fields and the process of molecular characterization are synchronized and coordinated to minimize the time spent by polynucleotide 19 in device apparatus 11. To provide an efficient characterization process, when polynucleotide 19 enters nanogate 13 the parallel electric field is preferably temporarily terminated until the characterization process is completed.

With the perpendicular electric field at the proper magnitude and direction, polynucleotide 19 remains in its location in nanogate 13. For example, for a single-stranded DNA molecule, the perpendicular electric field is preferably directed upwards, so that the (negatively charged) phosphate groups of the DNA molecule are pulled down on surface 15, while its nucleotides pointing upward as desired for base detection. An additional advantage of the use of perpendicular electric field is that this filed prevents any potential drift polynucleotide 19.

When the characterization process is completed, the parallel electric field is generated again so as to remove polynucleotide 19 from gate 13 and to guide another polynucleotide into gate 13.

The characterization process of polynucleotide 19 using nanogate 13 is known in the art (to this end see, e.g., U.S. Patent Application 20030141189, the contents of which are hereby incorporated by reference). For example, one method is by measuring tunneling current across nanogate 13. Since the chemical compositions and structures of the nucleotides are different, the screening effect of each distinct nucleotide on the tunneling current and other tunneling parameters is different. Representative examples of tunneling parameters, beside the tunneling current, include, without limitation, tunneling I-V curve and/or tunneling dI/dV-V curve, where I represent the tunneling current V represent the tunneling voltage and dI/dV represent the tunneling current slope (first derivative).

Thus, by detecting the difference in the tunneling parameters polynucleotide passing through nanogate 13, the nucleic acid sequence of the polynucleotide can be determined. Using some DNA molecules of known sequence, apparatus 11 can be calibrated, so as to establish a unique tunneling characteristic profile for each distinct DNA base. This tunneling profile is then used as a fingerprint to identify an individual base. With the ability to move polynucleotide 19 through nanogate 13 in a well-controlled manner, reliable sequence information can therefore be obtained at a speed much faster than the current DNA sequencing technology. Since the tunneling electrons likely emerge from a single (or a few) atom(s) of one nanowire, and tunnel through the nanogate 13 to the tip of the other nanowire for the shortest possible distance, the size of the tunneling electron beam is likely to be within a few angstroms (a fraction of a nanometer). This is sufficiently fine to make precise detection of an individual nucleotide of the DNA molecule possible. Therefore, the tunneling detection method can offer a better resolution than that of atomic force microscopy (AFM) probing, described below. The tunneling current method should be able to perform DNA sequencing on either single-stranded or double-stranded DNA molecules.

Other methods of nucleic acid sequence characterization which are contemplated are, dielectric constant measurements, atomic force microscopy (AFM) or electrostatic force microscopy (EFM) probing.

When the tips of nanowires 12 are placed in close proximity to each other, they can act as elements of a parallel plate capacitor. An alternating voltage (AC voltage) applied between the nanowires 12 in characterized by a phase lag of 90° between the applied voltage and measured current. When a dielectric material such as a nucleic acid molecule is present between the nanowires, the phase lag varies as a function of the dielectric constant of the dielectric material. Thus, according to a preferred embodiment of the present invention, the nucleic acid sequence characterization is done by measuring the dielectric constant of polynucleotide.

The capacitance of the parallel plate capacitor depends on the dielectric constant of the nucleotides and the liquid that are between nanowires 12. For example, the four DNA nucleotides (thymine, adenine, cytosine and guanine) have different structures and compositions, hence also different dielectric constants. When the DNA molecule is positioned in water, the interaction between the DNA and the water molecules also contributes to differences in dielectric constant. Some water molecules are bound or semi-bound around the DNA chain thus less freedom for rotation and are thus less polarizable than the free water molecules in a bulky phase. Consequently, the dielectric constant of the bound or semi-bound water molecules is significantly smaller than that of free water molecules. Since each of the nucleotides has a somewhat different orientation and spatial relation with the phosphate chain, the geometry of the bound or semi-bound water molecules around each distinct nucleotide is also somewhat distinct. This distinct geometry can confer different dielectric constants for each base.

The dielectric constant can be determined by measuring by measuring the phase shift between the input AC voltage and an output voltage signal. Knowing the phase shift, the input and output voltages and the AC frequency, the capacitance, hence also the dielectric constant of polynucleotide 19 can be determined.

By using some DNA molecules of known sequence, calibration of the dielectric constant measurement is possible. A unique phase-shift profile can be established for each distinct DNA base. This profile can be used as a fingerprint to identify an individual base.

Nanostructure generated in accordance with the teachings of the present invention can also be utilized as part of a field emitting device.

Hence, according to another aspect of the present invention, there is provided a field emitter device, which is referred to herein as device 20.

Figure 5A:
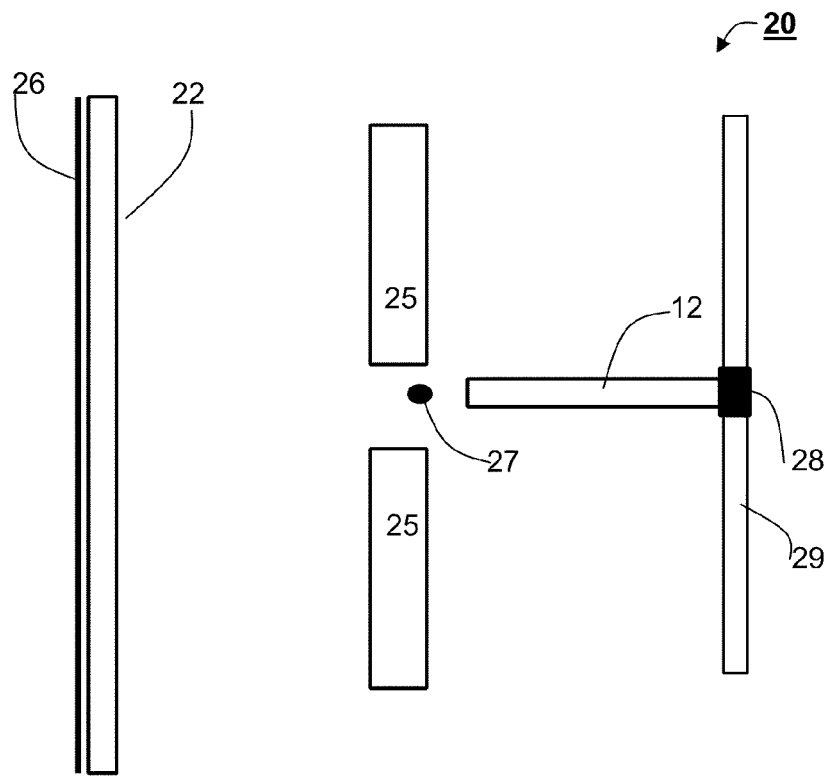
FIG. 5a is a schematic illustration of a field emitter device, according to a preferred embodiment of the present invention.

Reference is now made to FIG. 5a, which is a schematic illustration of a cross sectional view of device 20, according to a preferred embodiment of the present invention. Device 20 preferably comprises an electrode 22 and a nanostructure 12. Electrode 22 and nanostructure 12, which can be a conductive or a semi-conductive nanowire or a nanostructure encapsulating a conducting or a semi-conducting material, are designed and constructed such that when an electrical field is formed therebetween, electrons 27 are extracted from nanostructure 12 by tunneling through the surface potential barrier. Once emitted from nanostructure 12, electrons 27 can be accelerated, redirected and focused so as to energetically excite atoms of a specific material, as further detailed hereinunder.

Figure 5B:
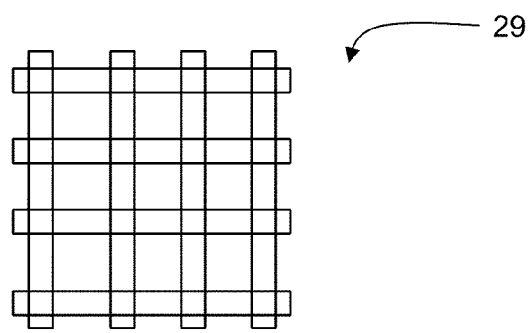
FIG. 5b is a schematic illustration of a matrix of row and column electrodes, according to a preferred embodiment of the present invention.

Device 20 may be integrated in many apparati, such as, but not limited to, a field emitter display. In this embodiment, a plurality of nanostructures may be positioned in cross points 28 of a matrix 29 of electrodes. Matrix 29, better illustrated in FIG. 5b, is formed of a plurality of row and column electrodes. Thus, each cross point 28 can be addressed by signaling the respective row and column electrodes. Upon a suitable signal, addressed to a specific cross point, the respective bundle of nanostructures 12 emits electrons, in accordance with the above principle.

Device 20 (or the apparatus in which device 20 is employed) may further comprise a substrate 26 having a fluorescent powder coating, capable of emitting light upon activation by the electrons. The fluorescent powder coating may be either monochromatic or multichromatic. Multichromatic fluorescent powder may be, for example, such that is capable of emitting red, green and blue light, so that the combination of these colors provides the viewer with a color image. Device 20 may further comprise a focusing element 25 for ensuring that electrons 27 strike electrode 22 at a predetermined location.

A special use of field emitter device, such as device 20, is in the area of electron beam lithography, in particular when it is desired to achieve a precise critical dimension of order of a few tens of nanometers. The present invention successfully provides an apparatus for electron emission lithography apparatus, generally referred to herein as apparatus 30. As further detailed hereinbelow, apparatus 30 is capable of transferring a pattern of a mask in a nanoscale resolution.

Figure 6:
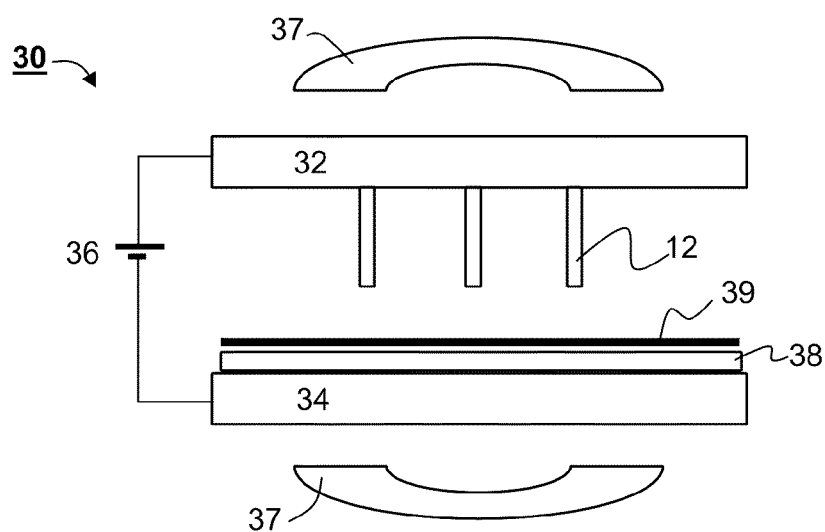
FIG. 6 is a schematic illustration of an apparatus for electron emission lithography, according to a preferred embodiment of the present invention.

Reference is now made to FIG. 6, which is a schematic illustration of apparatus 30. Apparatus 30 comprises an electron emission source 32 and an electrically conducting mounting device 34. According to a preferred embodiment of the present invention, sources 32 includes one or more nanostructures 12, which, as stated, is composed of a plurality of peptides. Source 32 and mounting device 34 are kept at a potential difference, e.g., via a voltage source 36. The potential difference is selected such that electrons are emitted from source 32 (similarly to device 20).

A sample 38, on which an e-beam resist 39 to be patterned is formed, is disposed on mounting device 34, in a predetermined distance apart from a source 32. The electrons emitted from nanostructure 12 perform a lithography process on a sample 38 mounted thereon. Subsequently, if a developing process is performed, portions of resist 39 which were exposed to the emitted electrons remain when the resist 39 is negative, while portions of resist 39 not exposed to an electron beam remain when resist 39 is positive.

Source 32 and mounting device 34 are preferably positioned in a magnetic field generated by a magnetic field generator 37. Magnetic field generator 37 is designed to precisely control a magnetic field according to the distance between nanostructures 12 and resist 39, so that the electrons emitted from nanostructure 12 reach the desired positions on resist 39. Being charged particles moving in a magnetic field, the electrons are subjected to a magnetic force, perpendicular to their direction of motion (and to the direction of the magnetic field vector). Thus, a track of the movement of the electrons is controlled by magnetic field generator 37, which redirect the electron to the desirable position.

Consequently, the shape of nanostructures 12 can be projected upon sample 38, to thereby perform a lithographic process thereon. As described above, according to the present invention, since nanostructures 12 are used as electron emission sources, a lithography process can be performed with a precise critical dimension. In addition, since electrons emitted from nanostructures 12 carbon depreciate portions of resist 39 corresponding to nanostructure 12, a deviation between the center of a substrate and the edge thereof are substantially prevented.

An additional use of nanostructure 12 is in the field of information storage and retrieving. In certain embodiments, further detailed hereinunder, switching may be achieved based on the observation that the conductance of semiconducting nanowires can change significantly upon either a gate or bias voltage pulse when the surface of the nanowires are appropriately modified, for example, with molecules, functional groups or nanocrystals. Other properties of the nanowire may also be used to record memory, for example, but not limited to, the redox state of the nanowire, mechanical changes, magnetic changes, induction from a nearby field source, and the like.

Specifically, with respect to changes in conductance, subjection to positive or negative gate or bias voltage pulses may cause the change of charge states in the molecules or nanocrystals, and induces the device to make a fully reversible transition between low and high resistance states. The different states may hysterically persist in the set state, even after the voltage source is deactivated. This feature (change in electrical properties upon voltage pulse) may enable the fabrication of electrically erasable and rewritable memory switching devices in which the reversible states are indicated by the conductance of the nanowires. In addition, the memory switching devices may be assembled specifically from nanoscale material building blocks, and may not be created in planar materials by lithography.

Figure 7A:
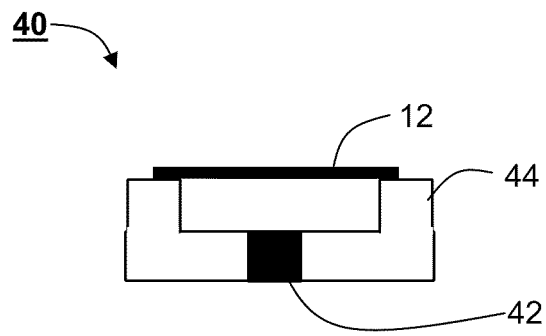
FIGS. 7a-b present a schematic illustration of a memory cell, according to a preferred embodiment of the present invention.
Figure 7B:
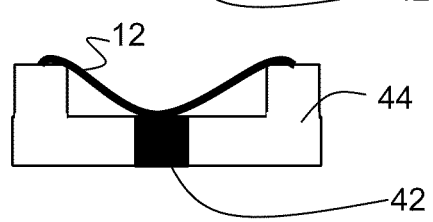

Reference is now made to FIGS. 7a-b, which are schematic illustration of a memory cell, generally referred to herein as cell 40. In its simplest configuration, cell 40 comprises an electrode 42 and a nanostructure 12, which can be a conductive or a semi-conductive nanowire or a nanostructure encapsulating a conducting or a semi-conducting material. Nanostructure 12 preferably capable of assuming one of at least two states. For example, as already described hereinabove, nanostructure 12 has the capability to deflect when the Euler buckling force is exceeded, thus, a first state of nanostructure 12 can be a non-deflected state (when an external force applied on nanostructure is below Euler buckling force) and a second state of nanostructure 12 can be a deflected state (when the external force is above or equals the Euler buckling force).

Nanostructure 12 is preferably be suspended by one or more supports 44 over electrode 42. Nanostructure 12 may be held in position on support(s) 44 in more than one way. For example, nanostructure 12 is held in position on support(s) 44 by or any other means, such as, but not limited to, by anchoring nanostructure 12 to support(s) 44. The holding of nanostructure 12 in its place on support(s) 44 can also be facilitated by chemical interactions between nanostructure 12 and support(s) 44, including, without limitation, covalent bonding.

Electrode 42, nanostructure 12 and the distance therebetween are preferably selected such that electrical current flows through electrode 42 and/or nanostructure 12, generates an electric force on nanostructure 12 which is larger than the Euler buckling force. Thus, temporarily electric current(s) transform nanostructure 12 from the first state (FIG. 7a) to the second state (FIG. 7b).

A plurality of cells like cell 40 can be incorporated to provide an electromechanical memory array. Each cell in the array can be in either a first state or a second state thus can store a binary information of a first type of datum (say, "0") and a second type of datum (say, "1"). As the size of nanostructure 12 is in the nanometric scale, many such cells can be integrated in a single array so that the information storage capacity of the entire array is substantially larger, or at least equivalent to modern memory devices. Each cell may be read or written by applying currents and or voltages to electrode 42 or nanostructure 12.

More specifically, when nanostructure 12 is in a non-deflected state (FIG. 7a), cell 40 is characterized by an open circuit, which may be sensed as such on either nanostructure 12 or trace electrode 42 when so addressed. When nanostructure 12 is in a deflected state (FIG. 7b), cell 40 is characterized by a rectified junction (e.g., Schottky or PN), which may be sensed as such on either nanostructure 12 or trace electrode 42 when so addressed.

As will be appreciated by one ordinarily skilled in the art, cell 40 (and therefore an integrated array of a plurality of such cells) is characterized by a high ratio of resistance between "0" and "1" states. Switching between these states is accomplished by the application of specific voltages across nanostructure 12 or electrode 42. For example, "readout current" can be applied so that the voltage across a respective junction is determined with a "sense amplifier." It will be appreciated that such reads are non-destructive. More specifically, unlike DRAM systems, where write-back operations are required after each read, cell 40 retains its state even once read is performed.

As stated, the nanostructure of the present invention can also encapsulate a magnetic material, hence to form a magnetic nanowire. A plurality of such magnetic nanowires can be used as a memory cell, which operates according to magnetic principles.

Figure 8:
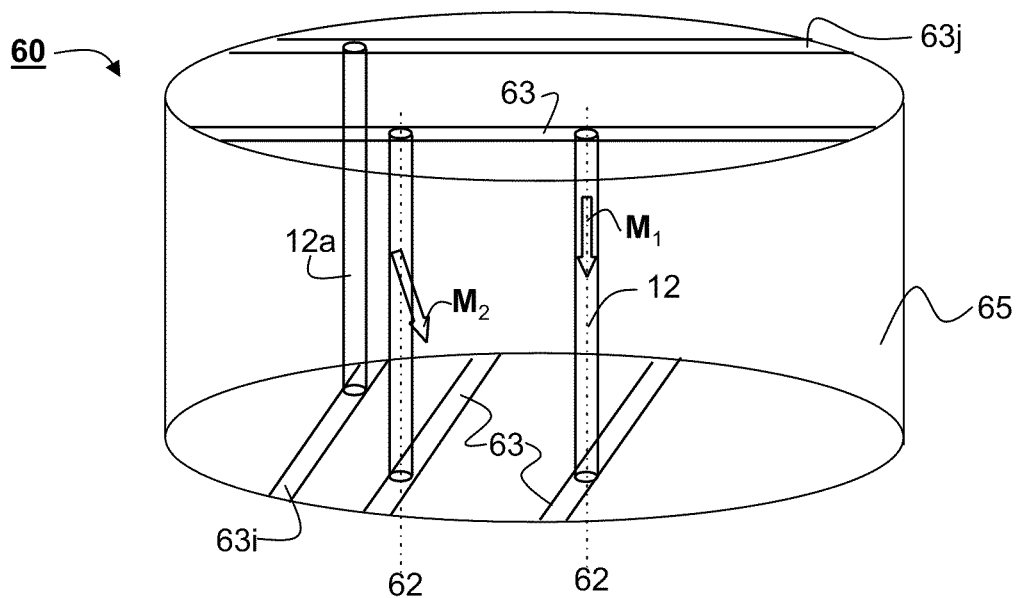
FIG. 8 is a schematic illustration of a memory cell, based on magnetic nanowires, according to a preferred embodiment of the present invention.

Reference is now made to FIG. 8, which is a schematic illustration of a memory cell, generally referred to herein as cell 60. Cell 60 comprises a plurality of nanowires 12, each formed of a ferromagnetic material enclosed by a peptide nanostructure, as further detailed herein above. Nanowires 12 are capable of assuming two magnetization states. One magnetization state (designated $M_1$ in FIG. 8) may be defined, for example, when the magnetization vector, M, is substantially parallel to a longitudinal axis 62 of nanowires 12 and another magnetization state (designated $M_2$ in FIG. 8 may be when the magnetization vector has a non-negligible angle (say, above) 10° with respect to axis 62.

Thus, binary information can be stored by the two magnetization states of nanowires 12. For example, state $M_1$ can be defined as "0" and state $M_2$ can be defined as "1". One ordinarily skilled in the art would appreciate that well separated magnetization states, also known as a magnetization jump, can be obtained and reproduced precisely from one nanowire to the other by working with nanowires of ferromagnetic materials. The jump from one magnetization state to the other is preferably identified by sweeping an external magnetic field, so that when its magnitude is below a proper threshold, characteristic to the ferromagnetic material and structure of nanowires 12, nanowires 12 assumes the first magnetization state and when the magnitude of the external magnetic field magnitude is above the characteristic threshold, nanowires 12 assumes the second magnetization state.

Cell 60 further comprises a plurality of conductive lines 63, preferably arranged on opposite sides of a membrane 65, such that each nanowire of plurality of nanowires 12 is connected to two conductive lines of plurality of conductive lines 63. This allows for a unique address, represented by a pair of gridwise numbers, to be assigned to each individual nanowire. For example, referring to FIG. 8, nanowire 12a, which is connected to conductive lines 63i and 63j is represented by the address (63i, 63j).

The operation of cell 60 is based upon a physical effect known as the anisotropic magnetoresistance effect, according to which a component of the electrical resistance of a magnetic element varies with a change in the magnetization orientation of the element and the sensing current flowing therethrough. The change in the electrical resistance depends on the angle between the magnetization vector and the electrical current.

Specific methods of writing and reading information into and out of cell 60 can be found, for example, in U.S. Pat. No. 6,172,902 the contents of which are hereby incorporated by reference.

Generally, the writing processes to a given address, say, address (63i, 63j), is preferably done by injecting a pulsed current into the respective pair of conductive lines, when the magnitude of the external magnetic field is lower by an amount of ΔH than the characteristic threshold $H_s$. The result of the pulse is to induce the jump from the magnetic state "0" to state "1". The reading process at a given address is preferably done by injecting a current and measuring the potential between the respective pair of conductive lines at a value of the external magnetic field which is between $H_s$-ΔH and $H_s$. Due to the magnetoresistive property of nanowire 12, the value of the electric potential is shifted.

According to another aspect of the present invention, there is provided an electronic device, for switching, inverting or amplifying, generally referred to as device 50.

Figure 9A:
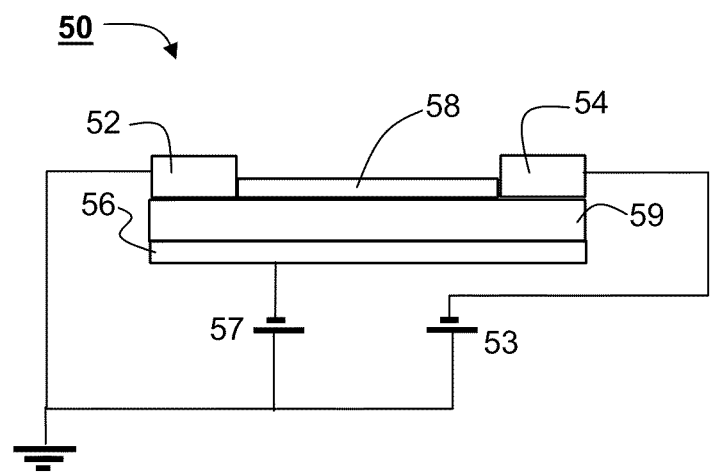
FIG. 9a is a schematic illustration of an electronic device for switching, inverting or amplifying, according to a preferred embodiment of the present invention.

Reference is now made to FIG. 9a, which is a schematic illustration of device 50. Device 50 comprises a source electrode 52, a drain electrode 54, a gate electrode 56 and a channel 58. One or both of gate electrode 56 and channel 58 may be formed of a semiconducting material enclosed by a nanostructure (e.g., nanostructure 12, which can be a conductive or a semi-conductive nanowire or a nanostructure encapsulating a conducting or a semi-conducting material) which is composed of a plurality of peptides, as further detailed hereinabove. For example, in one embodiment channel 58 is a nanostructure and gate electrode 56 is preferably layer of $SiO_2$ in a silicon wafer.

In its simplest principle, device 50 operates as a transistor. Channel 58 has semiconducting properties (either n-type or p-type semiconducting properties) such that the density of charge carriers can be varied. A voltage 57 is applied to channel 58 through gate electrode 56, which is preferably separated from channel 58 by an insulating layer 59. When the voltage of gate electrode 56 is zero, channel 58 does not contain any free charge carriers and is essentially an insulator. As voltage 57 is increased, the electric field caused thereby attracts electrons (or more generally, charge carriers) from source electrode 52 and drain electrode 54, so that channel 58 becomes conducting.

Thus, device 50 serves as an amplifier or a switching device where, voltage 57 of gate electrode 56 controls the current flowing from source electrode 52 and drain electrode 54, when a bias voltage 53 is applied therebetween.

Figure 9B:
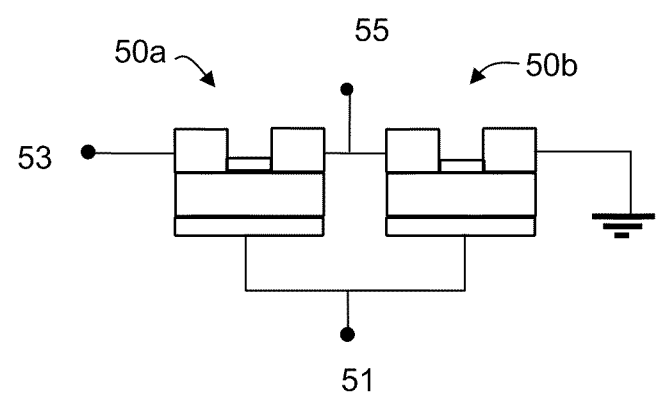
FIG. 9b is a schematic illustration of an inverter, which is formed from two devices, each similar to the device of FIG. 9a, according to a preferred embodiment of the present invention.

Two devices like devices 50 may be combined so as to construct an inverter. Referring to FIG. 9b, in this embodiment, a first such device (designated 50a) may include a channel having an n-type semiconducting properties and a second such device (designated 50b) may include a channel having an p-type semiconducting properties. Devices 50a and 50b are preferably connected such that when bias voltage 53 is applied between the source of device 50a and the drain of device 50b, the combined device serves as an inverter between input signal 51 and output signal 55.

Following are several aspects of the present invention in which nanostructure 12, which can be a conductive or a semi-conductive nanowire or a nanostructure encapsulating a conducting or a semi-conducting material, is primarily exploited for performing mechanical tasks.

According to an additional aspect of the present invention, there is provided a mechanical transmission device, generally referred to herein as device 60.

Figure 10:
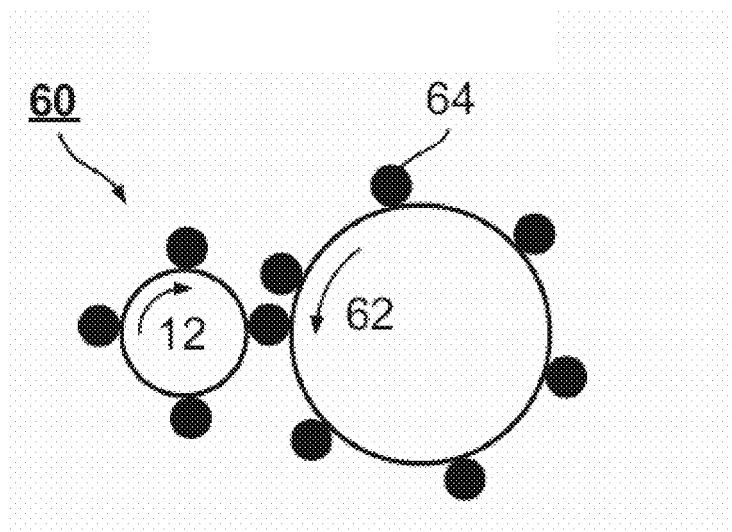
FIG. 10 is a schematic illustration of a mechanical transmission device, according to a preferred embodiment of the present invention.

Reference is now made to FIG. 10, which is a schematic illustration of device 60, according to a preferred embodiment of the present invention. Device 60 comprises a first nanostructure 12 and a second nanostructure 62, which, as stated are composed of a plurality of peptides. First 12 and second 62 nanostructures are operatively associated there amongst such that a motion of first nanostructure 12 generates a motion of second nanostructure 62. Both first 12 and second 62 can have any shape suitable for transmitting motion, such as, but not limited to, a tubular, a spherical, a planar or a fibrillar shape. To facilitate the operative association, one or more molecules 64 (e.g., antibodies, ligands, DNA, RNA, or carbohydrates) can be attached to the external surface of first 12 and/or second 62 nanostructures.

Hence, device 60 can operate as a nanomachine which could self-repair or adapt to the environment. Preferably, first 12 and/or second 62 nanostructures include oppositely charged atoms on their antipodes, so that an electric field can generate a circular motion. Being of a nanometric size, an extremely small magnitude of electric field is sufficient for rotating the nanostructures, in an extremely large angular velocity, typically in the Giga-Hertz range.

Figure 11:
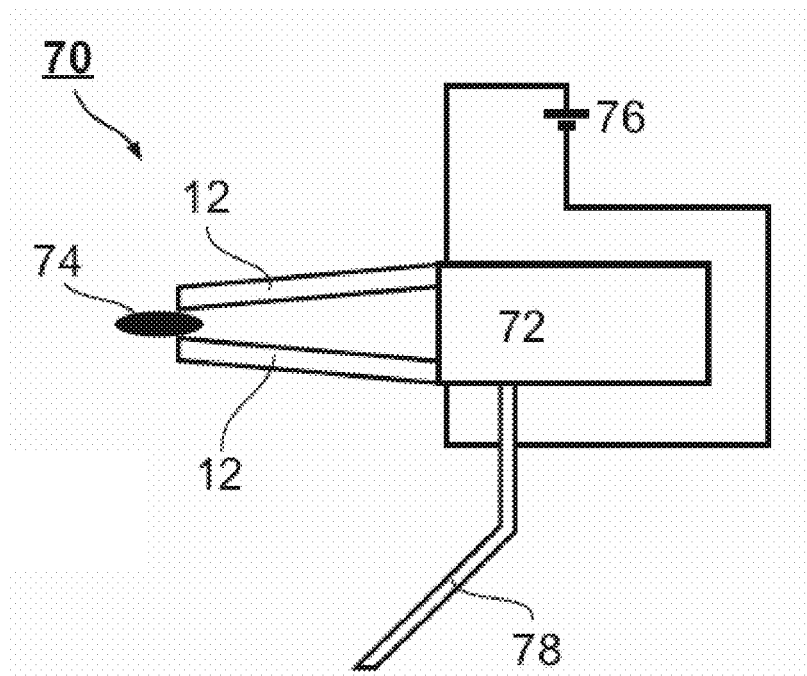
FIG. 11 is a schematic illustration of a nanoscale mechanical device for griping and/or manipulating objects of nanometric size, according to a preferred embodiment of the present invention.

Another mechanical application in which nanostructure 12 can be used is illustrated in FIG. 11. In this aspect of the present invention nanostructure 12 is exploited for the purpose of manipulating nanoscale objects. A potential application of the present aspect of the invention is in the area of assembling nanoelectronic circuit (see, e.g., cell 40 or device 50 hereinabove) when nanoscale objects are to be precisely located in a predetermined location.

FIG. 11 illustrates a nanoscale mechanical device 70, which comprises at least one nanostructure 12 designed and configured for grabbing and/or manipulating a nanoscale object 74. Such operation may be achieved, for example, using two nanostructures 12, preferably tubular nanostructures, mounted on a mounting device 72, whereby nanostructures 12 perform a constrained motion to grab object 74.

Mounting device 72 can be, for example, a tip end of an atomic force microscopy cantilever, so that one or both of nanostructures 12 can also be utilized as an atomic force microscopy probe. In use, nanostructures 12 first scan (e.g., as an atomic force microscopy probe) the region where object 74 is expected, thus confirming the position and shape thereof. This scan me be performed in any method known in the art, such as, but not limited to, using a three-dimensional driving mechanism 78.

The motion of nanostructure 12 may be controlled, for example, by a voltage source 76 which generates an electrostatic force between nanostructures 12. Thus, by activating voltage source 76 nanostructures 12 can close or open on object 74.

Once nanostructure 12 grip object 74, which, as stated, has been marked by the atomic force microscopy procedure, mounting device 72 can be moved by three-dimensional driving mechanism 78, to a desired location. Subsequently nanostructures 12 are further opened, thus releasing object 74 in its appropriate location. In cases where object 74 fails to separate from nanostructures 12, e.g., due to Van der Waals forces between object 74 and nanostructures 12, a further voltage can be applied between nanostructures 12 and the desired location, so that object 74 is released by an electrostatic attractive force.

As stated, the nanostructure of the present invention can also be used for reinforcing other materials, such as, but not limited to, polymers. Thus, according to yet an additional aspect of the present invention there is provided composition, in which a polymer is combined with the nanostructure of the present invention. Preferably, the nanostructure is chemically bonded to or integrated within the polymer chains via one or more chemical bond types.

Several attachment configurations can be utilized in order to reinforce polymer chains.

For example, the nanostructure can be linked to one or more chain-terminating group of the polymer chain or to residues of internal polymer groups. The polymer component of the composition of the present invention preferably comprises polymers, including copolymers, which are capable of chemically bonding with the peptides of the nanostructure, or those polymers that can be prepared from one or more monomer precursors capable of bonding with the peptides of the nanostructure either prior to or during polymerization. Representative examples of polymers which may be used include without limitation polyethylene glycol (PEG), polysaccharides, DNA, RNA, poly amino-acids, peptide nucleic acid (PNA).

The composition described above, can be used for manufacturing many forms of articles, such as filaments, carpets, ropes and the like.

A fiber can be formed from the polymer-nanostructure composition by cutting the composition into chips and drying. These chips can then be heated under pressure to bond the chips into a plug. This plug can then be heated to a molten state, passed through a mesh screen, and forced through an extrusion orifice. The filament formed by the molten composite material can then be pulled away from the orifice and wound onto a bobbin. Such fibers can be incorporated into bulked continuous filament, and made into carpets, ropes and the like.

Alternatively, the composition describe above can be used as an injection moldable resin for engineering polymers for use in many applications, such as, but not limited to, filters, solenoids and the like.

The nanostructure of the present invention can also be dispersed throughout a matrix material to thereby form a free-form structure. Constructing and arranging composite nodal elements to define a structure circumvents the common practice in the industry of post-fabrication processing operations. Initially, a structure is often fabricated in a mold or by machining and then subjected to post-fabrication processing operations. Post-fabrication processing operations refer to added steps required beyond initial fabrication so that the structure exhibits desired dimensions and tolerance. Typically, post-processing operations include for example, among others, machining, cleaning, polishing, grinding, deburring and hole drilling so as to achieve desired dimensions and tolerance of a fabricated structure.

Following is a description of an additional embodiment of the present invention in which the nanostructures are used for the purpose of delivering energy from one location to the other.

In many industries, there is a great need for more efficient heat transfer fluids. Heat transfer fluids used in today's conventional thermal systems have inherently poor heat transfer properties. Often, millimeter- or micrometer-sized particles are suspended in heat transfer fluids so as to increase the capability of the fluid to deliver heat. The ratio of surface area to volume of the nanostructure of the present invention is about three orders of magnitudes larger than that of micrometer-sized particles. Since heat transfer occurs on the surface of a fluid, this feature of the present invention can be used for significantly enhancing heat conduction properties of cooling fluids.

Thus, according to a further aspect of the present invention there is provided, a nanofluid, comprising the nanostructures of the present invention suspended in a fluid. The nanofluid of the present invention is characterized extreme stability and ultra-high thermal conductivity.

The present invention successfully provides a heat transfer device 80 which exploits the above mentioned thermal properties of the nanofluid.

Figure 12:
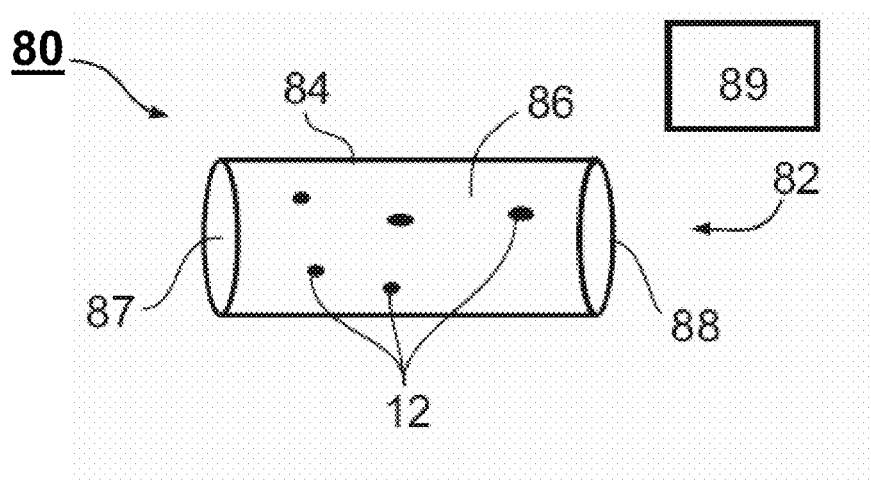
FIG. 12 is a schematic illustration of a heat transfer device, according to a preferred embodiment of the present invention.

Reference is now made to FIG. 12, which is a schematic illustration of device 80. Device 80 comprises a nanofluid 82 and a channel 84 for holding nanofluid 82. As stated, nanofluid 82 comprises nanostructures 12 suspended in a fluid 86, where at least a portion of nanostructures 12 is composed of a plurality of peptides, as further detailed hereinabove and in accordance with the present invention. Channel 84 is preferably constructed such that heat is transferred by nanofluid 82, and, in particular, by nanostructure 12, from a first end 87 to a second end 88 of channel 84.

Channel 84 is preferably in a micrometer size (i.e., a microchannel) or a nanometer size (i.e., a nanochannel), both are known in the art. In the embodiment in which channel 84 is a nanochannel, the diameter thereof is larger that the diameter of the largest nanostructure, so as to allow nanofluid 82 to flow freely through channel 84.

Device 80 may further comprise a locomotion system 89 for generating locomotion of nanofluid 82 within channel 84. System 89 may operate in any way known in the art for generating locomotion of nanofluid 82. For example, in one embodiment, the locomotion of nanofluid 82 can be achieved by an under-pressure formed in channel 84, in which case system 89 generates under-pressure. In another embodiment, fluid locomotion can be achieved by dielectrophoretic forces applied thereon, in which case system 89 can be realized, for example, as a mechanism for generating a non-uniform electric field.

Following is a description of additional embodiments of the present invention in which the nanostructures described hereinabove are coated by a conducting shell to form the nanoshell further detailed hereinabove.

Hence, according to yet another aspect of the present invention there is provided a composition for modulated delivery of a chemical to a predetermined location. The composition comprises a plurality of nanoshells, each nanoshell having a nanostructure core and a conductive shell which is capable of converting incident radiation into heat energy. The nanostructure core is composed of a plurality of peptides, as further detailed hereinabove. The composition further comprises a medium having the chemical and a thermally responsive material (e.g., a thermally responsive hydrogels) in thermal contact with the nanoshells.

Composites of thermally responsive hydrogels are known in the art. For example, copolymers of N-isopropylacrylamide (NIPAAm) and acrylamide (AAm) exhibit a lower critical solution temperature (LCST) that is slightly above body temperature. When the temperature of the copolymer exceeds the LCST, the hydrogel collapses, causing a rapid release or burst of any soluble material held within the hydrogel matrix.

The nanoshells serve as heat transfer agents within the polymer matrix. Each of the nanoshells may also include a targeting component, such as an affinity component having an affinity to the cells in the location of interest. Being of nanometric diameter, the nanoshells have well defined wavelength absorbance maxima across the visible and infrared range of the electromagnetic spectrum. Preferably, the conductive shell of the nanoshells is made of gold. A gold shell can be fabricated, for example, by seeding the amine groups of the nanostructure core with colloidal gold; additional colloidal gold is added via chemical reduction in solution, to form the gold shell layer.

The wavelength of maximum optical absorption of each nanoshell is determined by the ratio of the core radius to the shell thickness. Each of these variables (core radius and shell thickness) can be independently controlled during fabrication of the nanoshells. Varying the shell thickness, core diameter, and the total diameter of the nanoshell, allows the optical properties of the nanoshells to be tuned over the visible and near-infrared spectrum.

In order to convert light energy into heat, administered nanoshells are exposed to light at an appropriate wavelength (e.g., 800-1200 nm) which is transmitted through tissue. The generated heat causes collapse of the hydrogel in the vicinity of the nanoshell causes significantly enhanced release of chemicals and proteins of varying molecular weight from the new composite hydrogels.

Since it is capable of converting light energy into heat, the nanoshell of the present invention can be used to induce localized hyperthermia in a cell or tissue of an individual and thus can be utilized as therapeutic agent in treatment of various diseases such as hyperproliferative diseases, as detailed hereinbelow.

For example, an individual having cancer can be administered with a therapeutic effective amount of the nanoshells of the present invention using a suitable administration route and thereafter exposed to electromagnetic radiation in the resonance frequency of the nanoshells, e.g., using a continues wave or pulse laser device, for a time period of, say, about 5-30 minutes to thereby convert the electromagnetic radiation into heat energy. The generated heat may is preferably sufficient to perform therapeutic treatment, e.g., to kill the cells, if so desired.

Preferably, the electromagnetic radiation is in the near infrared range. Such radiation is advantageous for its ability to penetrate tissue. Other types of radiation can also be used, depending on the selection of the conductive shells and the targeted cells. Examples include x-rays, magnetic fields, electric fields and ultrasound.

As stated, the method may be used for destroying living cells. In this embodiment, each of the nanoshells may include an affinity component having affinity to the living cells to be destroyed. Thus, the present invention can be used to treat many types of cancers, such as, but not limited to, vaginal cancer, vulvar cancer, cervical cancer, endometrial cancer, ovarian cancer, rectal cancer, salivary gland cancer, laryngeal cancer, nasopharyngeal cancer, many lung metastases and acute or chronic leukemia (e.g., lymphocytic, Myeloid, hairy cell).

According to a preferred embodiment of the present invention, the affinity component of the nanoparticles includes a moiety which may be, for example an antibody, an antigen, a ligand or a substrate.

The following lists primary antibodies known to specifically bind their associated cytological markers and which are presently employed as affinity components in immunohistochemical stains used for research and, in limited cases, for diagnosis and therapy of various diseases. Anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oncoprotein (p21) antibody, anti-Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (Alzheimer's disease), anti-fibrin antibody (epithelial cells), anti-keratins antibody, and anti-Tn-antigen antibody (colon carcinoma, adenocarcinomas, and pancreatic cancer).

Other applications of the nanostructures of the present invention include use thereof in biomedical sciences and in biotechnology such as their use as vehicles for enzyme encapsulation [Chang (2001) Mol. Biotechnol. 17:249-260], DNA transfection [Kneuer (2000) Bioconj. Chem. 11:926-932; Rader (1997) Science 810-814; Koltover (1998) Science 281: 78-81], scaffolds for tissue building, biosensors [Cao (2002) Science 297:1536-1540; Demers (2002) Science 296:1836-1838; Park (2002) Science 295:1503-1506] and drug delivery [Ulrich (1999) Chem. Rev. 99:3181-3198; Lee (2002) Biomacromolecules 3:1115-1119; Murthy (2002) J. Am. Chem. Soc. 124:12398-12399]. For example, drugs can be incorporated onto the biodegradable nanospheres of the present invention, to thereby allow for timed release of the drug as the nanosphere degrades. The conditions which allow degradation can be adjusted by varying the chemical bonding within the nanostructure. For example, when acid-labile bonds are used, the nanostructures of the present invention will degrade in an acidic environment such as would exist in a site of inflammation or in tumor cells. Alternatively, the nanostructures of the present invention can be coated with viral peptide sequences which promote membrane-permeation. Finally, surface functionalized nanostructures of the present invention can also be used to deliver genetic material into living cells (i.e., transfection).

In any of the above embodiments, the nanostructures can be coated by any suitable material, e.g., a conductive material (as in the case of the nanoshells), a semiconductive material or a dielectric material, and can be bounded to other molecules to achieve desired electrical, mechanical, chemical or biological properties. For example, the nanostructures of the present invention can be coated by silver, gold and other conductive materials.

Figure 13A:
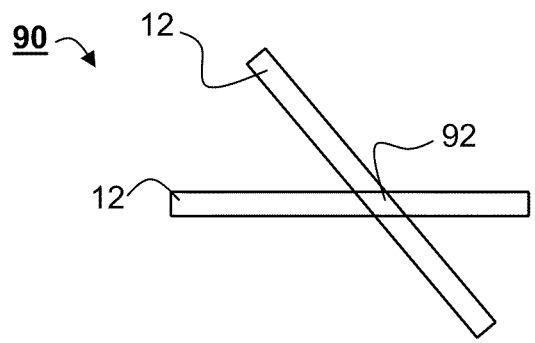
FIG. 13a is a schematic illustration of a transistor, formed of two nanowires, according to a preferred embodiment of the present invention.

An additional configuration which includes semiconducting nanowire is illustrated in FIG. 13a. In this embodiment, two nanowires 12 forming a junction 92 can serve as a transistor 90. Preferably, the semiconducting material of one of the two nanowires has an n-type doping and the semiconducting material of the other nanowire has a p-type doping.

In accordance with the present invention, one or both of nanowires 12 of transistor 90, has a modulation-doped semiconductor material. This may be achieved by providing a nanowire having either Lewis acid functional groups or Lewis base functional groups to create a region of modulation doping in the junction. One of nanowires 12 comprises the source and the drain portions of transistor 90 and the other nanowire induces the gate function at junction 92. Both pnp and npn transistors that are analogous to bipolar transistors may be formed in this fashion.

Several junctions like junction 92 can be allocated to form a crossbar array 94, which can be used for signal routing and communications between two layers of nanowires. According to the presently preferred embodiment of the invention crossbar array 94 comprises a two-dimensional array of a plurality of junctions similar to junction 92. Each junction servers as a switch which can be either singly configurable or reconfigurable and self-assembling. In one embodiment, at least one of the junctions is a quantum state molecular switch having an electrically adjustable tunnel junction between the respective two nanowires. The switches, formed at each junction, can be electrochemically oxidized or reduced. Oxidation or reduction of the molecule forms the basis of a switch. Oxidation or reduction affects the tunneling distance or the tunneling barrier height between the two nanowires, thereby exponentially altering the rate of charge transport across the junction.

Figure 13B:
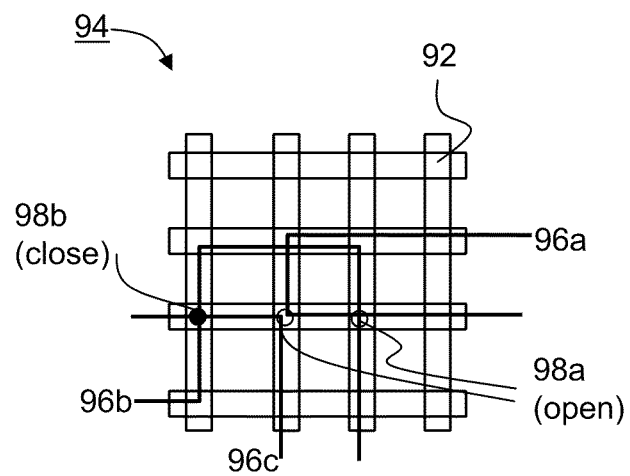
FIG. 13b is a schematic illustration of an array of junctions, each defined between two nanowires, according to a preferred embodiment of the present invention.

Reference is now made to FIG. 13b which is a simplified illustration of array 94. Array 94 comprises a plurality of junctions 92 defined when two nanowires 12 are crossed at some non-zero angle. Nanowires 12 can be formed of a conducting or semiconducting material enclosed by a peptide nanostructure, as further detailed hereinabove. When an appropriate voltage is applied across the nanowires, molecules of each of the two nanowires at the junction point are either oxidized or reduced. When a molecule of one nanowire is oxidized, then a molecule of the other nanowire is reduced so that charge is balanced. These two species are referred to herein as a redox pair.

Distinct electrical circuits 96a and 96b and 96c may be created in array 94 as part of an integrated circuit. Circuits 96a, 96b and 96c can cross each other without being electrically connected where switches, shown as open circles in FIG. 13b and designated 98a, are open. Alternatively, nanowires may be electrically connected by a closed switch, shown as a filled circle in FIG. 13b and designated 98b. By using the voltage across the electrochemical cell formed by each pair of crossed nanowires to make and break electrical connections both along nanowires in a layer (segmented wires) and between wires in two layers (vias), one can create an integrated circuit of arbitrarily complex topology. The wires may connect to an external or an internal electronic device (not shown), e.g., a resonant tunneling diode or a transistor.

This freedom to select a mixture of device types and interconnect topologies includes the possibility that nanowires 12 are heterogeneous in their composition or functionalization. The nanowires in a given layer can be separately formed and functionalized in a plurality of different ways, and subsequently assembled to form a layer that is heterogeneous in nanowire type.

The conducting nanowires of the present invention can also serve as conducting interconnects for electronic circuit assembly of multiple layers. Multi-layered electronic assemblies are used to interconnect a large number of circuit layers. A typical multi-layered assembly has several layers of signal lines, separated by interleaving dielectric layers, and via connections running through one or more dielectric layers perpendicular to the layers surface, as required by the specific electric interconnect network of the assembly.

Figure 14:
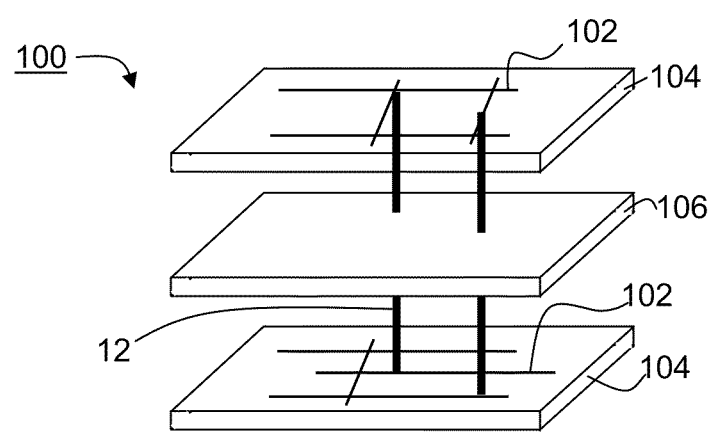
FIG. 14 is a schematic illustration of an electronic circuit assembly, according to a preferred embodiment of the present invention.

Reference is now made to FIG. 14, which is a simplified illustration of an electronic circuit assembly 100, according to a preferred embodiment of the present invention. Assembly 100 comprises conductive lines 102 being arranged in at least two layers 104 separated therebetween by a dielectric layer 106. Several conductive lines 102 are electrically connected via one or more conductive nanowire 12. Nanowires 12 preferably serve as passive conductors for facilitating electrical communication between different layers of assembly 100.

As used herein, the phrase passive conductor refers to a conductor capable solely to transmit electrical current therethrough.

As used herein, the phrase dynamical conductor referrers to a conductor capable of having to states: a transmissive state in which the conductor serve as a passive conductor and a non-transmissive state in which no electrical current is transmitted therethrough.

It will be appreciated that assembly 100 can be combined also with array 94 or several elements thereof, so that nanowires 12 can also be used dynamically. For example, some nanowire can serve mealy as vertically conductive lines between different layers (passive conductors), while other nanowires may form one or more junctions, similar to junction 92, thus allowing switching (dynamic conductors) as further detailed hereinabove.

An additional application in which the nanowires of the present invention can used is in a device for detecting a position and/or movement of an object. Position sensors are used in a variety of modem devices and transducers, for example, in applications for robotics and computer hardware. In robotics, such sensors provide useful information about the state of contact between a robot hand and an object in prehension. In computer-related products such sensors are employed in device such as, but not limited to, mouse, joystick and the like, which respond to movement in two dimensions.

Figure 15A:
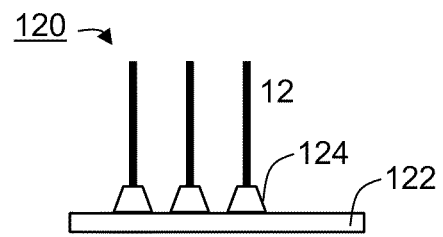
FIGS. 15a-b are schematic illustrations of a device for detecting a position and/or movement of an object, according to a preferred embodiment of the present invention.

Reference is now made to FIG. 15a, which is a simplified illustration of a device for detecting a position and/or movement of an object, generally referred to herein as device 120. Device 120 comprises a plurality of non-intersecting nanowires 12, formed of conducting or magnetic material enclosed by the peptide nanostructure of the present invention. Nanowires 12 are connected to an electronic circuitry 122, which may have a flat surface or a macroscopically non-flat surface, e.g., a robot's finger tips. The connection between nanowires 12 and circuitry 122 may be via an array of contact pads 124. Each contact pad may be allocated with more than one nanowire so as to form a bundle of nanowires.

Figure 15B:
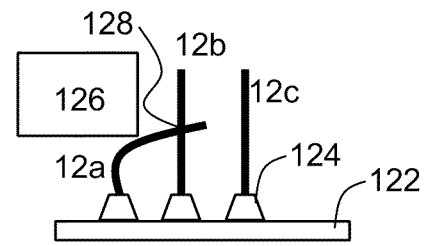

FIG. 15*b* is a schematic illustration of device 120 when contacted by an object 126. Three nanowires are shown in FIG. 15*b*, designated 12*a*, 12*b* and 12*c*. In operational mode, object 126 contacts nanowire 12*a* and elastically bends it so that nanowire 12*a* intersects nanowire 12*b* which is adjacent thereto. An electrical connection 128 between nanowire 12*a* and nanowire 12*b* is thus made possible. Similarly, when objects 126 continues to move, other intersections occur (e.g., between nanowires 12*b* and 12*c*).

The location at which object 126 contacts device 120 can thus be detected based on the criterion of electrical connection/no-connection between pairs of contact pads. Device 120 is capable of detecting the position, area, direction of movement, and intensity or strength of the tactile contact (the contact of object 126 with device 120). These factors are generally referred to herein as the position and movement activity of object 126. The position and movement activity can be evaluated by interrogating pairs of contact pads to determine whether an electrical connection has been made between adjacent nanowires.

Whether a connection between nanowires 12 has been made can be sensed by sending a current pulse to contact pads 124 and measuring the electrical resistance. The location of the object can be determined quantitatively based on the number of nanowire being electrically connected at any moment. The time sequence at which the electrical connections are effected provides information on the direction of the motion of object 126. Contact pads 124 can be interrogated sequentially or simultaneously to detect the electrical connection.

The intensity of the tactile force on device 120 may be determined in various ways, such as, but not limited to, evaluation of the physical contact resistance between nanowires that are bent and in contact. The value of the electrical resistance between connected depends on the force applied on nanowire 12.

The conducting or semiconducting nanowires of the present invention may also be used in the field of electrophoretic displays. As stated in the background section that follows, electrophoretic displays employ a plurality of electrically charged particles suspended in a fluid. Under the influence of electric field, the charged particles move through the fluid hence locally alter the optical characteristics of the display.

According to an additional aspect of the present invention there is provided a display system, generally referred to herein as system 130.

Figure 16:
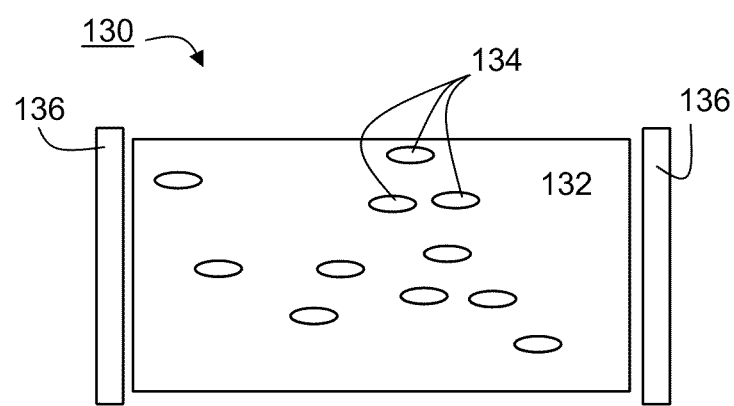
FIG. 16 is a schematic illustration of a display system, according to a preferred embodiment of the present invention.

Reference is now made to FIG. 16 which is a schematic illustration of system 130. System 130 comprises a fluid 132 containing a plurality of nanostructure devices 134, each being formed of a conducting or semiconducting material enclosed by a peptide nanostructure, as further detailed hereinabove.

Nanostructure devices 134 are distinguished from the pigment particles used in prior art electrophoretic displays by their size. Pigment particles are typically of the order of several hundred nanometers in diameter, or larger. Thus, the diameters of even the smaller pigment particles are of the same order as the wavelengths of visible light, which vary from about 400 nm for blue light to about 700 nm for red light. It is well known to those skilled in the art that the light scattering power of particles is approximately proportional to the sixth power of the particle diameter for particles having diameters less than the wavelength of the relevant light.

Thus, isolated nanostructure devices, which are much smaller than the typical wavelength of light do not appreciably scatter the light and, as such, are effectively transparent. However, the nanostructure devices, when brought into proximity with one another and thus aggregated into larger clusters having diameters comparable to the wavelength of light, scatter light strongly. Thus, by controlling the aggregation level of nanostructure devices 134, one can determine whether the nanostructure devices 134 appear transparent or turbid.

System 130 further comprises an electric field generator 136 capable of generating an electric field effective in shifting nanostructure devices 134 between a dispersed state, corresponding to a first optical characteristic and an aggregated state corresponding to a second optical characteristic.

Conducting nanostructure devices, such as peptide nanostructure encapsulating silver or gold, change color with aggregation. This color change is due to the change in the average refractive index as the aggregates form. When conducting nanostructure devices aggregate, both the color and the intensity of light scattering increases. In other words, the first and second optical characteristics of the display system comprise different colors. For example dispersions of gold nanostructure devices are typically ruby red, while aggregates of gold nanostructure devices vary in color from purple to blue to black depending on the interparticle distance. Thus, in this embodiment, the color of system 130 can be controlled by controlling the degree of aggregation of nanostructure devices 134.

Semiconducting nanostructure devices have strong particle size dependent colors in both the dispersed and aggregated states. The colors are best and most easily seen in fluorescence, and are due to the size dependent quantization of electronic levels in nanostructure devices 134. The smaller the nanostructure device, the larger the band gap and the shorter the wavelength of the fluorescence. Semiconducting nanostructure devices have fluorescent peaks that vary smoothly from about 400 nm to about 700 nm (red) when the size of the nanostructure device varies from about 1.2 nm to about 11.5 nm.

An additional application in which the peptide nanostructures of the present invention can be useful is in the field of thermoelectricity. Thermoelectric devices are devices that either convert heat directly into electricity or transform electrical energy into pumped thermal power for heating or cooling. Such devices are based on thermoelectric effects involving relations between the flow of heat and of electricity through solid bodies.

The formulation of the thermoelectric effect, also known as the Seebeck effect, is as follows. When an open circuit made of a pair of dissimilar metals is held so that two junctions are kept at different temperatures, a potential difference is produced across the terminals of the open circuit. The potential difference is directly proportional to the temperature difference, and does not depend on the distribution of temperature along the metals between the junctions. The factor of proportionality, referred to in the literature as the relative Seebeck coefficient, generally varies with the level of the temperature at which the temperature difference occurs.

The flip side of the Seebeck effect is known as the Peltier effect. According to the Peltier effect a current driven in a circuit made of dissimilar metals causes the different metals to be at different temperatures. Depending on the direction of current flow, heat could be either removed from a junction to freeze water into ice, or by reversing the current heat can be generated to melt ice. The heat absorbed or created at the junction is proportional to the electrical current, and the proportionality constant is known as the Peltier coefficient. The Peltier effect is caused by the fact that an electrical current is accompanied by a heat current in a homogeneous conductor even at constant temperature. The heat current is interchangeably referred to herein as power, as the two quantities have the same physical dimensions (energy per unit time).

The heat current accompanying the electric current, I, is explained by the different flow velocities of the electrons carrying the electric current. The flow velocities depend on the energies of the conduction electrons. For example, if the flow velocity of electrons having an energy above the Fermi energy is higher than for electrons with a lower energy, the electric current is accompanied by a heat current in the opposite direction (since the electronic charge is negative). In this case the Peltier coefficient is negative. Similar situation occurs in an n-doped semiconductor where the electric current is carried by electrons in conduction-band states. Opposite situation (i.e., electrical and heat currents flowing in parallel direction) occurs for a p-doped semiconductor where the electric current is carried by holes.

The operation of thermoelectric devices is based on the Peltier effect. Generally, thermoelectric devices have thermoelectric materials sandwiched between ceramic plates. When the plates have different temperatures (due to the current flowing therebetween) and the heat at the hot plate is dissipated to the ambient environment, this assembly becomes a cooling unit.

Besides the pumping of heat away from the cold plate, there exists two additional thermal processes, which conflict with the Peltier cooling: Joule heating, originating from the electromotive source generating the electrical current, and heat conduction current, flowing from high to low temperatures. The coefficient-of-performance of the cold plate of a thermoelectric device is defined as the ratio of the power at the cold plate, to the total power of the device. The figure-of-merit of the thermoelectric device is defined as $S^2 \sigma T/\kappa$, where S is the Seebeck coefficient, $\sigma$ is the electrical conductivity, T is the temperature and $\kappa$ is the thermal conductivity of the device. An efficient thermoelectric device is characterized by high coefficient-of-performance and high figure-of-merit.

As the Seebeck coefficient, S, and the electrical conductivity, $\sigma$, are competing quantities, any attempt to increase the Seebeck coefficient, results in a decrement of the electrical conductivity. It is therefore appreciated that in conventional materials, a limit to the figure-of-merit is rapidly obtained. Moreover, for a given thermoelectric device, designed for a specific application at a specific range of temperatures, the power of the cold plate and the coefficient-of-performance reach their maximal values at different currents. Practically in conventional thermoelectric devices the current is compromisingly selected in the range between the maximum efficiency and the maximum cooling power.

Hence, the temperature difference between the hot and the cold plates imposes severe limitations on the efficiency of the device. Moreover, even for low temperature differences, in many applications, especially for cooling of small areas, conventional thermoelectric devices are not capable of pumping the required heat fluxes.

The use of low dimensions in the design of thermoelectric devices, is known to have several advantages: (i) enhanced density of states, due to quantum confinement effects, results in an endearment of the Seebeck coefficient without a reduction in the electrical conductivity; and (ii) boundary scattering of electrons or holes reduces the thermal conductivity more than the electrical conductivity, hence further increases the figure-of-merit.

Being practically a one dimension object, the peptide nanostructure of the present invention can be employed in thermoelectric devices. The thermoelectric devices of the present invention can be used in numerous areas of applications, such as, but not limited to, military, medical, industrial, consumer, scientific/laboratory, electro-optics, computers and telecommunications areas. For example, in communications systems, the thermoelectric devices of the present invention can be used keep power amplifiers of transceivers at operating temperature. In the area of laser devices and, more particularly, semiconductor laser devices, the thermoelectric devices of the present invention can be used for transporting heat away from small areas, thereby to control the operating temperature of the semiconducting laser device. Additionally, the thermoelectric devices of the present invention can be used to stabilize temperature in multiplexed fiberoptics communications systems, where heat generation and thermal management is becoming one of the barriers to further increase clock speeds and decrease feature sizes. Still in addition, the thermoelectric devices of the present invention can be used in microprocessors and digital signal processors, where a very small area of high heat must be removed quickly and efficiently.

Thus, according to a yet additional aspect of the present invention, there is provided a thermoelectric device 140.

Figure 17:
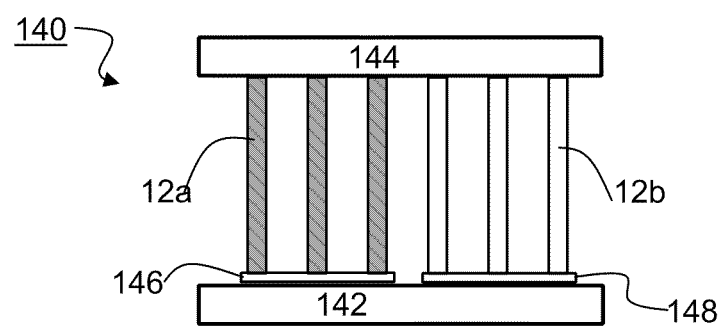
FIG. 17 is a schematic illustration of a thermoelectric device, according to a preferred embodiment of the present invention.

Reference is now made to FIG. 17 which is a schematic illustration of device 140. Device 140 comprises a first heat conducting layer 142 and a second heat conducting layer 144, where first 142 and second 144 heat conducting layers are interposed by a plurality of nanowires 12. Nanowires 12 are formed of a thermoelectric material encapsulated by the peptide nanostructure of the present invention, as further detailed hereinabove.

It is recognized that the efficiency of thermoelectric device 140 is increased by decreasing the leg diameter to a size at which quantum confinement effects occur. Thus, by using nanowires 12 of the present invention, the performance efficiency is substantially increased. More specifically, because the charge carrier mobility in nanowires 12 is enhances due to quantum confinement effects present therein, the Seebeck coefficient is increased substantially without a decrease in the conductivity of the device.

According to a preferred embodiment of the present invention there are two branches of nanowires 12, designated 12a and 12b in FIG. 17. Nanowires 12a are connected to layer 142 through an electrically conductive layer 146 and nanowires 12b are connected to layer 142 through an electrically conductive layer 148. Layer 144 is preferably electrically conductive. Layers 146 and 148 have no electrical communication thereamongst, other than the electrical communication through nanowires 12a, nanowires 12b and layer 144. Nanowires 12a and 12b preferably have opposite doping nature. For example nanowires 12a may be p-type semiconductors and nanowires 12b may be n-type semiconductors or vice versa.

When current flows from an electromotive source (not shown), free electrons flow through nanowires 12b from layer 142 to layer 144, and holes flow through nanowires 12a from layer 144 to layer 142. In the following, the operation of the 12b branch of device 140 will be explained. One ordinarily skilled in the art would appreciate that a similar description applies also for the second branch, by reversing the sign of the heat and charge carriers, i.e., by replacing electrons with holes.

In operative mode, layer 142 absorbs heat from the environment. The resulting effect is a heat current flowing antiparallel to the electrical current generated by the electromotive source. In other words, the heat (or a portion thereof) is carried by the electrons flowing through nanowires 12b in the direction of plate 144. During the transition of electrons from plate 142 to nanowire 12b, the electrons receive additional energy, sufficient for moving from the Fermi level of free electrons in plate 142 to the conduction band in nanowires 12b. This energy is taken from layer 142 by annihilating phonons in its lattice. Thus, energy is pumped away from layer 142.

When the electrons of nanowires 12b arrive to layer 144, their kinetic energy is delivered thereto, for example, by producing phonons. Thus, energy, originated from layer 142 is transferred to layer 144. Subsequently, the heat is dissipated to the environment, for example with the aid of a heat sink.

Figure 18:
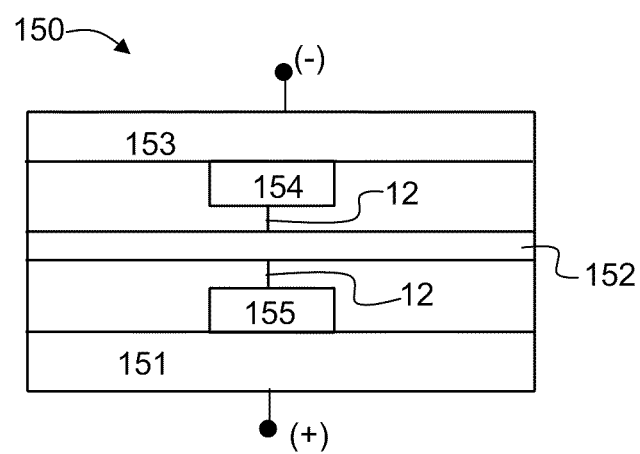
FIG. 18 is a schematic illustration of another thermoelectric device, according to a preferred embodiment of the present invention.

Reference is now made to FIG. 18, which is a schematic illustration of another thermoelectric device, generally referred to herein as device 150. According to a preferred embodiment of the present invention device 150 comprises several three heat conducting regions. Shown in FIG. 18 are three such regions, designated by numerals 151, 152 and 153. Device 150 further comprises two semiconducting regions 154 and 155, which are connected to regions 151, 152 and 153 via two or more nanowires 12. Nanowires 12 are formed of a conducting or thermoelectric material enclosed by the peptide nanostructure of the present invention, as further detailed hereinabove.

Regions 151 and 153 are connected to electromotive sources (not shown), and provide current through device 150. Semiconducting regions 154 and 155 have opposite doping nature. For example region 154 may be a p-type semiconductor and region 155 may be an n-type semiconductor or vice versa. Region 152 serves as the cold part of device 150, while regions 151 and 153 serve as the hot parts thereof. When current passes from region 151 to region 153 though regions 154 and 155 and through nanowires 12, the Peltier effect causes heat to be transmitted out of region 152. Nanowires 12, connecting semiconducting regions 154 and 155 to cold region 152, form quantum cold points. These cold points provide electron confinement and also phonon discontinuity, which limits vibrational energy transfer via the lattice of the materials and hence limits heat transfer from regions 154 and 155 to cold region 152. These effects improve cooling efficiency of the thermoelectric cooling device.

It will be appreciated that the elements of device 150 can, in principle, engage a single plane. In other words, all the components of device 150 can be formed in a lateral orientation, at the same relative height above the substrate onto which they are formed. Such a lateral configuration is easier to fabricate than a top down structure in forming the points because the shape can be precisely controlled.

One of the advantages of the present invention is that the principles of devices 140 or 150 may be exploited for many applications. For example, several thermoelectric devices may be arranged to form a thermoelectric system capable of pumping more heat than a single device. Being preferably small sized, many thermoelectric devices can be efficiently packed into a relatively compact thermoelectric system. In addition, one or more thermoelectric devices (e.g., a thermoelectric system) may be integrated on an object, such as, but not limited to, an electronic chip, so as to facilitate heat release therefrom.

According to yet an additional aspect of the present invention, nanowire 12 can also be used for performing mechanical tasks. For example, nanowire 12 can be used for manipulating nanoscale objects. One potential application of the present aspect of the invention is in the area of assembling nanoelectronic circuit (see, e.g., cell 40, cell 60, device 50 and transistor 90 hereinabove) when nanoscale objects are to be precisely located in a predetermined location.

Figure 19:
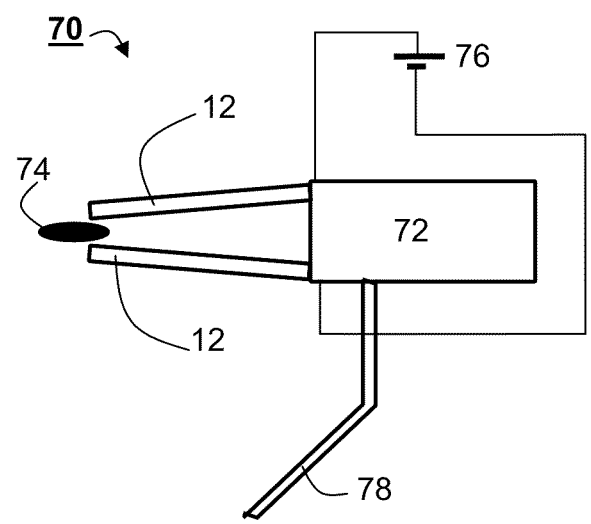
FIG. 19 is a schematic illustration of a nanoscale mechanical device for griping and/or manipulating objects of nanometric size, according to a preferred embodiment of the present invention.

Reference is now made to FIG. 19 which is a schematic illustration of a nanoscale mechanical device 70, which comprises at least one nanowire 12 designed and configured for grabbing and/or manipulating a nanoscale object 74. Nanowire 12 is formed of a conducting material enclosed by the peptide nanostructure of the present invention, as further detailed hereinabove. The operation of device 70 may be achieved, for example, using two nanowires 12, preferably tubular nanowires, mounted on a mounting device 72, whereby nanowires 12 perform a constrained motion to grab object 74.

Mounting device 72 can be, for example, a tip end of an atomic force microscopy cantilever, so that one or both of nanowires 12 can also be utilized as an atomic force microscopy probe. In use, nanowires 12 first scan (e.g., as an atomic force microscopy probe) the region where object 74 is expected, thus confirming the position and shape thereof. This scan me be performed in any method known in the art, such as, but not limited to, using a three-dimensional driving mechanism 78.

The motion of nanowire 12 may be controlled, for example, by a voltage source 76 which generates an electrostatic force between nanowires 12. Thus, by activating voltage source 76 nanowires 12 can close or open on object 74.

Once nanowire 12 grip object 74, which, as stated, has been marked by the atomic force microscopy procedure, mounting device 72 can be moved by three-dimensional driving mechanism 78, to a desired location. Subsequently nanowires 12 are further opened, thus releasing object 74 in its appropriate location. In cases where object 74 fails to separate from nanowires 12, e.g., due to Van der Waals forces between object 74 and nanowires 12, a further voltage can be applied between nanowires 12 and the desired location, so that object 74 is released by an electrostatic attractive force.

Figure 20:
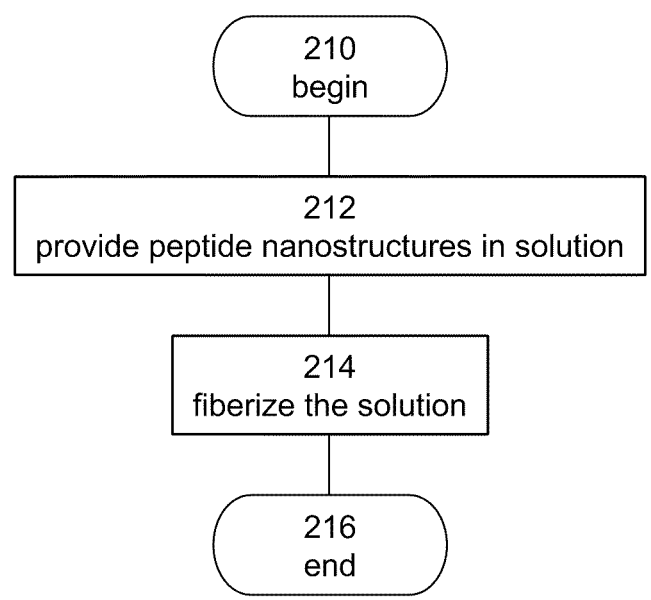
FIG. 20 is a flowchart diagram presenting a method suitable for forming a fiber made of peptide nanostructures, according to a preferred embodiment of the present invention.

Referring now to the drawings, FIG. 20 is a flowchart diagram of a method suitable for forming a fiber made of peptide nanostructures. The method begins at step 210 and continues to step 212 in which peptide nanostructures in solution are provided.

The solution can be prepared, for example, by placing or dissolving the nanostructures in an organic solvent, which is preferably an aromatic solvent, such as, but not limited to, benzene. Additionally, the solution may contain polymeric additives, or any other material suitable for forming fibers therefrom.

The method continues to step 214 in which the solution is fiberized to form at least one fiber of peptide nanostructures. The solution can be fiberized by any conventional process, such as, but not limited to, a spinning process, a blowing process, an injection process and the like. Contemplated spinning processes include, without limitation, wet spinning process, gel spinning process, dry spinning process, dispersion spinning process, reaction spinning process, tack spinning process and electrospinning process. The method ends at step 216.

These spinning processes are described in the Background section above and can be found in many text books and patents, see, e.g., U.S. Pat. Nos. 3,737,508, 3,950,478, 3,996,321, 4,189,336, 4,402,900, 4,421,707, 4,431,602, 4,557,732, 4,643,657, 4,804,511, 5,002,474, 5,122,329, 5,387,387, 5,667,743, 6,248,273 and 6,252,031 the contents of which are hereby incorporated by reference. Representative examples of spinning processes in various preferred embodiments of the present invention are further detailed hereinunder.

Following are representative examples of spinning methods which can be used in various preferred embodiments of the present invention.

In the embodiment in which electrospinning is employed, the solution with the peptide nanostructures is extruded, for example under the action of hydrostatic pressure, through capillary apertures of a dispenser, which is spaced apart from a precipitation electrode. The dispenser and precipitation electrode are kept at different electrical potentials thus forming an electric field therebetween. Under the effect of electrical force, jets depart from the dispenser and travel towards the precipitation electrode. Moving with high velocity in the inter-electrode space, the jet cools or solvent therein evaporates, thus forming fibers which are collected on the surface of the precipitation electrode.

In the embodiment in which a wet spinning process is employed, the solution with the peptide nanostructure of the present embodiments is extruded through a spinneret, under the action of mechanical forces (e.g., pressure, gravity). The formed fiber(s) can then be collected using a suitable take up device, e.g., a drum.

Figure 21:
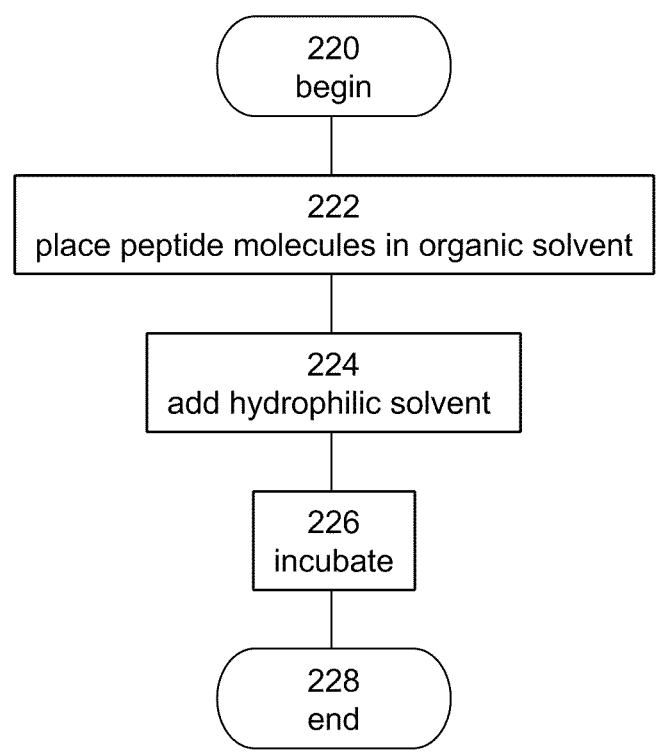
FIG. 21 is a flowchart diagram presenting a method suitable for forming a film of peptide nanostructures, according to a preferred embodiment of the present invention.

Reference is now made to FIG. 21 which is a flowchart diagram of a method suitable for forming a film of peptide nanostructures, according to a preferred embodiment of the present invention. The method begins at step 220 and continues to step 222 in which peptide molecule are placed in an organic solvent. The method continues to step 224 in which an hydrophilic solvent (e.g., water) is added to the organic solvent, such that an interface is formed between the organic and hydrophilic solvents. The method then proceeds to step 226 in which the organic and hydrophilic solvents are incubated under conditions which allow the peptide molecules to form a film of peptide nanostructures in the formed interface. The incubation conditions are such that the nanostructures are self-assembled as further detailed hereinabove. The method ends at step 228.

Figure 22:
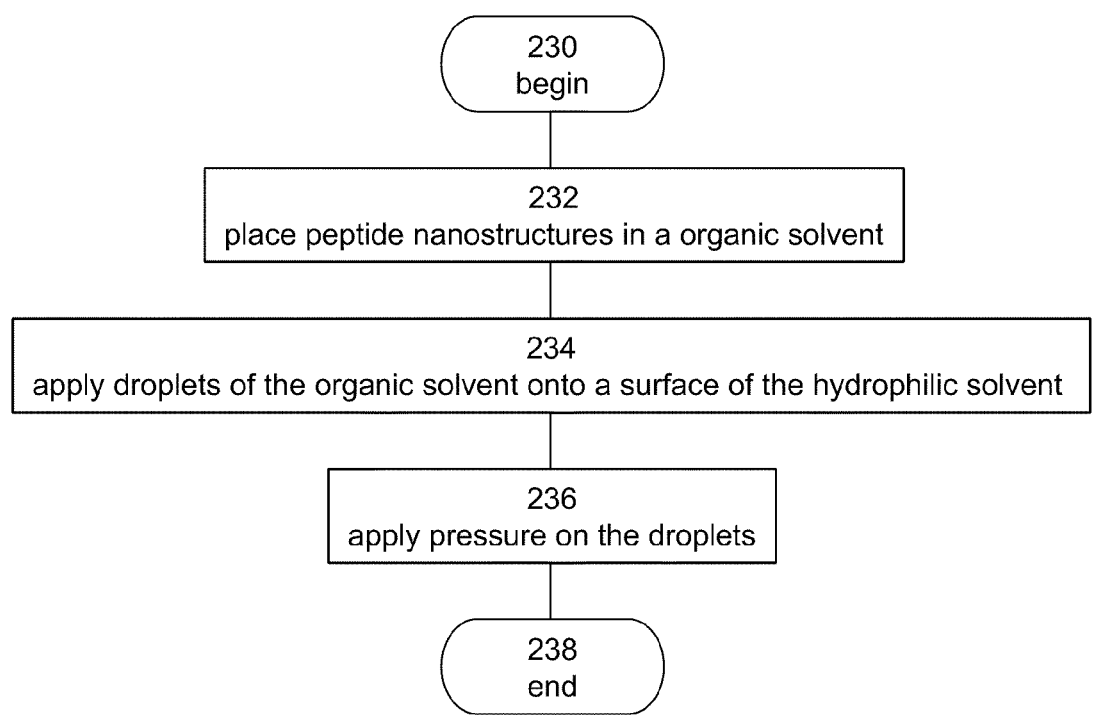
FIG. 22 is a flowchart diagram presenting a method suitable for forming one or more layers of peptide nanostructures, according to another preferred embodiment of the present invention.

Reference is now made to FIG. 22 which is a flowchart diagram of a method suitable for forming one or more layers of peptide nanostructures, according to another preferred embodiment of the present invention. The method begins at step 230 and continues to step 232 in which peptide nanostructures are placed in an organic solvent.

The method continues to step 234 in which one or more droplets of the organic solvent are applied onto a surface of a hydrophilic solvent. The method then continues to step 236 in which pressure is applied on the droplet of organic solvent, so as to form a layer of peptide nanostructures on the surface.

The application of pressure is preferably by moving barriers which can be made, for example, from Teflon®. The barriers reduce the surface area of the film and as a consequence the surface pressure of the layer increases. The pressure-area isotherm can be monitored continuously, e.g., by monitoring the surface are of the layer and measuring the force applied by the barrier. When pressure reaches some predetermined level, the barriers are stopped such that the layer is substantially in a steady state.

The layers can then be transferred to a substrate by any way known in the art, for example, the Langmuir-Blodgett technique or the Langmuir-Schaeffer technique.

When a Langmuir-Blodgett technique is employed, the substrate is preferably immersed a vertically through the layer. The substrate is then pulled up and the layer is transferred onto the substrate by lateral compression.

When a Langmuir-Schaeffer is employed, the substrate is descended horizontally onto the layer. Once a contact is made between the layer and the substrate, the substrate is extracted with the layer on it.

According to a preferred embodiment of the present invention the film can be subjected to a doping procedure. Doping procedures are known in the art and are found, for example, in the Handbook for conductive polymers, Edited by Terje A. Skotheim Vol. 1, 1986. This embodiment is particularly useful when it is desired to form a film with conductive properties.

Figure 23:
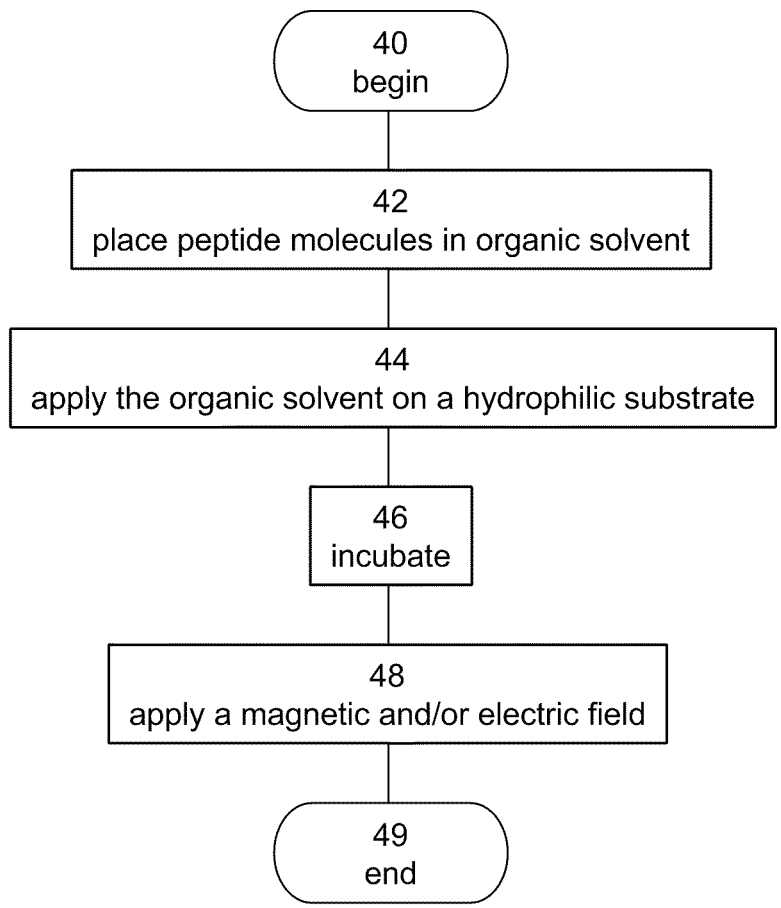
FIG. 23 is a flowchart diagram presenting a method suitable for forming an array or film of peptide nanostructures on a substrate, according to another preferred embodiment of the present invention.

Reference is now made to FIG. 23 which is a flowchart diagram of a method suitable for forming an array or film of peptide nanostructures on a substrate, according to a preferred embodiment of the present invention. The method begins at step 240 and continues to step 242 in which peptide molecule are placed in an organic solvent, such as, but not limited to, hexaflorupropanol. The method continues to step 244 in which the organic solvent is applied on a substrate, such as, but not limited to, a siliconized glass an ITO glass and the like. The method then proceeds to step 246 in which the substrate is incubated under conditions which allow the peptide molecules to form an array or film of peptide nanostructures on the substrate. The incubation conditions are preferably such that the nanostructures are self-assembled as further detailed hereinabove.

When the nanostructures are responsive to a magnetic and/or electric field (i.e., when a magnetic and/or electric field exerts a force on the nanostructures), the method preferably continues to step 248 in which the substrate is subjected to a magnetic and/or electric field. The advantage of this embodiment is that the forces can facilitate the assembling and/or alignment of the nanostructures on the substrate. Step 248 can be executed subsequently or contemporaneously with step 246. The method ends at step 249.

Performing one or more of the above methods according to present embodiments successfully produces a thin film of peptide nanostructures. In accordance with preferred embodiments of the present invention, the thin film is at least 100 nm$^2$, more preferably at least 1 μm$^2$, more preferably at least 10 μm$^2$ in area size. Such thin films can be used, for example, as artificial tissues in the filed of tissue engineering, as is detailed hereinafter.

The nanostructure of the present embodiments can be use to construct a matrix of an artificial tissue, which can be used for surgical training and/or for implantation in a subject during a medical operation. A matrix made of the nanostructure of the present invention is likely to be biocompatible and immuno-acceptable by the host, and allow cell which are incorporated into the matrix to grow and assimilate in the surrounding tissue. Furthermore, the matrix, being composed of peptide nanostructures, is biodegradable therefore can be eliminated by natural processes within the host.

For a cell implant or other type of viable cell insert to be effective, the cells must undergo any reorganization, growth and differentiation which is required to permit the cells to achieve normal functioning in the body. For a three-dimensional matrix holding the cells in a unitary mass to promote this result, it should satisfy all of the following criteria. The process used for forming the matrix must be rapid and sufficiently gentle to prevent cellular damage. The materials used must permit a rapid reaction under these gentle conditions. The process should allow shape and size control. For a process to be generally applicable for a variety of cells, it should produce shapes having controllable final cell densities ranging from particles containing one to a few cells to shapes containing cells at a density approaching the cell density in tissue, i.e., approximately from $10^9$-$10^{10}$ cells per cubic centimeter.

The ranges of size of the nanostructures should be selected to promote cell viability in a physiological environment. Soon after implantation, diffusion of oxygen and nutrients into the central interior of particles having excessive diameters would be insufficient, causing death of cells in the central interior.

The final nanostructure-made matrix must be nontoxic and biocompatible, and it can be biodegradable. The process should provide the ability to vary and control the matrix porosity to the level necessary to permit the requisite diffusion of nutrients and macromolecules. The process should be able to provide matrices which partially immobilize the cells to encourage cell-to-cell contact while being sufficiently loose to permit cell movement which may be necessary for rearrangement during tissue development. The matrix composition should also be susceptible to the degradation, removal or alteration in the host environment which is required for entry of the host cells into the matrix during the vascularization process.

All the abovementioned criteria can be satisfied with a matrix consisting of the nanostructures of the present invention.

The nanostructures of the present embodiments can also be used in the optical industry, for example, when the peptide nanostructures encapsulate inorganic crystals of semiconductor materials, crystalline organic semiconductor materials or compounds of any combination between semiconductor materials. In these cases the nanostructures serve for manipulating light.

The nanostructures of the present embodiments are preferably incorporated into an optical device. In various exemplary embodiments of the invention the optical device comprises waveguide core and the nanostructure of the present embodiments. Thus, the nanostructures of the present embodiments are suitable to be incorporated into many optical devices such as such as, but not limited to, waveguides structures (planar and non-planar), optical fibers, waveguide claddings, free-space optics, optical filters and hybrid optical devices. The nanostructures of the present embodiments can therefore be used in for switching, filtering, modulating and manipulating light in ways such as for an optical switch, an optical cross-connect, a wavelength converter and the like.

When the nanostructures form a thin film, the thin film can be used as an optical filter whereby the transmission, absorption and reflection sub-spectra of the filter can be controlled by the density of the nanostructures and the materials from which they are formed. When the nanostructures posses electrical charge, the optical properties can be controlled by application of electrical voltage to the film, such that the response of the peptide nanostructures to the applied voltage alters the optical properties.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Self-Assembly of Peptide Nanotubes and Amyloid Like Structures by Charged-Termini Capped Diphenylalanine Peptide Analogues The ability to form nanostructures from various modified peptides with emphasis on the charged state of their termini was examined.

Materials and Experimental Procedures:

Materials—End capping modified diphenylalanine peptides, presented in Table 3 hereinbelow, were purchase from Bachem (Bubendorf, Switzerland). Fresh stock solutions of the peptides were prepared by dissolving the lyophilized form of the peptides in 1,1,1,3,3,3-hexafluoro-2-propanol (HFIP, Sigma) at a concentration of 100 mg/ml. To avoid any pre-aggregation, fresh stock solutions were prepared for each experiment. The cyclo-Phe-Phe peptide (Peptide 8) was dissolved in HFIP to a concentration of 25 mg/ml and was subjected to ultrasound until a clear solution was obtained. The peptides stock solutions were diluted into a final concentration of 2 mg/ml in ddH$_2$O. The NH$_2$-Phe-Phe-NH$_2$ peptide (Peptide 3) was diluted into a final concentration of 10 mg/ml in ddH$_2$O.

TABLE 3

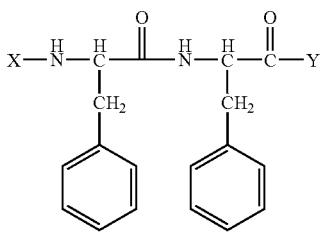

| Peptide | X | Y |
|---|---|---|
| 1 | H | OH |
| 2 | Ac | NH$_2$ |
| 3 | H | NH$_2$ |
| 4 | Ac | OH |
| 5 | Boc | OH |
| 6 | Fmoc | OH |
| 7 | Cbz | OH |
| 8 | Cyclo-[X-Y] | Cyclo-[X-Y] |

Scanning electron microscopy (SEM)—Immediately after dilution in ddH$_2$O, peptide solution was allowed to dry at room temperature over glass cover slip and coated with gold. Scanning electron microscopy images were obtained using a JSM JEOL 6300 SEM operating at 5 kV.

Transmission Electron microscopy (TEM)—Samples were placed on a 200 mesh copper grid, covered by carbon stabilized formvar film. After 1 minute excess fluid was removed and the grid was thereafter negatively stained with 2% uranyl acetate in water. After 2 minutes, excess fluid was removed from the grid. The samples were viewed in JEOL 1200EX electron microscope operating at 80 kV.

High resolution transmission electron microscopy—Samples were viewed using a Philips Tecnai F20 Field Emission Gun electron microscope operating at 200 kV. EDX analysis was performed with EDAX detector.

High resolution scanning electron microscopy—HRSEM grids were viewed using a JSM-6700 field emission scanning electron microscope equipped with a cold field emission gun operating at 1 kV.

Fourier Transform Infrared Spectroscopy—Infrared spectra were recorded using a Nicolet Nexus 470 FT-IR spectrometer with a deuterated triglycine sulfate (DTGS) detector. Peptide solution taken from the abovementioned SEM assays were deposited on a CaF$_2$ plate and dried under reduced pressure. The peptide deposits were resuspended with D$_2$O and subsequently dried to form thin films. The resuspension procedure was repeated twice to ensure maximal hydrogen to deuterium exchange. The measurements were taken using were taken using a 4 cm$^{-1}$ resolution and averaging of 2000 scans. The transmittance minimal values were determined by the OMNIC analysis program (Nicolet).

Atomic Force Microscope (AFM) imaging—The peptide sample solution was diluted again in ddH$_2$O to a concentration of 1 mg/ml. Then the peptide solution was placed on mica grade and dried in vacuum. Dried sample was analyzed using Molecular Imaging PicoSPM II system in tapping mode.

Results:

The first stage of the studies involved an end-capping modified dipeptide, Ac-Phe-Phe-NH$_2$ (see, Table 3, Peptide 2), in which the N-terminal amine was acetylated and the C-terminal carboxyl was amidated. Thus, this peptide contained no charged moieties. Yet, when the Ac-Phe-Phe-NH$_2$ peptide was incubated under the same conditions that resulted in the formation of nanotubes by NH$_2$-Phe-Phe-COOH (see, for example, WO 2004/052773), a rapid and efficient process of self-assembly occurred.

Figure 24:
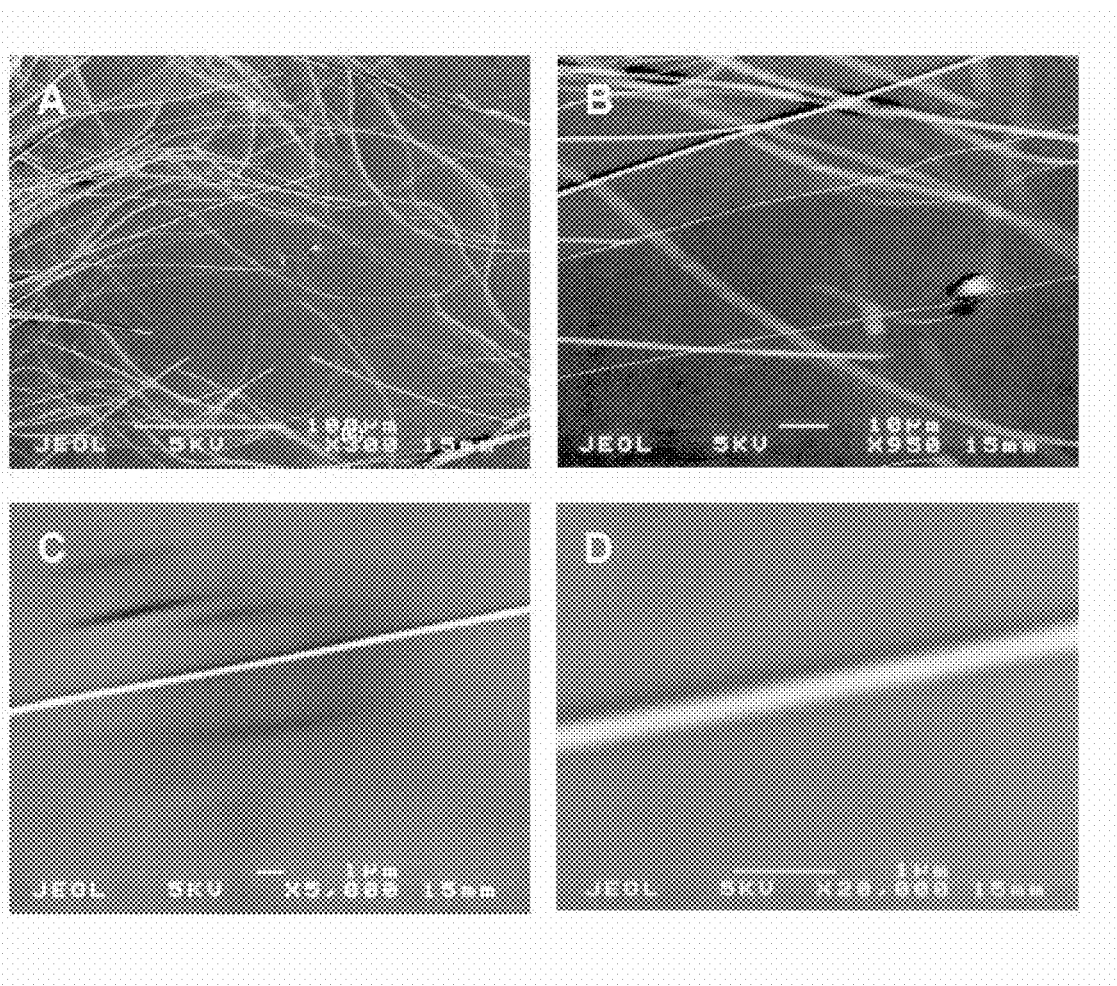
FIGS. 24a-d present photomicrographs showing increased SEM magnification of the tubular nanostructures formed by the Ac-Phe-Phe-NH$_2$ peptide.

Scanning electron microscopy (SEM) analysis revealed the formation of tubular structures within minutes after the dilution of a peptide stock into aqueous solution. The tubular structures were of varying diameters ranging from few microns to less than 100 nanometers and almost no amorphous structures were observed within the entire sample. FIG. 24 illustrates the range of sizes of the tubular structures as increased magnification of a specific area over the glass cover slip surface.

Figure 25:
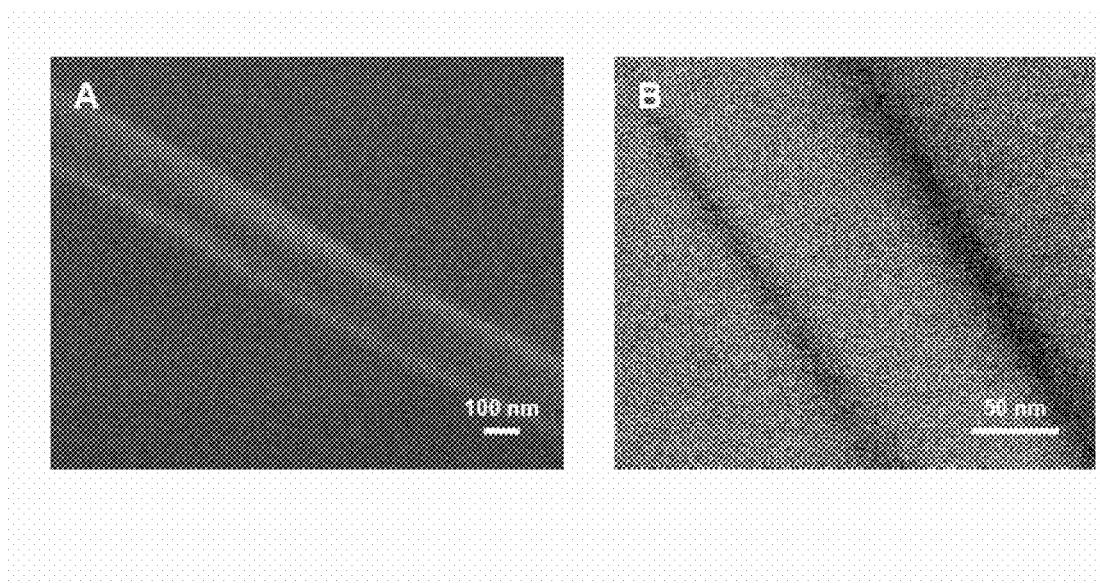
FIGS. 25a-b present high resolution images of a nanostructure formed from Ac-Phe-Phe-NH$_2$ peptide as obtained by cold field emission gun (CFEG) HR-SEM (FIG. 25a) and field emission gun (FEG) HR-TEM (FIG. 25b)

Additional microscopic analysis provided further confirmation to this phenomenon. In order to get further insights regarding the structural uniformity of the tubular structures they were analyzed using high resolution transmission electron microscope (TEM) and high resolution SEM. FIG. 25 presents two SEM images which illustrate the uniformity of the tubular structures as could be seen by this high resolution imaging technique.

Figure 26:
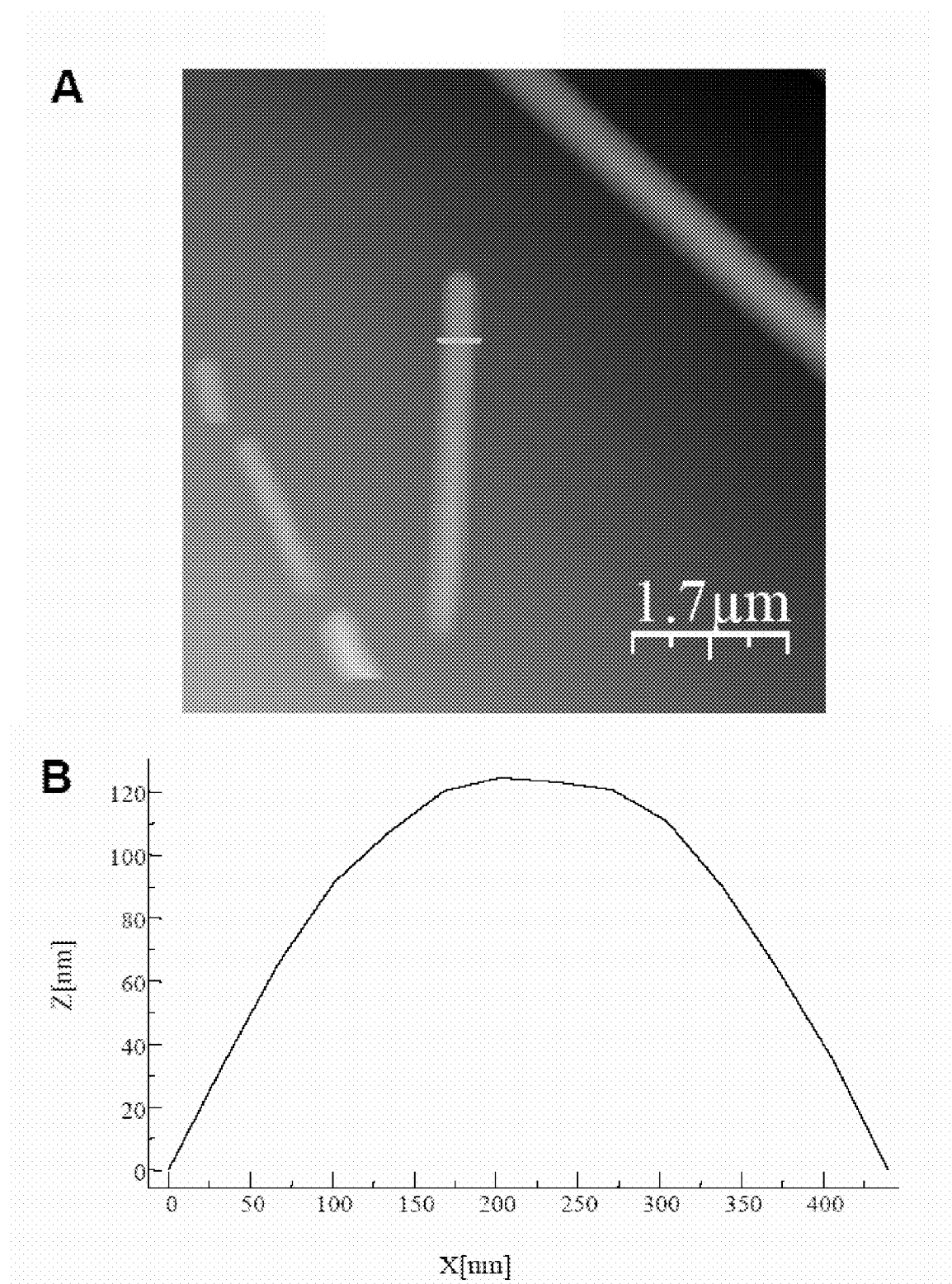
FIGS. 26a-b present an AFM topography image of peptide nanostructures formed from Ac-Phe-Phe-NH$_2$ (FIG. 26a) and a plot demonstrating the nanostructure height as derived from the AFM topography image.

To get further indication for the organization of the self-assembled peptide structures atomic force microscopy (AFM) was used. FIG. 26a presents an AFM image of the nanotubes which were formed by Peptide 2 (see, Table 3). The AFM analysis of assembled peptide structures deposited on mica further revealed organized and regular tubular structures with a three dimensional conformation. While AFM is not an ideal tool for the determination of the exact dimensions of the structures at the horizontal and vertical axis due to tip convolution, it is an excellent method to determine the height of nanotubes at the Z-range. Indeed, AFM analysis clearly indicated that the spheres are about 100 nm in height (FIG. 26b), which is consistent with both TEM and SEM analysis.

Figure 27:
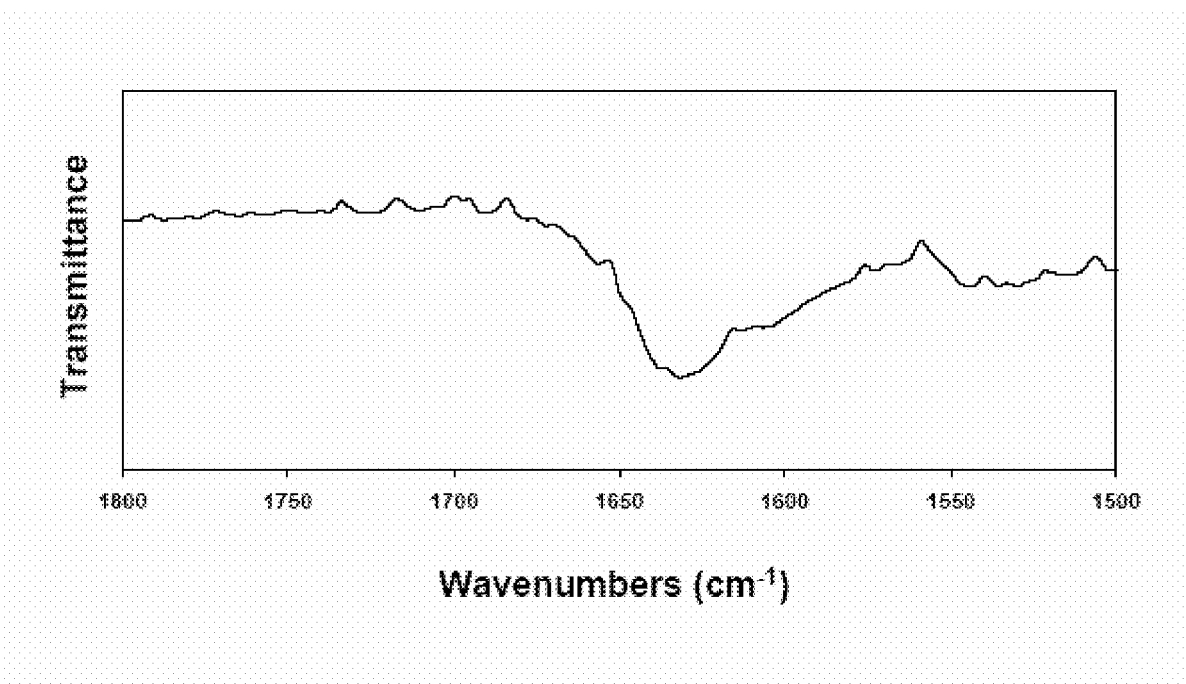
FIG. 27 presents a Fourier Transform Infrared (FT-IR) analysis spectra of the tubular nanostructures formed by Ac-Phe-Phe-NH$_2$, showing a single peak at 1631 cm$^{-1}$ which confirms a β-sheet conformation for this self-assembled nanostructures.

Moreover, Fourier Transform Infrared (FT-IR) analysis of the nanostructures formed by Peptide 2 showed a single peak at 1631 cm$^{-1}$ (FIG. 27) which confirmed a β-sheet conformation for these self-assembled tubular nanostructures. As the dipeptide has only a single amide bond, the spectroscopic analysis is definitive and does not represent an average property as is the case with larger peptides. This feature was also observed with the NH$_2$-Phe-Phe-COOH based nanotubes (see, for example, WO 2004/052773), what further supports the similarity between these tubular structures.

Figure 28:
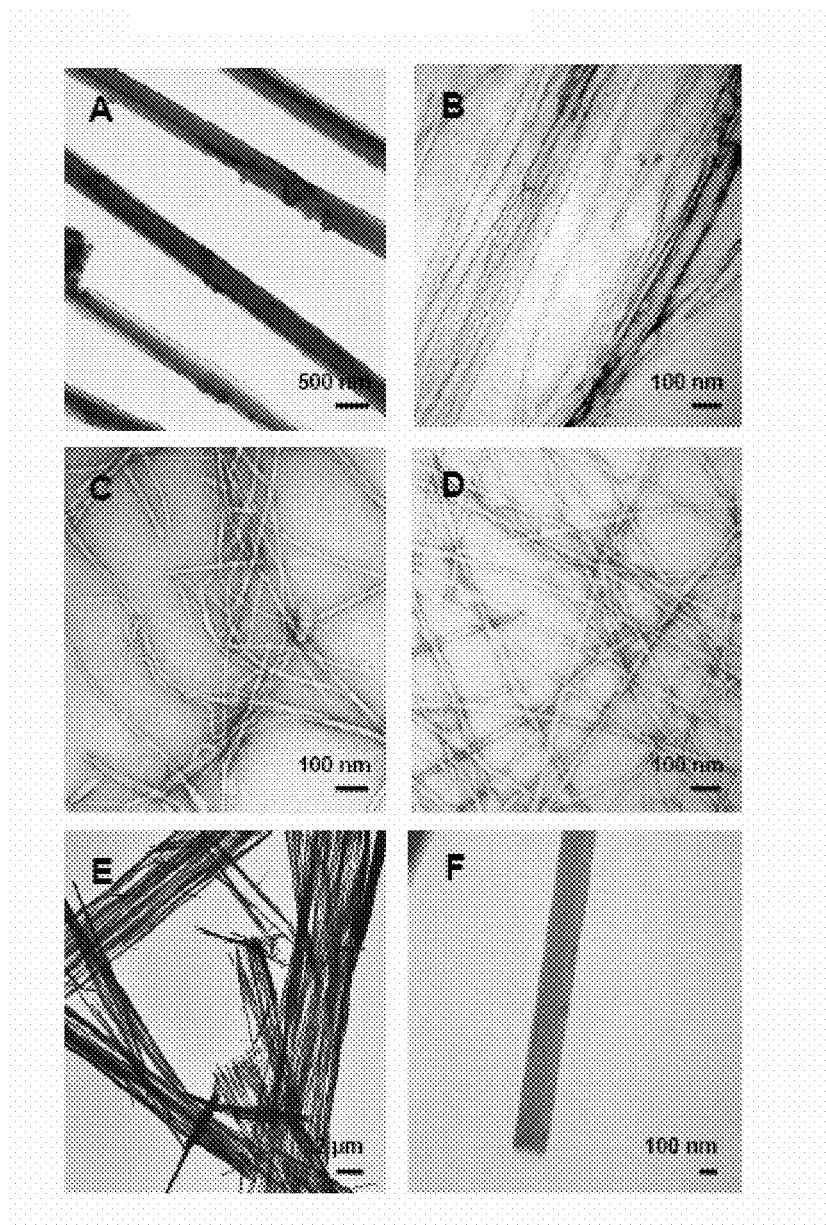
FIGS. 28a-f present TEM images of the various modified peptides (a) NH$_2$-Phe-Phe-NH$_2$; (b) Boc-Phe-Phe-COOH; (c) Fmoc-Phe-Phe-COOH; (d) Cbz-Phe-Phe-COOH; (e) Cyclo-Phe-Phe; and (f) a higher magnification of cyclo-Phe-Phe.
Figure 29:
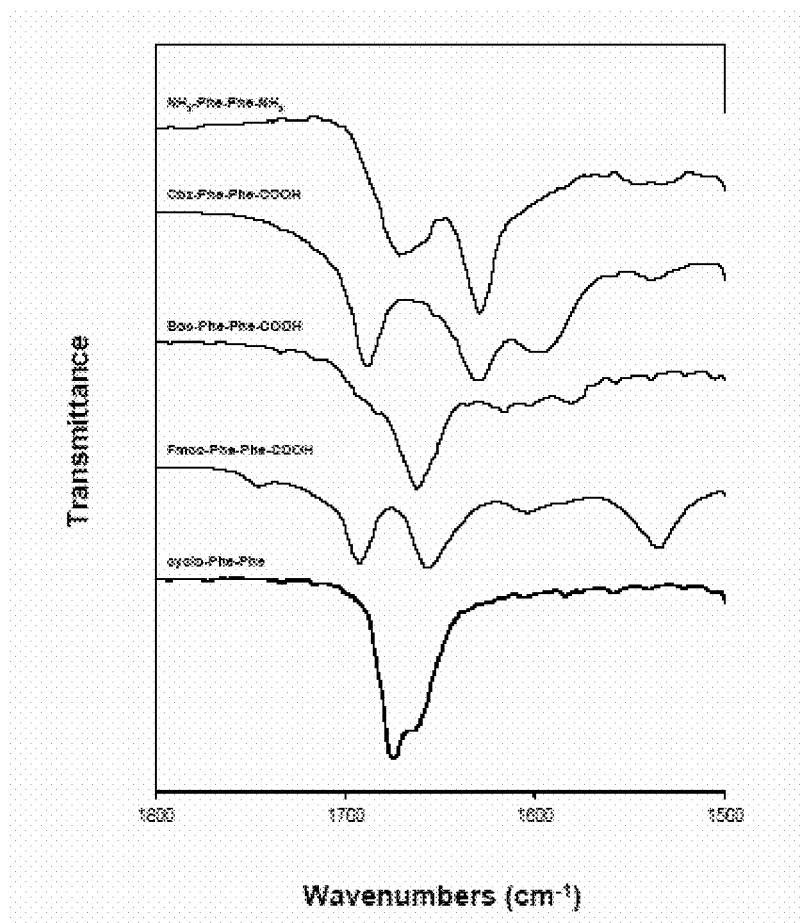
FIG. 29 presents a comparative Fourier Transform Infrared (FT-IR) analysis spectrum of the tubular nanostructures formed by the following peptides: cyclo-Phe-Phe (first curve from the bottom), Fmoc-Phe-Phe-COOH (second curve from the bottom), Boc-Phe-Phe-COOH (third curve from the bottom), Cbz-Phe-Phe-COOH (fourth curve from the bottom) and NH$_2$-Phe-Phe-NH$_2$ (fifth curve from the bottom), showing various features attributed to the internal arrangement of the nanostructures as affected by the amide bond conformation.

As the studies disclosed herein clearly proved the ability of the non-charged peptide to efficiently self-assemble into tubular structures, the present inventors further studied end-capping modified peptides in which only one of the two single charges was blocked. The first set of peptides included the NH$_2$-Phe-Phe-NH$_2$ (see, Table 3, Peptide 3) and Ac-Phe-Phe-COOH (see, Table 3, Peptide 4). Such modified peptides were assumed to offer the ability of efficient self-assembly, yet allow specific chemical modification through their reactive single amine or carboxyl moieties for the two peptides respectively. As expected, Peptide 3 efficiently self-assembled into tubular structures (see, FIG. 28a). These tubular assemblies most likely have an antiparallel β-sheet conformation, similar to amyloid fibrils or peptide nanotubes, as FTIR analysis showed peaks at 1629 cm$^{-1}$ and 1671 cm$^{-1}$ (see, FIG. 29, fifth curve from the bottom). On the other hand, unlike previously studied peptides, including the acetylated Ac-Phe-Phe-COOH Peptide 3, Peptide 4 did not dissolve either in water or in fluoroalcohols.

Additional amine modified peptides that were studied included the Boc-Phe-Phe-COOH (see, Table 3, Peptide 5), Fmoc-Phe-Phe-COOH (see, Table 3, Peptide 6) and Cbz-Phe-Phe-COOH (see, Table 3, Peptide 7) peptides. While Peptide 5 showed a clear ability to form highly ordered tubular structures (TEM analysis, see, FIG. 28b), Peptide 6 and Peptide 7 self assembled into a fibrillar structures which are more related to amyloid fibrils in their morphology and diameter (see, FIGS. 28c and 28d respectively).

The present inventors have previously demonstrated that peptides as short as penta- and tetrapeptides can self-assemble into well-ordered fibrillar structures [Reches, M.; Porat, Y.; Gazit E. J. Biol. Chem. 2002, 277, 3547535480; Gazit, E. FASEB J. 2002 16, 77-83; Azriel, R.; Gazit, E. J. Biol. Chem. 2001, 276, 34156-34161; Mazor, Y.; Gilead, S.; Benhar, I.; Gazit, E. J. Mol. Biol. 2002, 322, 1013-1024; Reches, M.; Gazit, E. Amyloid 2004, 11, 81-89; Porat, Y.; Mazor, Y.; Efrat, S.; Gazit, E. Biochemistry 2004, 43, 14454; and Dobson, C. M. Trends Biochem. Sci. 1999, 24, 329-332]. However, herein, fibril formation by a modified peptide as short as a dipeptide is demonstrated for the first time. These results further supports the notion that amyloid fibrils represent a generic form of aggregated protein structure [Dobson, C. M. Trends Biochem. Sci. 1999, 24, 329-332; and Gazit, E. Angew. Chem. Int. Ed. 2002, 41, 257-259]. The current results suggest that stacking of entities that contain a single planar peptide bond is sufficient for the formation of amyloid fibrils.

FT-IR studies of these amine-modified peptides show that these modified peptide may have molecular conformation that is quite different than that of amyloid fibrils or the canonical peptide nanotubes. The Boc-Phe-Phe-COOH peptide structures show a single amide-I peak at 1662 cm$^{-1}$, indicating a α-helix conformation. The Fmoc-Phe-Phe-COOH peptide show amide-I peaks at 1656 cm$^{-1}$ and 1692 cm$^{-1}$. The Cbz-Phe-Phe-COOH peptide has an antiparallel β-sheet conformation as FTIR analysis showed a peak at 1629 cm$^{-1}$ and 1688 cm$^{-1}$ (see, FIG. 29, fourth curve from the bottom). The results of this structural analysis suggest that some of the modified peptides might have completely different molecular conformation of the amide-I bond as compared to the other self-assembled ordered aromatic peptide structures.

Another non charged analogue of the diphenylalanine peptide examined by the present inventors was the cyclo-Phe-Phe peptide (see, Table 3, Peptide 8). This cyclic peptide also features no charge moieties together with a highly restricted structural conformation. This cyclic peptide also self assembled into bundles of tubular structures (see, FIGS. 28e and 28f). Also in this case the amide-I conformation appears to be different than the typical peptide tube or amyloid deposits as the FTIR analysis of these structures revealed two peaks one at 1664 cm$^{-1}$ and the other one at 1674 cm$^{-1}$. This result indicates either an α-helix or a β-turn conformation for these structures.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

---

What is claimed is:

1. An artificial tissue comprising viable cells incorporated throughout a porous biocompatible matrix composed of at least one nanostructure, said at least one nanostructure being selected from the group consisting of a tubular nanostructure and a fibrillar nanostructure, and comprising a plurality of aromatic homodipeptides, wherein at least one of said homodipeptides is an end-capping modified peptide.

2. The artificial tissue of claim 1, wherein said end capping moiety is an aromatic moiety and the nanostructure is a fibrillar nanostructure.

3. The artificial tissue of claim 2, wherein said aromatic end capping moiety is selected from the group consisting of 9-fluorenylmethyloxycarbonyl (Fmoc) and benzyloxycarbonyl (Cbz).

4. The artificial tissue of claim 1, wherein said end-capping moiety is a non-aromatic moiety and the nanostructure is a tubular nanostructure.

5. The artificial tissue of claim 4, wherein said non-aromatic end capping moiety is selected from the group consisting of acetyl and tert-butoxycarbonyl (Boc).

6. The artificial tissue of claim 1, wherein said homodipeptide is phenylalanine-phenylalanine dipeptide.

7. The artificial tissue of claim 1, wherein said homodipeptide is selected from the group consisting of naphthylalanine-naphthylalanine dipeptide, (pentafluro-phenylalanine)-(pentafluro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

8. The artificial tissue of claim 1, wherein said end-capping modified peptide has the general Formula I:

$$R_1\text{-}[A_1]\text{-}[A_2]\text{-}R_2 \quad \text{Formula I}$$

wherein:

$A_1$ and $A_2$ are each an aromatic amino acid residue and are the same;

$R_1$ is selected from the group consisting of N-terminus amine and an N-terminus end-capping moiety; and $R_2$ is elected from the group consisting of C-terminus carboxylic acid and a C-terminus end-capping moiety, provided that at least one of $R_1$ and $R_2$ is an end capping moiety.

9. A matrix made of at least one nanostructure, said at least one nanostructure being selected from the group consisting of a tubular nanostructure and a fibrillar nanostructure, and comprising a plurality of aromatic homodipeptides, wherein at least one of said homodipeptides is an end-capping modified peptide, the matrix being capable of introducing and growing therethrough cells.

10. The matrix of claim 9, wherein said end-capping modified peptide comprises an aromatic end capping moiety.

11. The matrix of claim 10, wherein said aromatic end-capping moiety is selected from the group consisting of 9-fluorenylmethyloxycarbonyl (Fmoc) and benzyloxycarbonyl (Cbz).

12. The matrix of claim 9, wherein said homodipeptide is phenylalanine-phenylalanine dipeptide.

* * * * *